United States Patent
Jacobson et al.

(10) Patent No.: US 10,683,277 B2
(45) Date of Patent: Jun. 16, 2020

(54) TRIAZOLE DERIVATIVES AS P2Y$_{14}$ RECEPTOR ANTAGONISTS

(71) Applicant: The United States of America, as represented by the Secretary, Department of Health and Human Services, Bethesda, MD (US)

(72) Inventors: Kenneth A. Jacobson, Silver Spring, MD (US); Anna Junker, Wallenhorst (DE); Elisa Uliassi, Bologna (IT); Evgeny Kiselev, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/762,852

(22) PCT Filed: Sep. 23, 2016

(86) PCT No.: PCT/US2016/053397
§ 371 (c)(1),
(2) Date: Mar. 23, 2018

(87) PCT Pub. No.: WO2017/053769
PCT Pub. Date: Mar. 30, 2017

(65) Prior Publication Data
US 2018/0297981 A1 Oct. 18, 2018

Related U.S. Application Data

(60) Provisional application No. 62/233,162, filed on Sep. 25, 2015.

(51) Int. Cl.
C07D 401/06 (2006.01)
C07D 401/10 (2006.01)
C07D 401/14 (2006.01)
C07D 211/18 (2006.01)
C07D 417/14 (2006.01)
C07D 405/14 (2006.01)
C07D 409/14 (2006.01)

(52) U.S. Cl.
CPC .......... *C07D 401/10* (2013.01); *C07D 211/18* (2013.01); *C07D 401/06* (2013.01); *C07D 401/14* (2013.01); *C07D 405/14* (2013.01); *C07D 409/14* (2013.01); *C07D 417/14* (2013.01)

(58) Field of Classification Search
CPC .. C07D 401/06; C07D 401/10; C07D 401/14; C07D 211/18; C07D 417/14; C07D 405/14; C07D 409/14
See application file for complete search history.

(56) References Cited

U.S. PATENT DOCUMENTS

| 4,507,466 A | 3/1985 | Tomalia et al. |
| 5,530,092 A | 6/1996 | Meijer et al. |

FOREIGN PATENT DOCUMENTS

| WO | WO 93/21144 A1 | 10/1993 |
| WO | WO 2005/075453 A1 | 8/2005 |
| WO | WO 2009/070873 A1 | 6/2009 |

OTHER PUBLICATIONS

Yu et al., 2018, J. Med. Chem., 61, 4860-4882.*
LipidDisorder, 2019, https://www.healthline.com/health/high-cholesterol/lipid-disorder.*
Kita et al., 2003, caplus 2003:773843.*
Barrett et al., "A Selective High-Affinity Antagonist of the P2Y$_{14}$ Receptor Inhibits UDP-Glucose-Stimulated Chemotaxis of Human Neutrophils," *Mol. Pharmacol.*, 84(1), 41-49 (2013).
Cho et al., "Highly Stable Positively Charged Dendron-Encapsulated Gold Nanoparticles," *Langmuir*, 30(13), 3883-3893 (2014).
Cho et al., "Newkome-type dendron stabilized gold nanoparticles: Synthesis, reactivity, and stability," *Chem Mater.*, 23(10), 2665-2676 (2011) Author Manuscript.

(Continued)

*Primary Examiner* — Sun Jae Yoo
(74) *Attorney, Agent, or Firm* — Leydig, Voit & Mayer, Ltd.

(57) ABSTRACT

Described are compounds, which are antagonists of the P2Y$_{14}$ receptor, for example, a compound of formula (I) in which ring A, R$^1$, R$^2$, R$^3$, and n are as described herein. Also provided are dendron conjugates comprising the compounds, and methods of using the compounds, including a method of treating a disorder, such as inflammation, diabetes, insulin resistance, hyperglycemia, a lipid disorder, obesity, a condition associated with metabolic syndrome, and asthma, and a method of antagonizing P2$_{14}$ receptor activity in a cell.

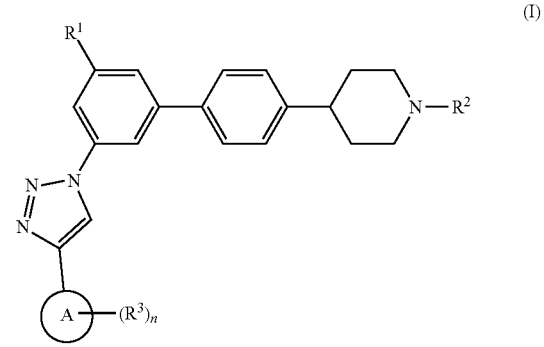

23 Claims, 17 Drawing Sheets

(56) References Cited

OTHER PUBLICATIONS

Gauthier et al., "The identification of 4,7-disubstituted naphthoic acid derivatives as UDP-competitive antagonists of $P2Y_{14}$," *Bioorganic and Medicinal Chemistry Letters*, 21(10), 2836-2839 (2011).

Guay et al., "Synthesis and SAR of pyrimidine-based, non-nucleotide $P2Y_{14}$ receptor antagonists," *Bioorganic and Medicinal Chemistry Letters*, 21(10), 2832-2835 (2011).

International Preliminary Report on Patentability, Application No. PCTUS2016/053397, dated Mar. 27, 2018.

International Search Report, Application No. PCT/US2016/053397, dated Nov. 14, 2016.

Junker et al., "Structure-Based Design of 3-(4-Aryl-1H-1,2,3-triazol-1-yl)-Biphenyl Derivatives as $P2Y_{14}$ Receptor Antagonists," *J. Med. Chem.*, 59(13), 6149-6168 (2016).

Kiselev et al., "Exploring a 2-Naphthoic Acid Template for the Structure-Based Design of $P2Y_{14}$ Receptor Antagonist Molecular Probes," *ACS Chem. Biol.*, 9(12), 2833-2842 (2014).

Lazarowski et al., "UDP-sugars as extracellular signaling molecules: cellular and physiological consequences of $P2Y_{14}$ receptor activation," *Molecular Pharmacology*, 88, 151-160 (Jul. 2015).

Newkome et al., "Cascade Polymers: Synthesis and Characterization of Four-Directional Spherical Dendritic Macromolecules Based on Adamantane," *J. Org. Chem.*, 57(1), 358-362 (1992).

Newkome et al., "Cascade Polymers: Syntheses and characterization of One-Directional Arborols Based on Adamantane," *J. Org. Chem.*, 56(25), 7162-7167 (1991).

Robichaud et al., "Applying the pro-drug approach to afford highly bioavailable antagonists of $P2Y_{14}$," *Bioorganic and Medicinal Chemistry Letters*, 21(14), 4366-4368 (2011).

Tsai et al., "Quantitative analysis of dendron-conjugated cisplatin-complexed gold nanoparticles using scanning particle mobility mass spectrometry," *Nanoscale*, 5(12), 5390-5395 (2013).

Written Opinion of the International Searching Authority, Application No. PCT/US2016/053397, dated Nov. 14, 2016.

Xu et al., "GPR105 Ablation Prevents Inflammation and Improves Insulin Sensitivity in Mice with Diet-Induced Obesity," *J. Immunol.*, 189(4), 1992-1999 (2012).

Zhang et al., "Agonist-bound structure of the human $P2Y_{12}$ receptor," *Nature*, 509(7498), 119-122 (2014) Author Manuscript.

Azroyan et al., "Renal Intercalated Cells Sense and Mediate Inflammation via the $P2Y_{14}$ Receptor," *PLoS One*, 10(3): e0121419 (2015).

Gao et al., "The role of $P2Y_{14}$ and other P2Y receptors in degranulation of human LAD2 mast cells," *Purinergic Signalling*, 9(1): 31-40 (2013).

Jacobson et al., "$P2Y_{14}$ Receptor," *Encyclopedia of Signaling Molecules*, Ed. S. Choi (2016).

Robichaud et al., "Applying the pro-drug approach to afford highly bioavailable antagonists of $P2Y_{14}$," *Bioorg. Med. Chem. Lett.*, 21(14): 4366-4368 (2011).

Sesma et al., "Udp-glucose promotes neutrophil recruitment in the lung," *Purinergic Signalling*, 12(4): 627-635 (2016).

Holister et al., "Dendrimers Technology White Papers Nr. 6," *Cientifica* pp. 3-15 (Oct. 2003).

European Patent Office, Office Action, Application No. 16774825.0, dated Nov. 28, 2019, 5 pages.

* cited by examiner

PRIOR ART COMPOUNDS

TRIAZOLE DERIVATIVES AS P2Y$_{14}$ RECEPTOR ANTAGONISTS

CROSS-REFERENCE TO RELATED APPLICATIONS

This patent application is a U.S. national phase of International Patent Application No. PCT/US2016/053397, filed Sep. 23, 2016, which claims the benefit of U.S. Provisional Patent Application No. 62/233,162, filed Sep. 25, 2015, the disclosures of which are incorporated by reference for all purposes.

STATEMENT REGARDING FEDERALLY SPONSORED RESEARCH OR DEVELOPMENT

This invention was made with Government support under project number Z01 DK 031116-25 by the National Institutes of Health, National Institute of Diabetes and Digestive and Kidney Diseases. The Government has certain rights in the invention.

BACKGROUND OF THE INVENTION

Extracellular uridine-5'-diphosphate 1 and uridine-5'-diphosphoglucose 2 (FIG. 1) activate the P2Y$_{14}$ receptor (P2Y$_{14}$R), a G protein-coupled receptor (GPCR) of the δ-branch of Family A, to modulate function in models of inflammation, diabetes, asthma and other diseases (Lazarowski et al., *Mol. Pharmacol.* 2015, 88(1), 151-160; and Abbracchio et al., *Pharmacol. Rev.* 2006, 58, 281-341). This receptor subtype is a member of the P2Y$_{12}$R-like subfamily of nucleotide receptors, which inhibits the production of cyclic AMP through Gi protein. The P2Y$_{14}$R promotes hypersensitivity in microglial cells (Kobayashi et al., *Glia* 2012, 60, 1529-1539), the mobility of neutrophils (Sesma et al., *Am. J. Physiol.—Cell Physiol.* 2012, 303, C490-C498), the release of mediators from mast cells (Gao et al., *Biochem. Pharmacol.* 2010, 79, 873-879), inflammation in renal intercalated cells (Azroyan et al., *PLoS ONE* 2015, 10(3), e0121419. doi:10.1371/journal.pone.0121419) and mixed effects in insulin function (Xu et al., *J. Immunol.* 2012, 189(4), 1992-1999; and Meister et al., *J. Biol. Chem.* 2014, 289, 23353-23366). Thus, approaches to novel antagonists of nucleotide signaling at the P2Y$_{14}$R would be desirable for exploration as novel therapeutics for treating diseases associated with modulating P2Y$_{14}$R.

Only a limited set of P2Y$_{14}$R antagonists are currently known. Several chemotypes based on naphthoic acid and pyrido[4,3-d]pyrimidine have been reported to provide potent P2Y$_{14}$R antagonists, but displayed low oral bioavailability (International Patent Application WO 2009/070873; Gauthier et al., *Bioorg. Med. Chem. Lett.* 2011, 21, 2836-2839; Guay et al., *Bioorg. Med. Chem. Lett.* 2011, 21, 2832-2835; and Robichaud et al., *Bioorg. Med. Chem. Lett.* 2011, 21, 4366-4368).

Despite these efforts, there remains an unmet need for novel antagonists with improved potency, selectivity, and/or bioavailability for the treatment of disorders that respond to modulating P2Y$_{14}$R.

BRIEF SUMMARY OF THE INVENTION

The present invention provides a compound of formula (I):

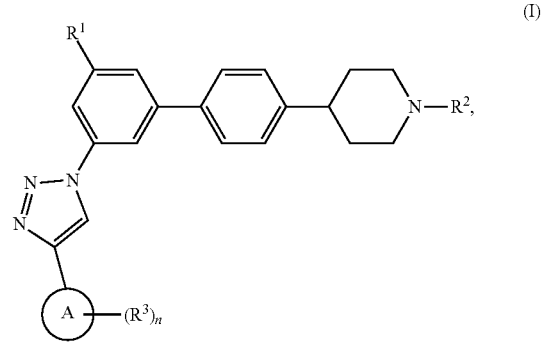

in which ring A, R$^1$, R$^2$, R$^3$, and n are as described herein. Also provided is a compound of formula (II),

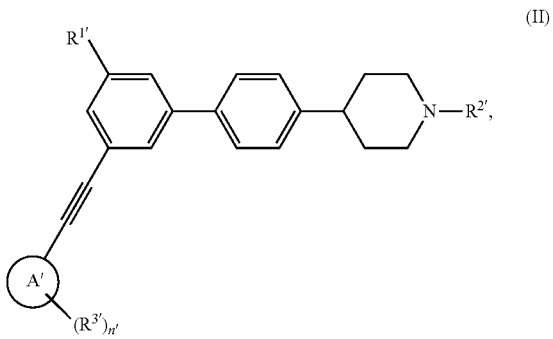

in which ring A', R$^{1'}$, R$^{2'}$, R$^{3'}$, and n' are as described herein. It has been discovered that a compound defined herein is effective in antagonizing P2Y$_{14}$R activity. It is envisioned that a compound of formula (I) or (II) is desirable for therapeutic applications because the compound inhibits P2Y$_{14}$R to modulate function in models of inflammation, diabetes, insulin resistance, hyperglycemia, a lipid disorder, obesity, a condition associated with metabolic syndrome, and asthma.

The invention also provides a dendron conjugate that comprises a compound of formula (I) or (II), which can have a structure of formula (III) or (IV), respectively:

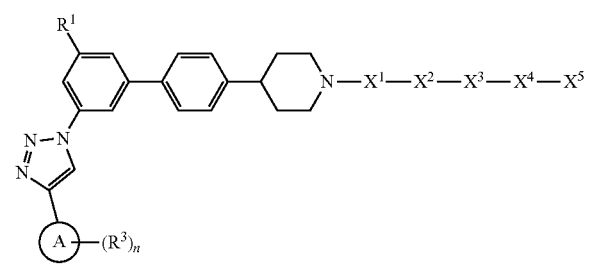

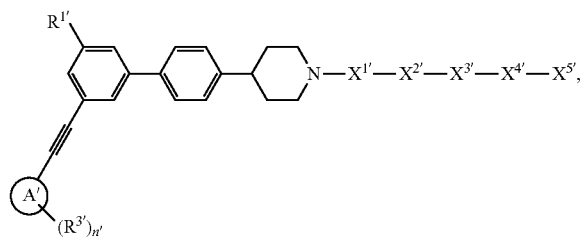

(IV)

in which ring A, $R^1$, $R^3$, $X^1$, $X^2$, $X^3$, $X^4$, $X^5$, n, ring A', $R^{1'}$, $R^{3'}$, $X^{1'}$, $X^{2'}$, $X^{3'}$, $X^{4'}$, $X^{5'}$, and n' are as described herein.

The compounds of formula (I) and (II) simultaneously reduce the molecular weight and avoid the high lipophilicity of the naphthoic acid and pyrido[4,3-d]pyrimidine derivative 3 (FIG. 1) that contributes to its low solubility and difficulty of purification (Robichaud et al., *Bioorg. Med. Chem. Lett.* 2011, 21(14), 4366-4368).

Thus, the invention further provides a method for treating inflammation, diabetes, insulin resistance, hyperglycemia, a lipid disorder, obesity, a condition associated with metabolic syndrome, or asthma in a mammal in need thereof, which comprises administering a therapeutically effective amount of a compound of formula (I) or (II) or a pharmaceutically acceptable salt thereof to the mammal.

Also provided is a method of antagonizing $P2Y_{14}R$ activity in a cell comprising administering a compound of formula (I) or (II), a conjugate thereof, or a pharmaceutically acceptable salt thereof to a cell, whereby activity of $P2Y_{14}R$ is antagonized.

DETAILED DESCRIPTION OF THE INVENTION

Figure 1:
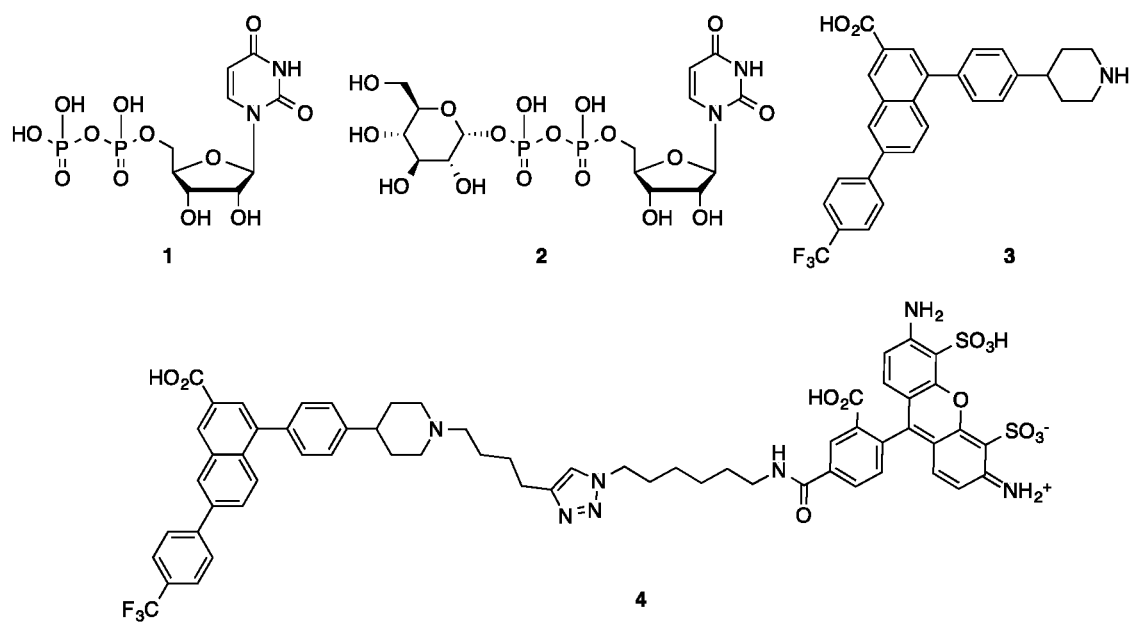
FIG. 1 shows prior art agonist and antagonist ligand probes of the $P2Y_{14}R$.

The present invention provides a compound of formula (I):

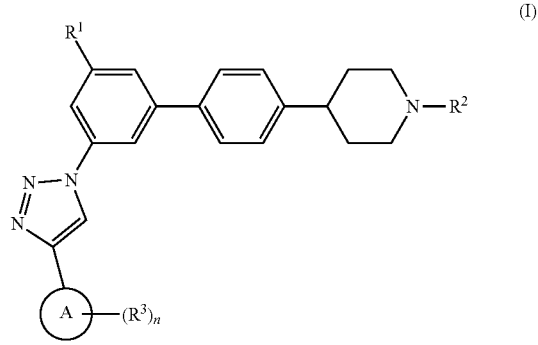

wherein
ring A is aryl, heteroaryl, or cycloalkyl;
$R^1$ is —$CO_2H$, —$CO_2(C_1$-$C_8$ alkyl), or a bioisostere of carboxylate;
$R^2$ is H, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyalkyl, $C_1$-$C_8$ haloalkyl, cyanoalkyl, aryl, heteroaryl, heterocycloalkyl, —(CH$_2$)$_m$aryl, —(CH$_2$)$_m$heteroaryl, or —(CH$_2$)$_m$heterocycloalkyl;

each R$^3$ is the same or different and each is C$_1$-C$_8$ alkyl, C$_2$-C$_8$ alkenyl, C$_3$-C$_6$ cycloalkyl, hydroxy, hydroxyalkyl, C$_1$-C$_8$ alkoxy, C$_3$-C$_6$ cycloalkyloxy, aryloxy, halo, C$_1$-C$_8$ haloalkyl, C$_1$-C$_8$ haloalkoxy, —CN, —NO$_2$, —NR$^5$R$^6$, —C(O)R$^4$, —CO$_2$R$^4$, —C(O)NR$^5$R$^6$, —NR$^5$C(O)R$^4$, —(CH$_2$)$_m$aryl, —(CH$_2$)$_m$heteroaryl, or —(CH$_2$)$_m$heterocycloalkyl;

R$^4$, R$^5$, and R$^6$ are the same or different and each is H or C$_1$-C$_8$ alkyl; and m and n are the same or different and each is 0 or an integer from 1-5;

or a pharmaceutically acceptable salt thereof.

In certain compounds, ring A is phenyl, furanyl, thiazolyl, thienyl, pyrazolyl, pyridazinyl, pyridinyl, pyrazinyl, benzofuranyl, cyclopropyl, or cyclohexyl. In a preferred embodiment, ring A is phenyl.

In some embodiments, R$^1$ is —CO$_2$H. In other embodiments, R$^1$ is any suitable bioisostere of carboxylate, particularly a bioisostere that improves at least one property of the compound of formula (I), such as improves bioavailability and/or increases the binding affinity of a compound of formula (I) to P2Y$_{14}$R. Examples of a suitable bioisostere of carboxylate include

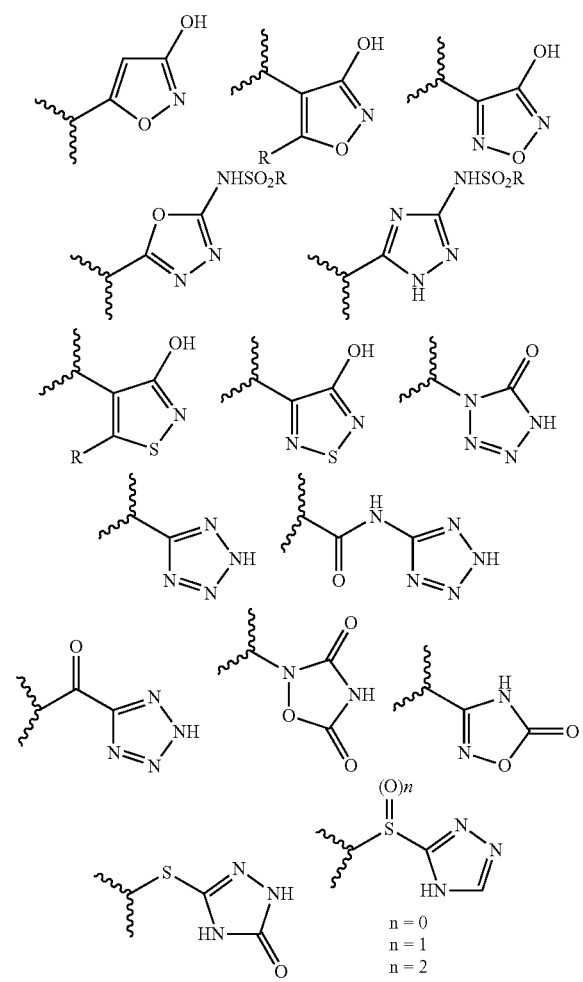

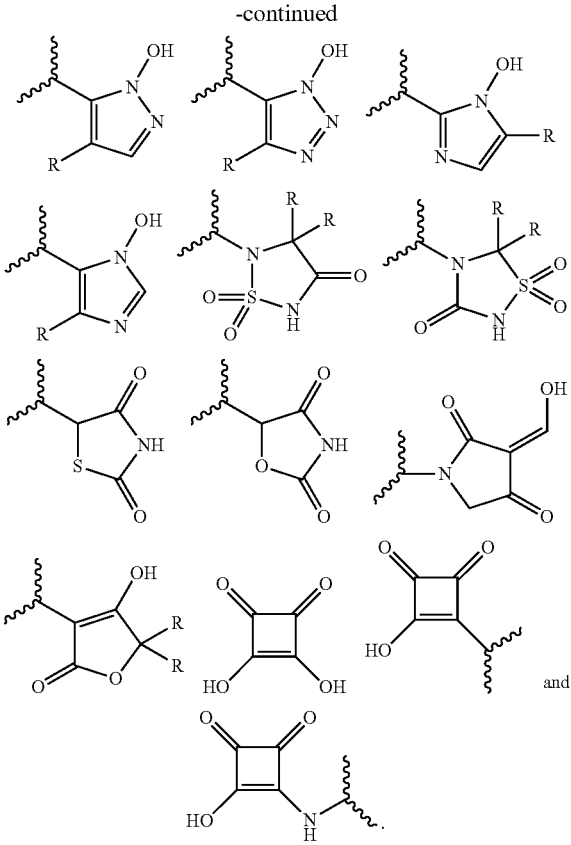

In any of the foregoing embodiments, R$^2$ is H or C$_2$-C$_8$ alkynyl.

In any of the foregoing embodiments, R$^3$ is C$_1$-C$_8$ alkyl, hydroxy, hydroxyalkyl, C$_1$-C$_8$ alkoxy, halo, C$_1$-C$_8$ haloalkyl, C$_1$-C$_8$ haloalkoxy, —CN, —NH$_2$, or —CO$_2$R$^4$.

In any of the foregoing embodiments, n is 0 or 1 or 2.

In some embodiments of the compound of formula (I),

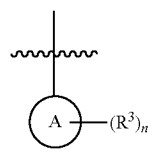

is selected from the group consisting of (optionally in combination with R$^1$ being —CO$_2$H and R$^2$ being H):

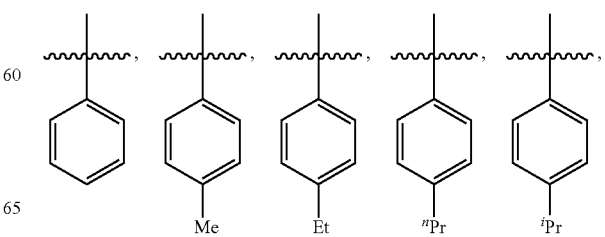

-continued

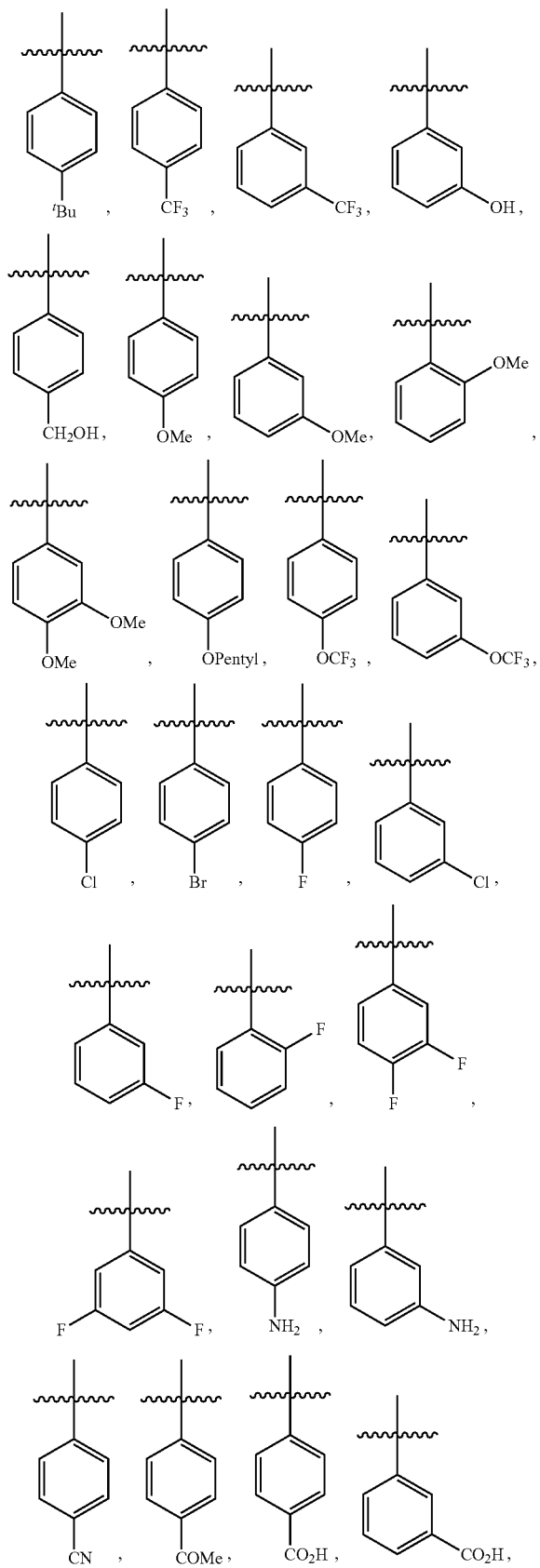

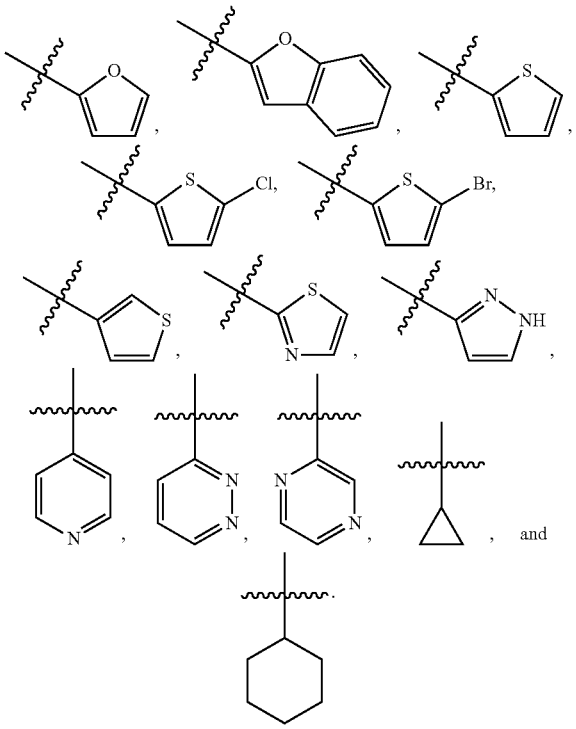

In another aspect of the invention is a compound of formula (II):

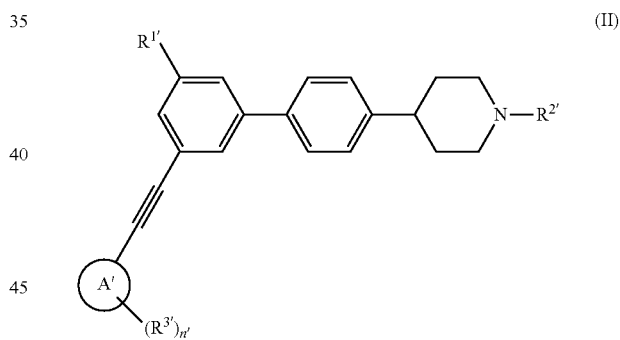

wherein
ring A' is aryl, heteroaryl, or cycloalkyl;
R$^{1'}$ is —CO$_2$H, —CO$_2$(C$_1$-C$_8$ alkyl), or a bioisostere of carboxylate;
R$^{2'}$ is H, C$_1$-C$_8$ alkyl, C$_2$-C$_8$ alkenyl, C$_2$-C$_8$ alkynyl, C$_3$-C$_6$ cycloalkyl, C$_3$-C$_6$ cycloalkylalkyl, hydroxyalkyl, C$_1$-C$_8$ haloalkyl, cyanoalkyl, aryl, heteroaryl, heterocycloalkyl, —(CH$_2$)$_m$aryl, —(CH$_2$)$_m$heteroaryl, or —(CH$_2$)$_m$heterocycloalkyl;
each R$^{3'}$ is the same or different and each is C$_1$-C$_8$ alkyl, C$_2$-C$_8$ alkenyl, C$_3$-C$_6$ cycloalkyl, hydroxy, hydroxyalkyl, C$_1$-C$_8$ alkoxy, C$_3$-C$_6$ cycloalkyloxy, aryloxy, halo, C$_1$-C$_8$ haloalkyl, C$_1$-C$_8$ haloalkoxy, —CN, —NO$_2$, —NR$^{5'}$R$^{6'}$, —C(O)R$^{4'}$, —CO$_2$R$^{4'}$, —C(O)NR$^{5'}$R$^{6'}$, —NR$^{5'}$C(O)R$^{4'}$, —(CH$_2$)$_m$aryl, —(CH$_2$)$_m$heteroaryl, or —(CH$_2$)$_m$heterocycloalkyl;
R$^{4'}$, R$^{5'}$, and R$^{6'}$ are the same or different and each is H or C$_1$-C$_8$ alkyl; and m' and n' are the same or different and each is 0 or an integer from 1-5;

or a pharmaceutically acceptable salt thereof.

In certain compounds of formula (II), ring A' is phenyl, furanyl, thiazolyl, thienyl, pyrazolyl, pyridazinyl, pyridinyl, pyrazinyl, benzofuranyl, cyclopropyl, or cyclohexyl. In a preferred embodiment, ring A' is phenyl.

In some embodiments of formula (II), $R^{1'}$ is —$CO_2H$. In other embodiments, $R^{1'}$ is any suitable bioisostere of carboxylate, particularly a bioisostere that improves at least one property of the compound of formula (II), such as improves bioavailability and/or increases the binding affinity of a compound of formula (II) to $P2Y_{14}R$. Examples of a suitable bioisostere of carboxylate include

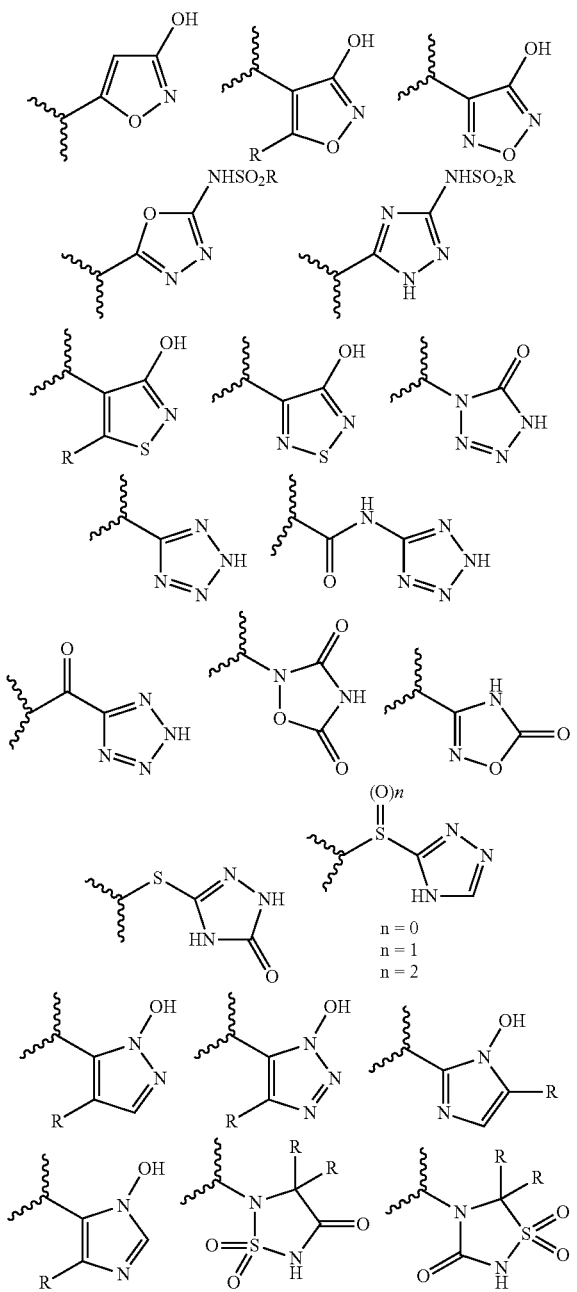

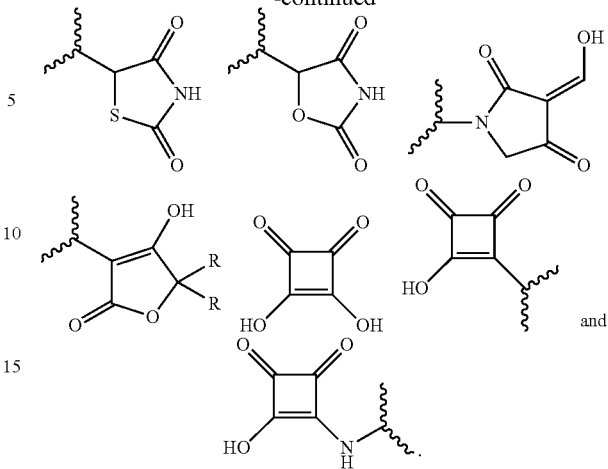

In any of the foregoing embodiments, $R^{2'}$ is H.

In any of the foregoing embodiments, $R^{3'}$ is $C_1$-$C_8$ alkyl, hydroxy, hydroxyalkyl, $C_1$-$C_8$ alkoxy, halo, $C_1$-$C_8$ haloalkyl, $C_1$-$C_8$ haloalkoxy, —CN, —$NH_2$, or —$CO_2R^{4'}$.

In any of the foregoing embodiments, n' is 0 or 1 or 2.

In any of the embodiments above, the term "alkyl" implies a straight-chain or branched alkyl substituent containing from, for example, from about 1 to about 8 carbon atoms, e.g., from about 1 to about 6 carbon atoms. Examples of alkyl group include methyl, ethyl, n-propyl, isopropyl, n-butyl, sec-butyl, isobutyl, tert-butyl, n-pentyl, isopentyl, n-hexyl, and the like.

The above definition of "alkyl" also applies wherever "alkyl" occurs as part of a group, such as, e.g., in $C_3$-$C_6$ cycloalkylalkyl, hydroxyalkyl, haloalkyl (e.g., monohaloalkyl, dihaloalkyl, and trihaloalkyl), cyanoalkyl, aminoalkyl, alkylamino, dialkylamino, arylalkyl, etc. The alkyl can be substituted or unsubstituted, as described herein. Even in instances in which the alkyl is an alkylene chain (e.g., —$(CH_2)_n$—), the alkyl group can be substituted or unsubstituted.

In any of the embodiments above, the term "alkenyl," as used herein, means a linear alkenyl substituent containing from, for example, about 2 to about 8 carbon atoms (branched alkenyls are about 3 to about 8 carbons atoms), e.g., from about 3 to about 6 carbon atoms (branched alkenyls are about 3 to about 6 carbons atoms). In accordance with an embodiment, the alkenyl group is a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. The alkenyl can be substituted or unsubstituted, as described herein.

In any of the embodiments above, the term "alkynyl," as used herein, means a linear alkynyl substituent containing at least one carbon-carbon triple bond and from, for example, about 2 to about 8 carbon atoms (branched alkynyls are about 4 to about 12 carbons atoms), e.g., from about 2 to about 6 carbon atoms (branched alkynyls can be from about 4 to about 8 carbon atoms), e.g., from about 2 to about 4 carbon atoms. Examples of such substituents include propynyl, propargyl, n-butynyl, pentynyl, isopentynyl, hexynyl, octynyl, and the like. The alkynyl can be substituted or unsubstituted, as described herein.

In any of the embodiments above, the term "cycloalkyl," as used herein, means a cyclic alkyl moiety containing from, for example, 3 to 6 carbon atoms or from 5 to 6 carbon atoms. Examples of such moieties include cyclopropyl, cyclobutyl, cyclopentyl, cyclohexyl, and the like. The cycloalkyl can be substituted or unsubstituted, as described herein.

In any of the embodiments above, the term "hydroxy" refers to the group —OH.

In any of the embodiments above, the terms "alkoxy" and "cycloalkyloxy" embrace linear or branched alkyl and cycloalkyl groups, respectively, that are attached to a divalent oxygen. The alkyl and cycloalkyl groups are the same as described herein. The term "aryloxy" refers to substituents that have an aryl group attached to divalent oxygen. The aryl group is the same as described herein.

In any of the embodiments above, the term "halo" refers to a halogen selected from fluorine, chlorine, bromine, and iodine.

In any of the embodiments above, the term "aryl" refers to a mono-, bi-, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise $4n+2$ $\pi$ electrons, according to Hückel's Rule, wherein $n=1$, 2, or 3. The aryl can be substituted or unsubstituted, as described herein.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms can optionally be oxidized, and the nitrogen atoms can optionally be quaternized. Heteroaryl groups which are bicyclic or tricyclic must include at least one fully aromatic ring but the other fused ring or rings may be aromatic or non-aromatic. The heteroaryl group can be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furanyl, benzofuranyl, pyrrolyl, thienyl, isothiazolyl, thiazolyl, isoxazolyl, and oxadiazolyl. The heteroaryl can be substituted or unsubstituted, as described herein.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. In an aspect, a heterocycloalkyl is a 5, 6, or 7-membered monocyclic ring and contains one, two, or three heteroatoms selected from nitrogen, oxygen, and sulfur. The heterocycloalkyl can be attached to the parent structure through a carbon atom or through any heteroatom of the heterocycloalkyl that results in a stable structure. Examples of such heterocycloalkyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl. The heterocycloalkyl can be substituted or unsubstituted, as described herein.

In other aspects, any substituent that is not hydrogen (e.g., $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, aryl, arylalkyl, heteroaryl, heteroarylalkyl, heterocycloalkyl, or heterocycloalkylalkyl) can be an optionally substituted moiety. The substituted moiety typically comprises at least one substituent (e.g., 1, 2, 3, 4, 5, 6, etc.) in any suitable position (e.g., 1-, 2-, 3-, 4-, 5-, or 6-position, etc.). When an aryl group is substituted with a substituent, e.g., halo, amino, alkyl, OH, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention. Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocycloalkyl, as described herein.

In any of the embodiments above, whenever a range of the number of atoms in a structure is indicated (e.g., a $C_{1-8}$, $C_{1-6}$, or $C_{1-4}$ alkyl, cycloalkyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, cycloalkyl, etc.) referenced herein encompasses and specifically describes 1, 2, 3, 4, 5, 6, 7, and/or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, etc., as appropriate).

The subscript "n" represents the number of substituents, e.g., $R^3$, in which each substituent, e.g., $R^3$, can be the same or different. The subscripts "m," "o," and "q" represent the number of methylene repeat units. The subscript "p" represents the number of repeat units of a linker unit. The subscripts m, n, and q can be the same or different and each is either 0 or an integer from 1-5 (i.e., 1, 2, 3, 4, or 5). The subscript o is an integer from 1-5 (i.e., 1, 2, 3, 4, or 5). The subscript p is either 0 or an integer from 1-36 (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36). When m, n, p, or q is 0, then the corresponding moiety, i.e., methylene group, repeat unit, or $R^3$, is not present in the compound of formula (I) or (II).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, nonaqueous media such as ether, ethyl acetate, ethanol, isopropanol, or acetonitrile are typical. Lists of suitable salts are found in Remington's Pharmaceutical Sciences, 18th ed., Mack Publishing Company, Easton, Pa., 1990, p. 1445, and Journal of Pharmaceutical Science, 66, 2-19 (1977). For example, they can be a salt of an alkali metal (e.g., sodium or potassium), alkaline earth metal (e.g., calcium), or ammonium of salt.

A compound of formula (I) or (II) can be prepared by any suitable method, including the methods described herein. For example, a compound of formula (I) can be prepared by coupling a dioxaborolane derivative of 3-amino-5-bromobenzoic acid with 4-(4-bromophenyl)piperidine. A specific example of this method is set forth in FIG. 2, in which triazolyl derivatives 24a-n were synthesized starting from 3-amino-5-bromobenzoic acid 12 and 4-(4-bromophenyl)piperidin-4-ol 16. The carboxylic group of 12 was first converted to the methyl ester 13, and then the amine function was protected to give Boc-derivative 14a. A di-Boc side product 14b accompanied the product that was initially isolated, and this impurity reverted to the desired mono-Boc product 14a upon heating the mixture in refluxing MeOH in the presence of dilute $K_2CO_3$. The palladium-catalyzed condensation of arylbromide 14a with bis(pinacolato)-diboron under basic conditions afforded dioxaborolane 15. The acid-catalyzed dehydration of 16 yielded derivative 17, which was reduced to provide compound 18. Derivative 19 was obtained by coupling 18 with compound 15 under Suzuki conditions (Suzuki et al., Angew. Chem. Int. Ed. 2011, 50 (30), 6722-6737). The conversion of the amino group of 19 to a trifluoroacetamide derivative 20 was accomplished by using trifluoroacetic anhydride in the presence of base. After removing the N-Boc protecting group of 20 to give compound 21, aryl azide 22 was formed from an arenediazonium tosylate that was generated in situ and subsequent addition of sodium azide (Kutonova et al., Synthesis 2013, 45 (19), 2706-2710). In particular, the 1,2,3-triazolyl derivative 23b was synthesized via a click reaction involving aryl azide 22, 4-(trifluoromethyl)phenylacetylene 6b, Cu(II) salt and sodium ascorbate (Himo et al., J. Am. Chem. Soc. 2005, 127 (1), 210-216), followed by the one-pot hydrolysis of the trifluoroacetamide and the ester in the presence of potassium hydroxide to yield 24b.

The present invention further provides a dendron conjugate, in which at least one compound of formula (I) or (II) is linked to a dendron through the nitrogen atom on the piperidinyl group instead of $R^2$ or $R^{2'}$. In some instances, the dendron is attached to one compound of formula (I) or (II), whereas in other instances, the dendron is attached to more than one compound of formula (I) or (II). The dendron conjugate can optionally be attached to a particle as described herein.

In some embodiments, the dendron conjugate has a structure of formula (III)

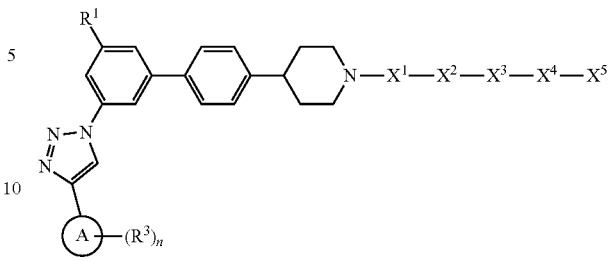

(III)

or a pharmaceutically acceptable salt thereof, wherein ring A is aryl, heteroaryl, or cycloalkyl;

$R^1$ is $-CO_2H$, $-CO_2(C_1-C_8$ alkyl), or an isostere of carboxylate;

each $R^3$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy, $C_3-C_6$ cycloalkyloxy, aryloxy, halo, $C_1-C_8$ haloalkyl, $C_1-C_8$ haloalkoxy, $-CN$, $-NO_2$, $-NR^5R^6$, $-C(O)R^4$, $-CO_2R^4$, $-C(O)NR^5R^6$, $-NR^5C(O)R^4$, $-(CH_2)_m$aryl, $-(CH_2)_m$heteroaryl, or $-(CH_2)_m$heterocycloalkyl;

$R^4$, $R^5$, and $R^6$ are the same or different and each is H or $C_1-C_8$ alkyl;

$X^1$ is selected from the group consisting of $-(CH_2)_o-$, $-C(O)-$, $-C(O)NH-$, $-OC(O)NH-$, $-OC(O)-$, $-C(O)O-$, $-C(S)NH-$, and $-SO_2-$;

$X^2$ is selected from the group consisting of

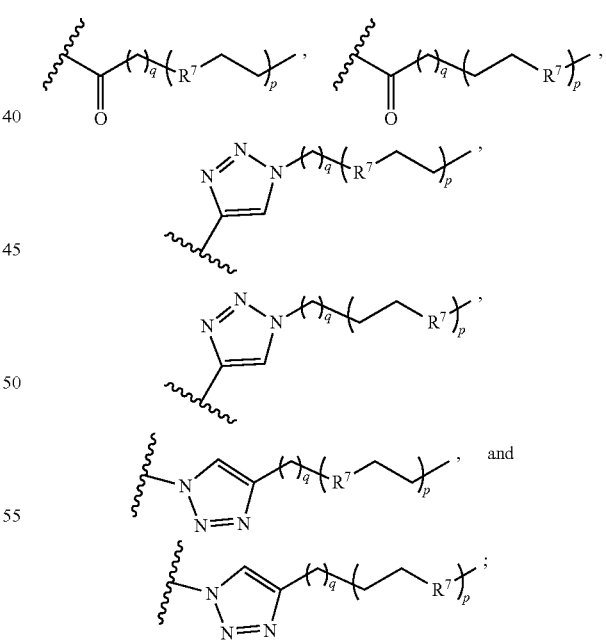

$R^7$ is $CH_2$, NH, or O;

$X^3$ is a dendron;

$X^4$ is selected from the group consisting of $-(CH_2)_o-$, $-C(O)-$, $-C(O)NH-$, $-OC(O)NH-$, $-OC(O)-$, $-C(O)O-$, $-C(S)NH-$, $-SO_2-$, $-NHC(O)-$, and

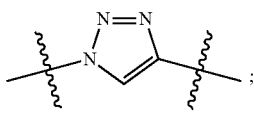 [SMILES: *c1cn(*)nn1]

$X^5$ is a reactive sulfur-containing moiety;

m, n, and q are the same or different and each is 0 or an integer from 1-5;

o is an integer from 1-5; and p is 0 or an integer from 1-36;

wherein $X^5$ is optionally linked to a particle.

In other embodiments, the dendron conjugate has a structure of formula (IV)

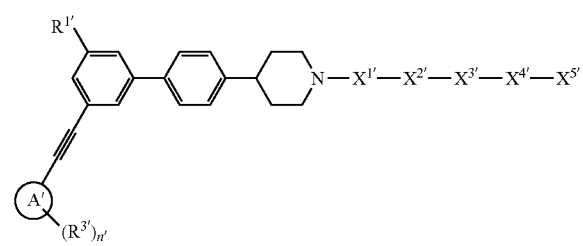

or a pharmaceutically acceptable salt thereof, wherein ring A' is aryl, heteroaryl, or cycloalkyl;

$R^{1'}$ is —$CO_2H$, —$CO_2(C_1-C_8$ alkyl), or a bioisostere of carboxylate;

$R^{2'}$ is H, $C_1-C_8$ alkyl, $C_2-C_8$ alkenyl, $C_2-C_8$ alkynyl, $C_3-C_6$ cycloalkyl, $C_3-C_6$ cycloalkylalkyl, hydroxyalkyl, $C_1-C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl;

each $R^{3'}$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy, $C_3-C_6$ cycloalkyloxy, aryloxy, halo, $C_1-C_8$ haloalkyl, $C_1-C_8$ haloalkoxy, —CN, —$NO_2$, —$NR^5R^{6'}$, —$C(O)R^{4'}$, —$CO_2R^{4'}$, —$C(O)NR^5R^{6'}$, —$NR^5C(O)R^{4'}$, —$(CH_2)_m$aryl, —$(CH_2)_m$heteroaryl, or —$(CH_2)_m$heterocycloalkyl;

$R^{4'}$, $R^{5'}$, and $R^{6'}$ are the same or different and each is H or $C_1-C_8$ alkyl;

$X^{1'}$ is selected from the group consisting of —$(CH_2)_{o'}$—, —C(O)—, —C(O)NH—, —OC(O)NH—, —OC(O)—, —C(O)O—, —C(S)NH—, and —$SO_2$—;

$X^{2'}$ is selected from the group consisting of

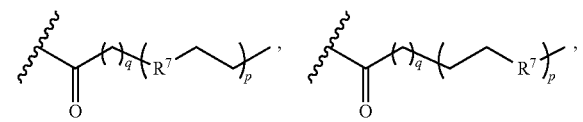

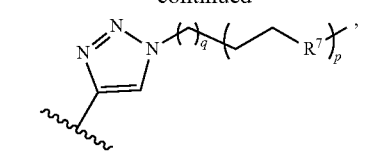

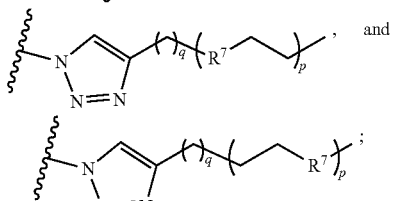

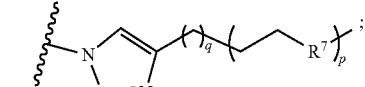

$R^7$ is $CH_2$, NH, or O;

$X^{3'}$ is a dendron;

$X^{4'}$ is selected from the group consisting of —$(CH_2)_{o'}$—, —C(O)—, —C(O)NH—, —OC(O)NH—, —OC(O)—, —C(O)O—, —C(S)NH—, —$SO_2$—, —NHC(O)—, and;

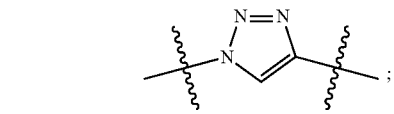 [SMILES: *c1cn(*)nn1]

$X^{5'}$ is a reactive sulfur-containing moiety;

m', n', and q' are the same or different and each is 0 or an integer from 1-5;

o' is an integer from 1-5; and p' is 0 or an integer from 1-36;

wherein $X^{5'}$ is optionally linked to a particle.

In certain dendron conjugates of formula (III) or (IV), ring A or ring A' is phenyl, furanyl, thiazolyl, thienyl, pyrazolyl, pyridazinyl, pyridinyl, pyrazinyl, benzofuranyl, cyclopropyl, or cyclohexyl. In a preferred embodiment, ring A or ring A' is phenyl.

In some embodiments of formula (III) or (IV), $R^1$ or $R^{1'}$ is —$CO_2H$. In other embodiments, $R^1$ or $R^{1'}$ is any suitable bioisostere of carboxylate, particularly a bioisostere that improves at least one property of conjugate, such as improves bioavailability and/or increases the binding affinity of the conjugate to $P2Y_{14}R$. Examples of a suitable bioisostere of carboxylate include

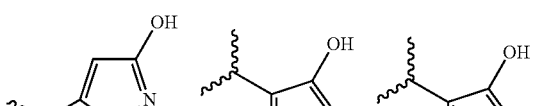

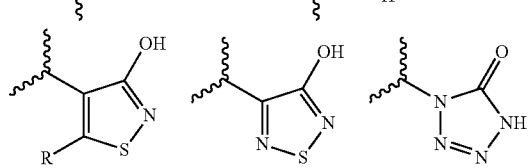

-continued

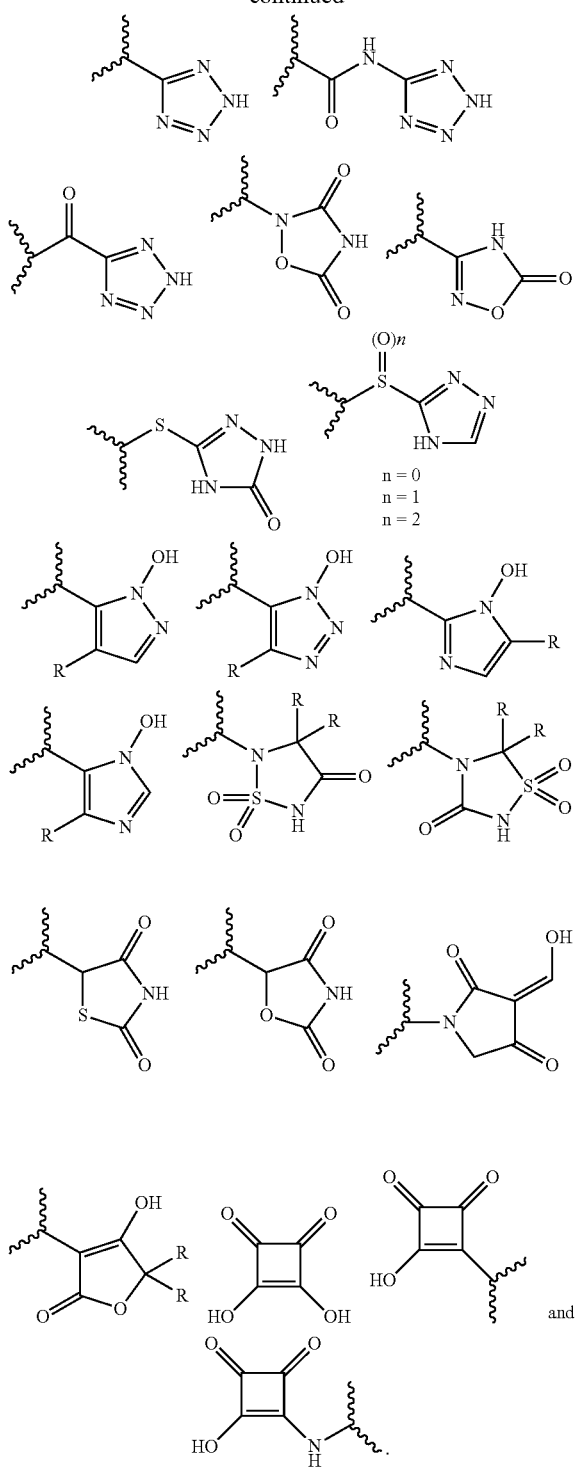

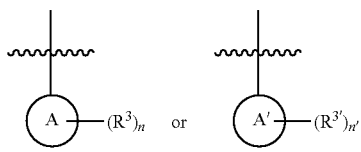

is selected from the group consisting of

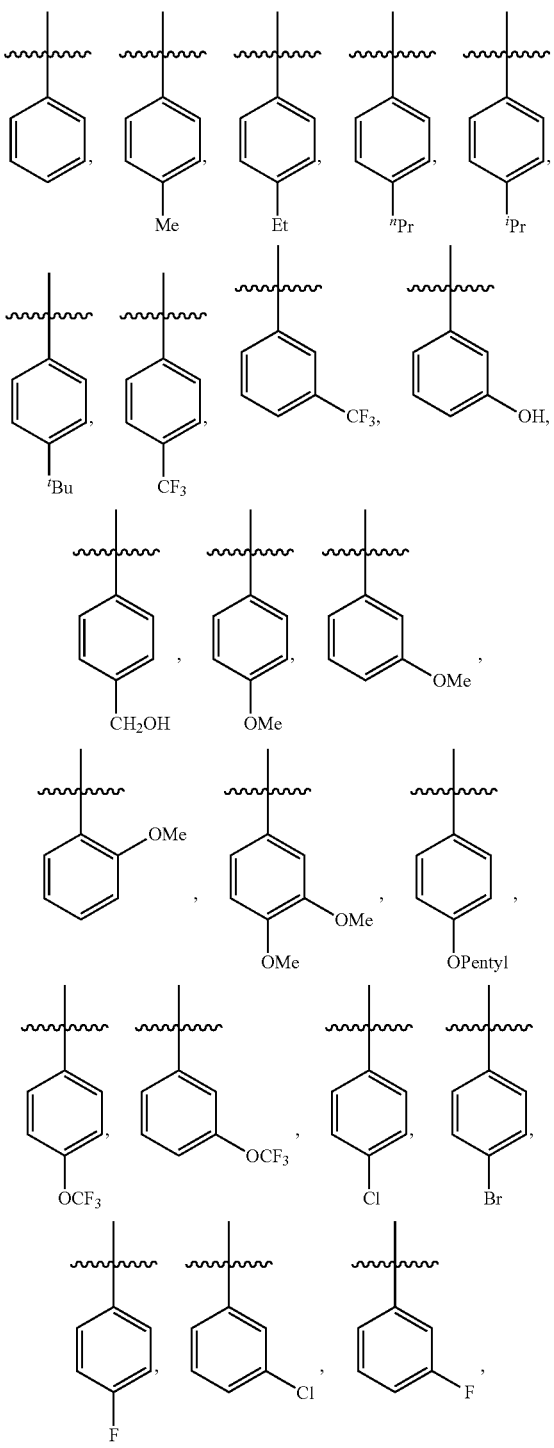

In any of the foregoing embodiments of formula (III) or (IV), $R^3$ or $R^{3'}$ is $C_1$-$C_8$ alkyl, hydroxy, hydroxyalkyl, $C_1$-$C_8$ alkoxy, halo, $C_1$-$C_8$ haloalkyl, $C_1$-$C_8$ haloalkoxy, —CN, —NH$_2$, or —CO$_2$R$^4$.

In any of the foregoing embodiments of formula (III) or (IV), n or n' is 0 or 1 or 2.

In some embodiments of the compound of formula (III) or (IV), $R^1$ or $R^{1'}$ is —CO$_2$H; and

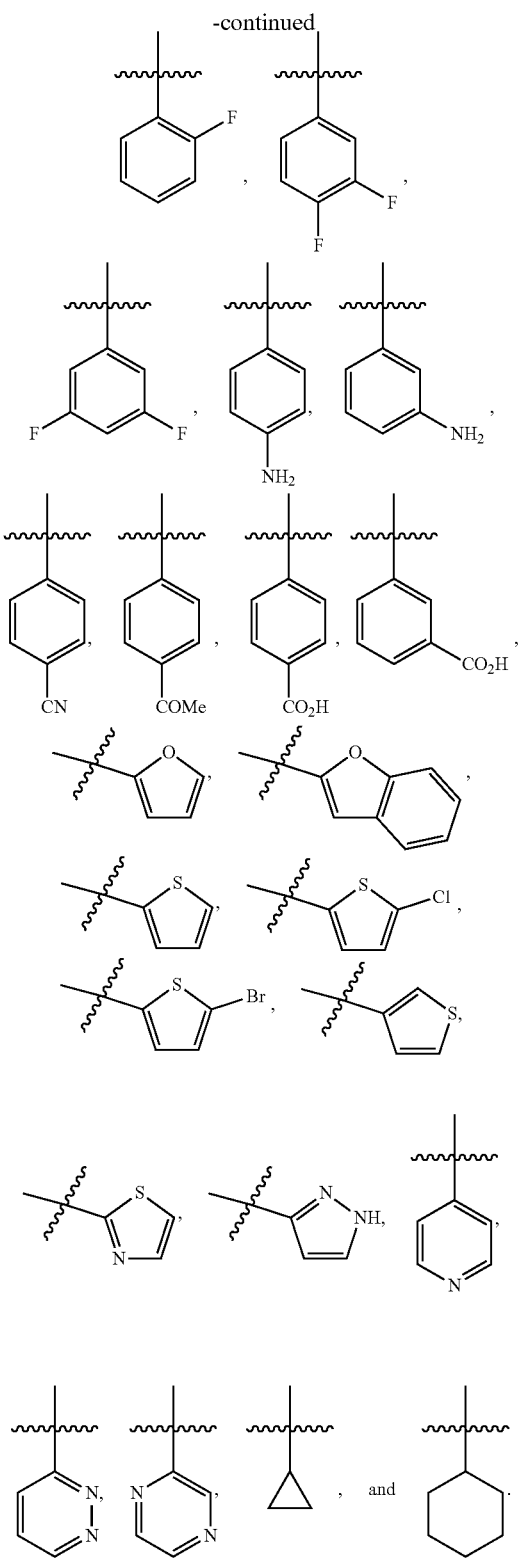

control of component functional groups—and their physical properties—by chemical synthesis, feasibility to conjugate multiple functional units at the peripheries and interiors, and a low enzymatic degradation rate. A dendron is similar to a dendrimer but without the symmetrical structure due to a reactive functional group close to the core of the dendron. In general, the reactive functional group can be, for example, amino, hydroxyl, thiol, sulfone (e.g., —RSO$_2$R'), sulfinic acid (e.g., —RSO(OH)), sulfonic acid (e.g., —RSO$_2$(OH)), thiocyanato, allyl, acetylenyl, carboxyl, halocarboxy (e.g., —OC(O)X), halo, formyl, haloformyl (e.g., —RC(O)X), carbonato, ester, alkoxy, amido (e.g., —C(O)NRR' or —NRC(O)R'), azido, azo, cyano, nitro, nitroso, or a combination thereof. In a preferred embodiment, the reactive functional group on the dendron available for conjugation to the compound of formula (I) or (II) is an amino group. The dendron can be anionic or cationic.

The dendron can be of any suitable generation, e.g., from G2 to G10 or more, including fractional generations, particularly G2 to G8, e.g., G2, G2.5, G3, G3.5, G4, G4.5, G5, G5.5, G6, G6.5, G7, or G7.5. For example, the half generations are carboxyl terminated and full generations are amine terminated. In preferred embodiments, the dendron is of G1, G2, or G3.

The conjugate of the invention can include any suitable dendron that can form a bond to the nitrogen on the piperidine ring of the compound of formula (I) or (II). In particular, the dendron can be a poly(amidoamine) (PAMAM) dendron, carboxyethylpolyamido (CEPAM) dendron, 2,2-bis(hydroxyl-methyl)propionic acid (bis-MPA) dendron, poly(propyleneimine) (PPI) dendron, poly-L-lysine dendron, poly(etherhydroxylamine) (PEHAM) dendron, poly(esteramine) (PEA) dendron, polyglycerol dendron, and combinations thereof (e.g., PEHAM/PEA dendron). If desired, the dendron can be further functionalized to improve at least one physicochemical property such as, e.g., water solubility. For example, a biologically inactive pendant PEGylated chain can be added to at least one suitable position of the dendron. The pendant PEGylated chain can have the formula

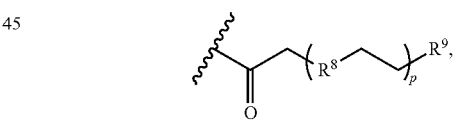

in which R$^8$ is CH$_2$, NH, or O; R$^9$ is —NH$_2$ or —CO$_2$H; and p is 0 or an integer from 1-36.

In some preferred aspects, the dendron is a CEPAM dendron that is optionally functionalized in at least one position to include the moiety

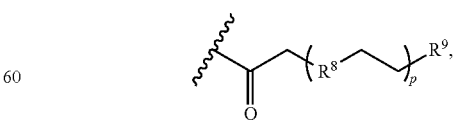

in which R$^8$ is CH$_2$, NH, or O; R$^9$ is —NH$_2$ or —CO$_2$H; and p is 0 or an integer from 1-36. For example, the CEPAM dendrons can be formed by units of 4-amino-4-(2-carboxyethyl)heptanedioic acid, with the following structures:

Dendrimers are classified as polymers; however, they are made from branched monomers through the iterative organic synthesis by adding one layer (i.e., generation) at each step to provide a symmetrical structure. The solution conformation of higher generation dendrimers can closely mimic the size and shape of a protein. Furthermore, dendrimers generally possess favorable characteristics: structural integrity,

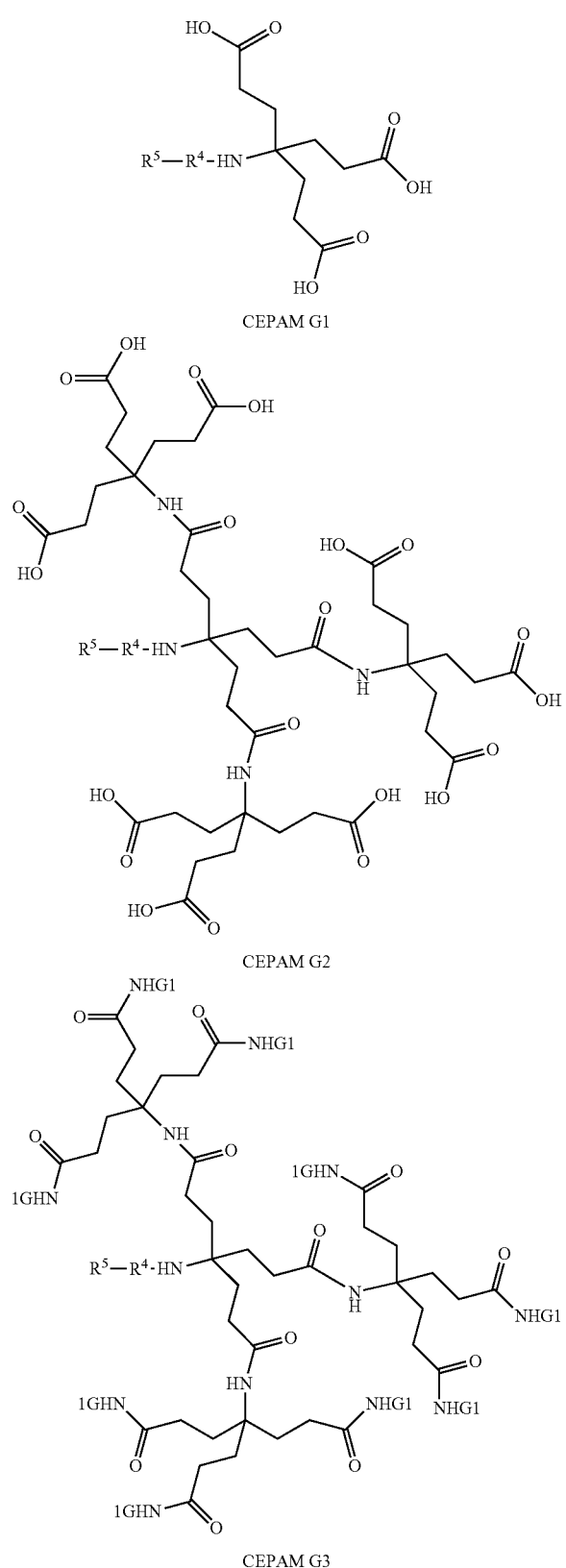

CEPAM G1

CEPAM G2

CEPAM G3

The conjugate is optionally linked to a particle through a sulfur atom of $X^5$ or $X^{5'}$. Typically, the particle is any nanoparticle or microparticle that has a surface suitable for bonding to an organic moiety. For example, the particle can be a quantum dot, a non-metallic particle, or a metallic particle. The quantum dot can comprise, for example, a core of the formula MX, in which M is cadmium, zinc, mercury, aluminum, lead, tin, gallium, indium, thallium, magnesium, calcium, strontium, barium, copper, and mixtures or alloys thereof; and X is sulfur, selenium, tellurium, nitrogen, phosphorus, arsenic, antimony or mixtures thereof. Suitable examples of the quantum dot include lead sulfide, lead selenide, lead telluride, zinc cadmium, zinc selenide, zinc sulfide, zinc telluride, cadmium selenide, cadmium sulfide, indium arsenide, indium phosphide, thallium arsenide, thallium nitride, thallium phosphide, thallium antimonide, and alloys of the foregoing. The non-metallic particle can comprise, for example, silica, titania, alumina, germania, calcium carbonate, barium sulfate, or a combination thereof. The metallic particle can comprise, for example, gold, silver, platinum, palladium, ruthenium, copper, iron oxide, gallium selenide, indium selenide, lead selenide, cadmium sulfide, lead sulfide, or a combination thereof. The size of the particle is not particularly important but can range from 1 nm to 1,000 μm (e.g., 1 nm to 10 nm, 10 nm to 100 nm, 50 nm to 100 nm, 100 nm to 1 μm, 1 μm to 50 μm, 50 μm to 250 μm, 250 μm to 500 μm, 500 μm to 750 μm, 500 μm to 1,000 μm). Any two of the foregoing endpoints can be used in combination to define a close-ended range.

In order to bond to the particle, $X^5$ or $X^{5'}$ is an organic group that includes a reactive sulfur-containing moiety. $X^5$ or $X^{5'}$ can be, for example, a bifunctional linker. Bifunctional linkers are known in the art (e.g., Sigma-Aldrich, St. Louis, Mo.). The bifunctional linker comprises any moiety that can form a chemical bond between the particle and $X^4$ or $X^{4'}$. The linker can be of any suitable charge, length and/or rigidity, but preferably the bifunctional linker is derived from a compound comprising a sulfur-containing moiety (e.g., thio) and a second reactive group, such as an amino group, hydroxyl, thio, a halo group, a carboxyl group, aryl, heteroaryl, or heterocyclyl group, prior to reaction with the particle, $X^4$ or $X^{4'}$, and/or the dendron. Examples of a suitable heteroaryl include

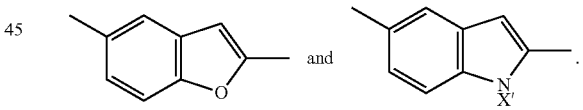

Preferably, these groups are at the terminal ends of the bifunctional linker. Examples of the linker include, e.g., 2-(boc-amino)ethanethiol, biphenyl-4,4'-dicarbodithioic acid, 4-mercapto-1-butanol, 6-mercapto-1-hexanol, [1,1'-biphenyl]-4,4'-dithiol, cysteine, and lipoic acid. In a preferred embodiment, $X^5$ or $X^{5'}$ is a residue of lipoic acid.

The methods described herein comprise using a compound of formula (I) or (II) or a conjugate or a pharmaceutically acceptable salt thereof in the form of a pharmaceutical composition. In particular, a pharmaceutical composition will comprise (i) at least one compound of formula (I) or (II) or a conjugate thereof, or a pharmaceutically acceptable salt thereof and (ii) a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I) or (II) or a pharmaceutically acceptable salt thereof can be administered orally to a subject in need thereof. Formulations suitable for oral administration can include (a) liquid solutions, such as an effective amount of the compound dissolved in diluents, such as water, saline, or orange juice and include an additive, such as cyclodextrin (e.g., $\alpha$-, $\beta$-, or $\gamma$-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or (II) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitors may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I) or (II) or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the mammal, particularly a human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by a person of skill in the art that various conditions or disease states may require prolonged treatment involving multiple administrations.

The inventive methods comprise administering an effective amount of a compound of formula (I) or (II) or a pharmaceutically acceptable salt thereof. An "effective amount" means an amount sufficient to show a meaningful benefit in an individual, e.g., reducing inflammation, reducing the risk of developing a particular condition described herein, delaying the onset of a particular condition described herein. The meaningful benefit observed in the mammal can be to any suitable degree (10, 20, 30, 40, 50, 60, 70, 80, 90% or more). In some aspects, one or more symptoms of the disease to be treated are prevented, reduced, halted, or eliminated subsequent to administration of a compound of formula (I) or (II) or a pharmaceutically acceptable salt thereof, thereby effectively treating the disease to at least some degree.

Effective amounts may vary depending upon the biological effect desired in the individual, condition to be treated, and/or the specific characteristics of the compound of formula (I) or (II) or a pharmaceutically acceptable salt thereof and the individual. In this respect, any suitable dose of the compound of formula (I) or (II) or a pharmaceutically acceptable salt thereof can be administered to the mammal (e.g., human), according to the type of disorder to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or (II) or a pharmaceutically acceptable salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) or (II) or salt thereof comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg). Any two of the foregoing endpoints can be used in combination to define a close-ended range.

In an aspect, a compound formula (I) or (II) antagonizes $P2Y_{14}R$ activity in a cell. The method comprises administering a compound of formula (I) or (II) or a conjugate or a pharmaceutically acceptable salt thereof to a cell. The only requirement is that the cell expresses $P2Y_{14}R$ and can be from any suitable tissue (e.g., muscle tissue, nervous tissue, connective tissue, or epithelial tissue). The tissue can be from any organ, including the head, neck, eye, skin, mouth, throat, esophagus, chest, bone, lung, colon, sigmoid, rectum, stomach, prostate, breast, ovaries, kidney, liver, pancreas, brain, intestine (e.g., gastrointestinal), heart, or adrenals. The antagonism of $P2Y_{14}R$ can be measured by any method, including the assay described herein.

$P2Y_{14}R$ has been implicated in immune and inflammatory responses (Barrett et al., Mol Pharmacol, 2013, 84, 41-49). Moreover, $P2Y_{14}R$ has been found to play a role in the initiation of inflammation and insulin resistance in obesity (Xu et al., *J. Immunol.* 2012, 189(4), 1992-1999). Accordingly, without wishing to be bound by any theory, it is believed that antagonizing $P2Y_{14}R$ can be a viable pathway to treating disorders associated with inflammation. Accordingly, the present invention provides a method for treating a disorder responsive to antagonism of $P2Y_{14}R$, such as inflammation, diabetes (e.g., type 2 diabetes), insulin resistance, hyperglycemia, a lipid disorder, obesity, a condition associated with metabolic syndrome, or asthma, in a mammal in need thereof which comprises administering a therapeutically effective amount of a compound of formula (I) or (II) or a pharmaceutically acceptable salt thereof to the mammal. A condition associated with metabolic syndrome includes, e.g., obesity, dyslipidemia, hyperglycermia, decreased high density lipoprotein (HDL), elevated triglycerides, and elevated blood pressure.

For purposes of the present invention, the term "mammal" typically includes, but is not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the mammal is a human.

The invention is further illustrated by the following embodiments.

(1) A compound of formula (I):

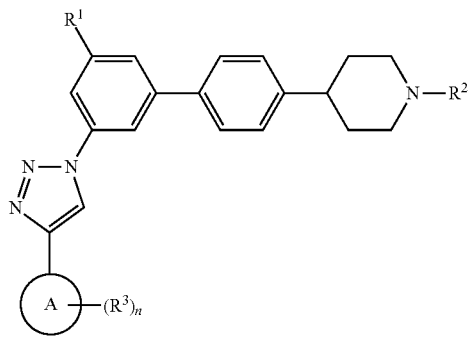

wherein
ring A is aryl, heteroaryl, or cycloalkyl;
$R^1$ is —$CO_2H$, —$CO_2(C_1$-$C_8$ alkyl), or an isostere of carboxylate;
$R^2$ is H, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyalkyl, $C_1$-$C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl; each $R^3$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —$NO_2$, —$NR^5R^6$, —$C(O)R^4$, —$CO_2R^4$, —$C(O)NR^5R^6$, —$NR^5C(O)R^4$, —$(CH_2)_m$aryl, —$(CH_2)_m$heteroaryl, or —$(CH_2)_m$heterocycloalkyl;
$R^4$, $R^5$, and $R^6$ are the same or different and each is H or $C_1$-$C_8$ alkyl;
m and n are the same or different and each is 0 or an integer from 1-5;
or a pharmaceutically acceptable salt thereof.

(2) The compound of embodiment (1), wherein ring A is phenyl, furanyl, thiazolyl, thienyl, pyrazolyl, pyridazinyl, pyridinyl, pyrazinyl, benzofuranyl, cyclopropyl, or cyclohexyl, or a pharmaceutically acceptable salt thereof.

(3) The compound of embodiment (2), wherein ring A is phenyl, or a pharmaceutically acceptable salt thereof.

(4) The compound of any one of embodiments (1)-(3), wherein $R^1$ is —$CO_2H$, or a pharmaceutically acceptable salt thereof.

(5) The compound of any one of embodiments (1)-(3), wherein $R^1$ is a bioisostere of carboxylate selected from the group consisting of

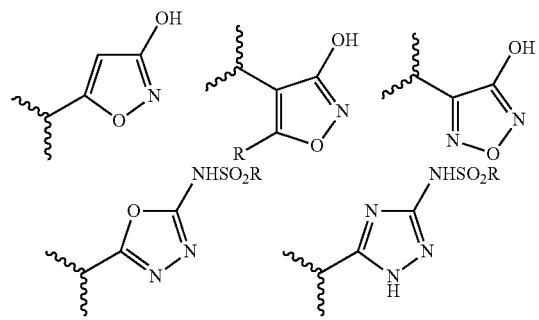

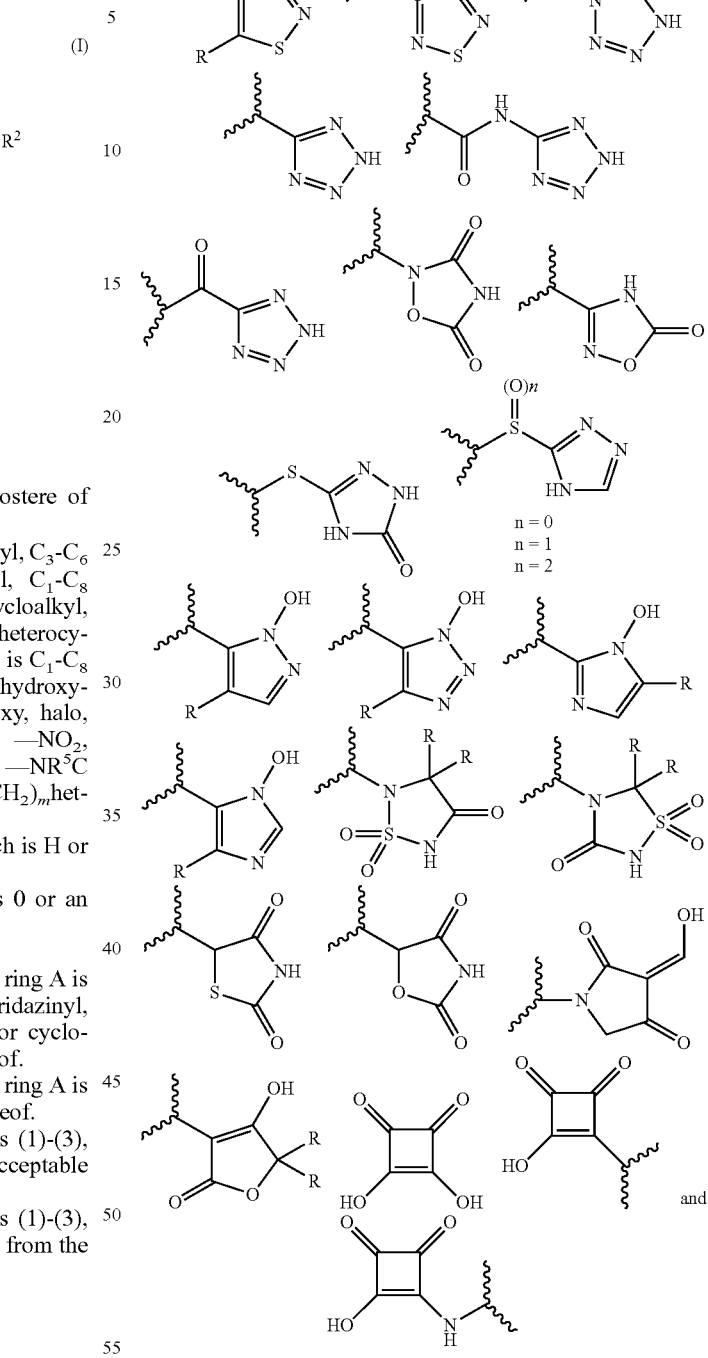

or a pharmaceutically acceptable salt thereof.

(6) The compound of any one of embodiments (1)-(5), wherein $R^2$ is H or $C_2$-$C_8$ alkynyl, or a pharmaceutically acceptable salt thereof.

(7) The compound of any one of embodiments (1)-(6), wherein $R^3$ is $C_1$-$C_8$ alkyl, hydroxy, hydroxyalkyl, $C_1$-$C_8$ alkoxy, halo, $C_1$-$C_8$ haloalkyl, $C_1$-$C_8$ haloalkoxy, —CN, —$NH_2$, or —$CO_2R^4$, or a pharmaceutically acceptable salt thereof.

(8) The compound of any one of embodiments (1)-(7), wherein n is 1 or 2.

(9) The compound of any one of embodiments (1)-(6), wherein n is 0.
(10) The compound of embodiment (1), wherein R$^1$ is —CO$_2$H; R$^2$ is H; and
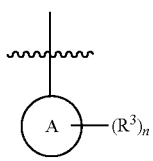
is selected from the group consisting of
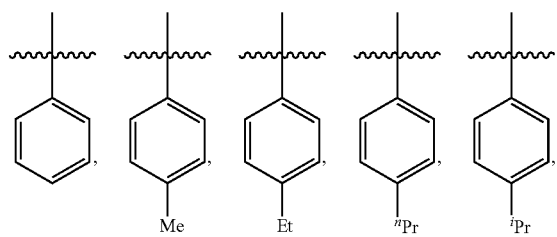
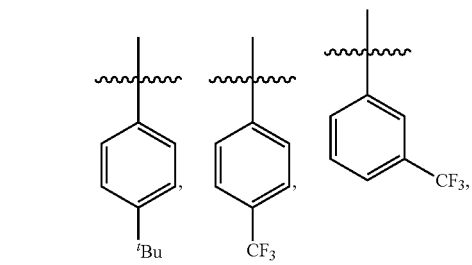
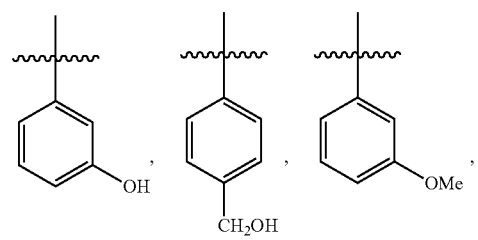
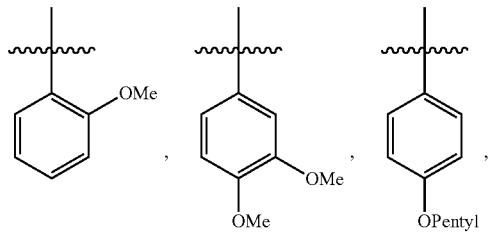
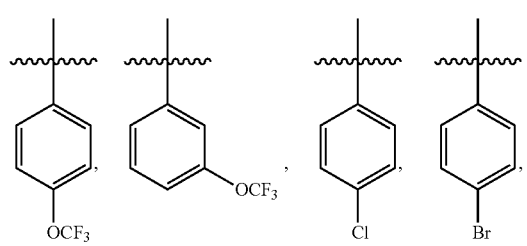
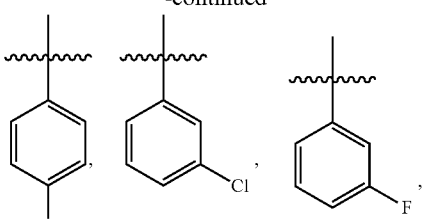
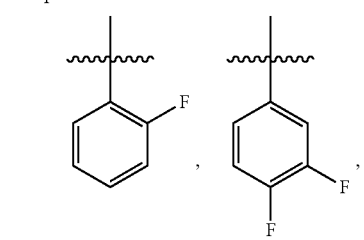
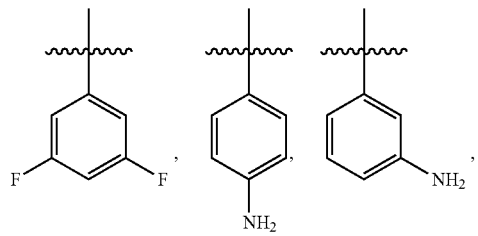
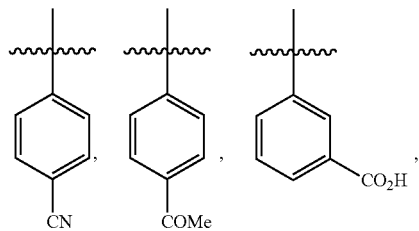
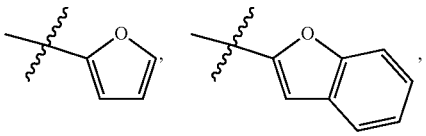
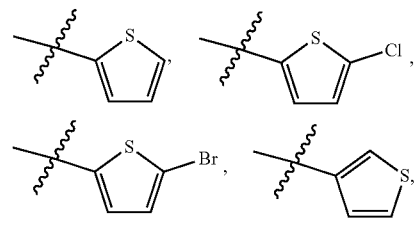
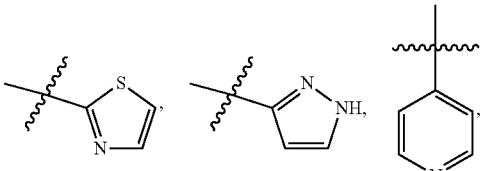
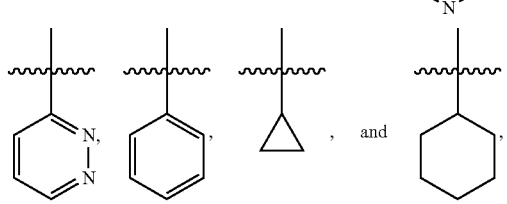
or a pharmaceutically acceptable salt thereof.

(11) A compound of formula (II):

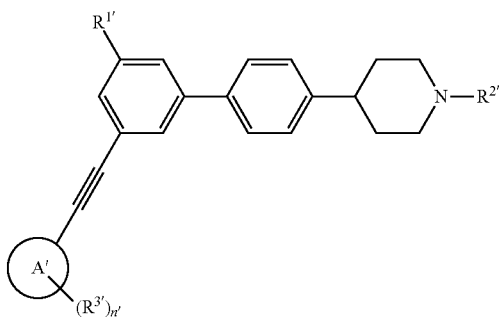

wherein
ring A' is aryl, heteroaryl, or cycloalkyl;
$R^{1'}$ is —$CO_2H$, —$CO_2(C_1-C_8$ alkyl), or a bioisostere of carboxylate;
$R^{2'}$ is H, $C_1-C_8$ alkyl, $C_2-C_8$ alkenyl, $C_2-C_8$ alkynyl, $C_3-C_6$ cycloalkyl, $C_3-C_6$ cycloalkylalkyl, hydroxyalkyl, $C_1-C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl;
each $R^{3'}$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy, $C_3-C_6$ cycloalkyloxy, aryloxy, halo, $C_1-C_8$ haloalkyl, $C_1-C_8$ haloalkoxy, —CN, —$NO_2$, —$NR^{5'}R^{6'}$, —$C(O)R^{4'}$, —$CO_2R^{4'}$, —$C(O)NR^{5'}R^{6'}$, —$NR^{5'}C(O)R^{4'}$, —$(CH_2)_m$aryl, —$(CH_2)_m$heteroaryl, or —$(CH_2)_m$heterocycloalkyl;
$R^{4'}$, $R^{5'}$, and $R^{6'}$ are the same or different and each is H or $C_1-C_8$ alkyl; and
m' and n' are the same or different and each is 0 or an integer from 1-5;
or a pharmaceutically acceptable salt thereof.

(12) A dendron conjugate comprising a compound of any one of embodiments (1)-(11), wherein the compound is linked to a dendron through the nitrogen atom on the piperidinyl group instead of $R^2$ or $R^{2'}$.

(13) The dendron conjugate of embodiment (12), wherein the dendron is attached to more than one compound of formula (I) or formula (II).

(14) A conjugate of formula (III)

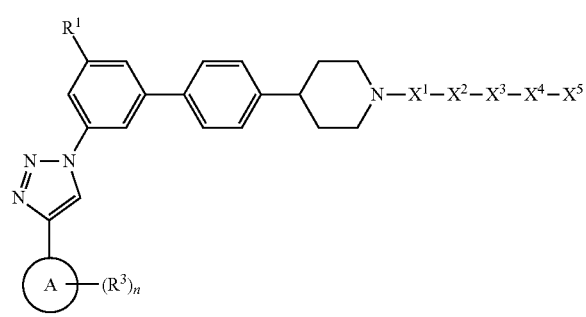

or a pharmaceutically acceptable salt thereof, wherein
ring A is aryl, heteroaryl, or cycloalkyl;
$R^1$ is —$CO_2H$, —$CO_2(C_1-C_8$ alkyl), or a bioisostere of carboxylate;

each $R^3$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy, $C_3-C_6$ cycloalkyloxy, aryloxy, halo, $C_1-C_8$ haloalkyl, $C_1-C_8$ haloalkoxy, —CN, —$NO_2$, —$NR^5R^6$, —$C(O)R^4$, —$CO_2R^4$, —$C(O)NR^5R^6$, —$NR^5C(O)R^4$, —$(CH_2)_m$aryl, —$(CH_2)_m$heteroaryl, or —$(CH_2)_m$heterocycloalkyl;
$R^4$, $R^5$, and $R^6$ are the same or different and each is H or $C_1-C_8$ alkyl;
$X^1$ is selected from the group consisting of —$(CH_2)_o$—, —C(O)—, —C(O)NH—, —OC(O)NH—, —OC(O)—, —C(O)O—, —C(S)NH—, and —$SO_2$—;
$X^2$ is selected from the group consisting of

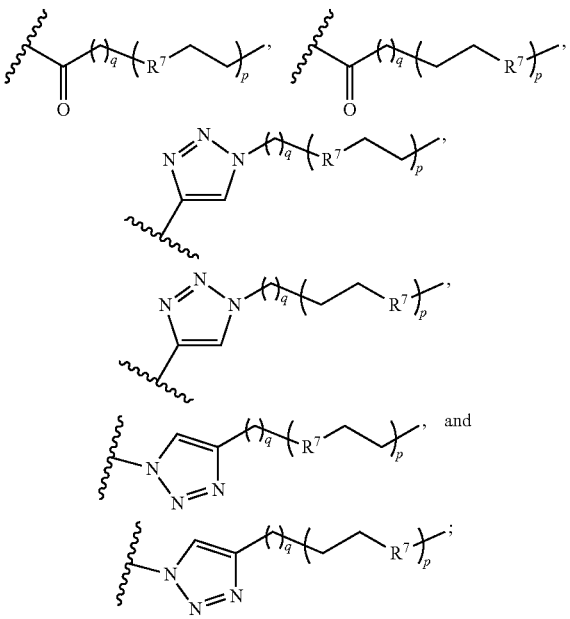

$R^7$ is $CH_2$, NH, or O;
$X^3$ is a dendron;
$X^4$ is selected from the group consisting of —$(CH_2)_o$—, —C(O)—, —C(O)NH—, —OC(O)NH—, —OC(O)—, —C(O)O—, —C(S)NH—, —$SO_2$—, —NHC(O)—, and

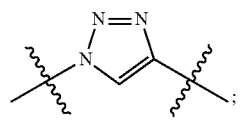 [SMILES: *c1cn(*)nn1]

$X^5$ is a reactive sulfur-containing moiety;
m, n, and q are the same or different and each is 0 or an integer from 1-5;
o is an integer from 1-5; and
p is 0 or an integer from 1-36;
wherein $X^5$ is optionally linked to a particle.

(15) The conjugate of embodiment (14), wherein the dendron is carboxyethylpolyamido (CEPAM) dendron that is optionally functionalized in at least one position to include the moiety

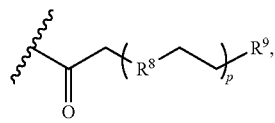

wherein $R^8$ is $CH_2$, NH, or O, and $R^9$ is —$NH_2$ or —$CO_2H$.

(16) The conjugate of embodiment (15), wherein the dendron is of generation G1, G2, or G3.

(17) The conjugate of any one of embodiments (14)-(16) that is linked to a particle through a sulfur atom of $X^5$.

(18) The conjugate of embodiment (17), wherein the particle is a quantum dot, a non-metallic particle, or a metallic particle.

(19) The conjugate of embodiment (18), wherein the metallic particle comprises gold, silver, platinum, ruthenium, iron oxide, gallium selenide, indium selenide, lead selenide, cadmium sulfide, lead sulfide, or a combination thereof.

(20) The conjugate of any one of embodiments (14)-(19), wherein $X^5$ comprises a residue of lipoic acid.

(21) A dendron conjugate of formula (IV)

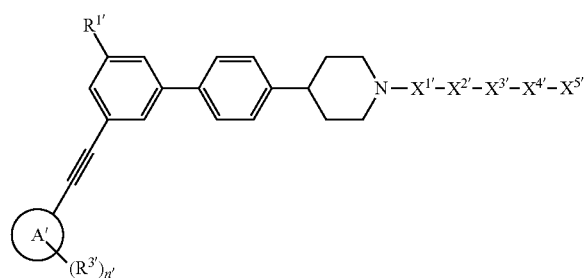

(IV)

or a pharmaceutically acceptable salt thereof, wherein
ring A' is aryl, heteroaryl, or cycloalkyl;
$R^{1'}$ is —$CO_2H$, —$CO_2(C_1$-$C_8$ alkyl), or a bioisostere of carboxylate;
$R^{2'}$ is H, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyalkyl, $C_1$-$C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl;
each $R^{3'}$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —$NO_2$, —$NR^{5'}R^{6'}$, —$C(O)R^{4'}$, —$CO_2R^{4'}$, —$C(O)NR^{5'}R^{6'}$, —$NR^{5'}C(O)R^{4'}$, —$(CH_2)_m$aryl, —$(CH_2)_m$heteroaryl, or —$(CH_2)_m$heterocycloalkyl;
$R^{4'}$, $R^{5'}$, and $R^{6'}$ are the same or different and each is H or $C_1$-$C_8$ alkyl;
$X^{1'}$ is selected from the group consisting of —$(CH_2)_{o'}$—, —C(O)—, —C(O)NH—, —OC(O)NH—, —OC(O)—, —C(O)O—, —C(S)NH—, and —$SO_2$—;
$X^{2'}$ is selected from the group consisting of

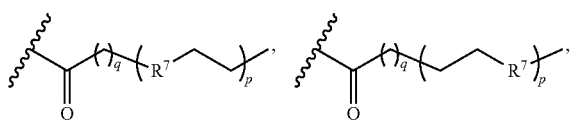

$R^{7'}$ is $CH_2$, NH, or O;
$X^{3'}$ is a dendron;
$X^{4'}$ is selected from the group consisting of —$(CH_2)_{o'}$—, —C(O)—, —C(O)NH—, —OC(O)NH—, —OC(O)—, —C(O)O—, —C(S)NH—, —$SO_2$—, —NHC(O)—, and $X^{5'}$ is a reactive sulfur-containing moiety;
m', n', and q' are the same or different and each is 0 or an integer from 1-5;
o' is an integer from 1-5; and
p' is 0 or an integer from 1-36;
wherein $X^{5'}$ is optionally linked to a particle.

(22) A pharmaceutical composition comprising (i) at least one compound of any one of embodiments (1)-(11), a conjugate of any one of embodiments (12)-(21), or a pharmaceutically acceptable salt thereof and (ii) a pharmaceutically acceptable carrier.

(23) A method of antagonizing P2Y$_{14}$ receptor (P2Y$_{14}$R) activity in a cell comprising administering a compound of any one of embodiments (1)-(11), a conjugate of any one of embodiments (12)-(21), or a pharmaceutically acceptable salt thereof to a cell, whereby activity of P2Y$_{14}$R is antagonized.

(24) A method for treating inflammation, diabetes, insulin resistance, hyperglycemia, a lipid disorder, obesity, a condition associated with metabolic syndrome, or asthma in a mammal in need thereof which comprises administering a therapeutically effective amount of a compound of any one of embodiments (1)-(11) or a pharmaceutically acceptable salt thereof to the mammal.

The following examples further illustrate the invention but, of course, should not be construed as in any way limiting its scope.

EXAMPLES

The proton and carbon nuclear magnetic resonance spectra were recorded using a Bruker 400 MHz NMR spectrometer. Purification of final compounds was performed by preparative high performance liquid chromatography (HPLC) (Column: Luna 5 μm C18(2) 100 Å, LC Column 250×4.6 mm). Method A Eluent: 0.1% trifluoroacetic acid (TFA) in water-CH$_3$CN from 100:0 to 70:30 in 45 min with a flow rate of 5 mL/min. Method B: Method B Eluent: 10 mM triethylammonium acetate (TEAA) buffer —CH$_3$CN from 80:20 to 20:80 in 40 min, then 10 mM TEAA buffer —CH$_3$CN from 20:80 to 0:100 in 10 min with a flow rate of 5 mL/min. Purities of all tested compounds were ≥95%, as estimated by analytical HPLC (Column: ZORBAX™ Eclipse 5 μm XDB-C18 analytical column, 150×4.6 mm; Agilent Technologies, Inc., Santa Clara, Calif.). Peaks were detected by UV absorption (254 nm) using a diode array detector. All derivatives tested for biological activity showed >95% purity in the HPLC systems. Analytical thin-layer chromatography was carried out on SIGMA-ALDRICH™ thin layer chromatography (TLC) plates and compounds were visualized with UV light at 254 nm. Silica gel flash chromatography was performed using 230-400 mesh silica gel. Unless noted otherwise, reagents and solvents were purchased from Sigma-Aldrich (St. Louis, Mo.). Low-resolution mass spectrometry was performed with a JEOL SX102 spectrometer (Peabody, Mass.) with 6-kV Xe atoms following desorption from a glycerol matrix or on an Agilent LC/MS 1100 MSD (Santa Clara, Calif.), with a Waters ATLANTIS™ C18 column (Milford, Mass.). High-resolution mass spectroscopic (HRMS) measurements were performed on a proteomics optimized WATERS™ MICROMASS™ Q-TOF-2™ using external calibration with polyalanine.

Example 1

Figure 2:
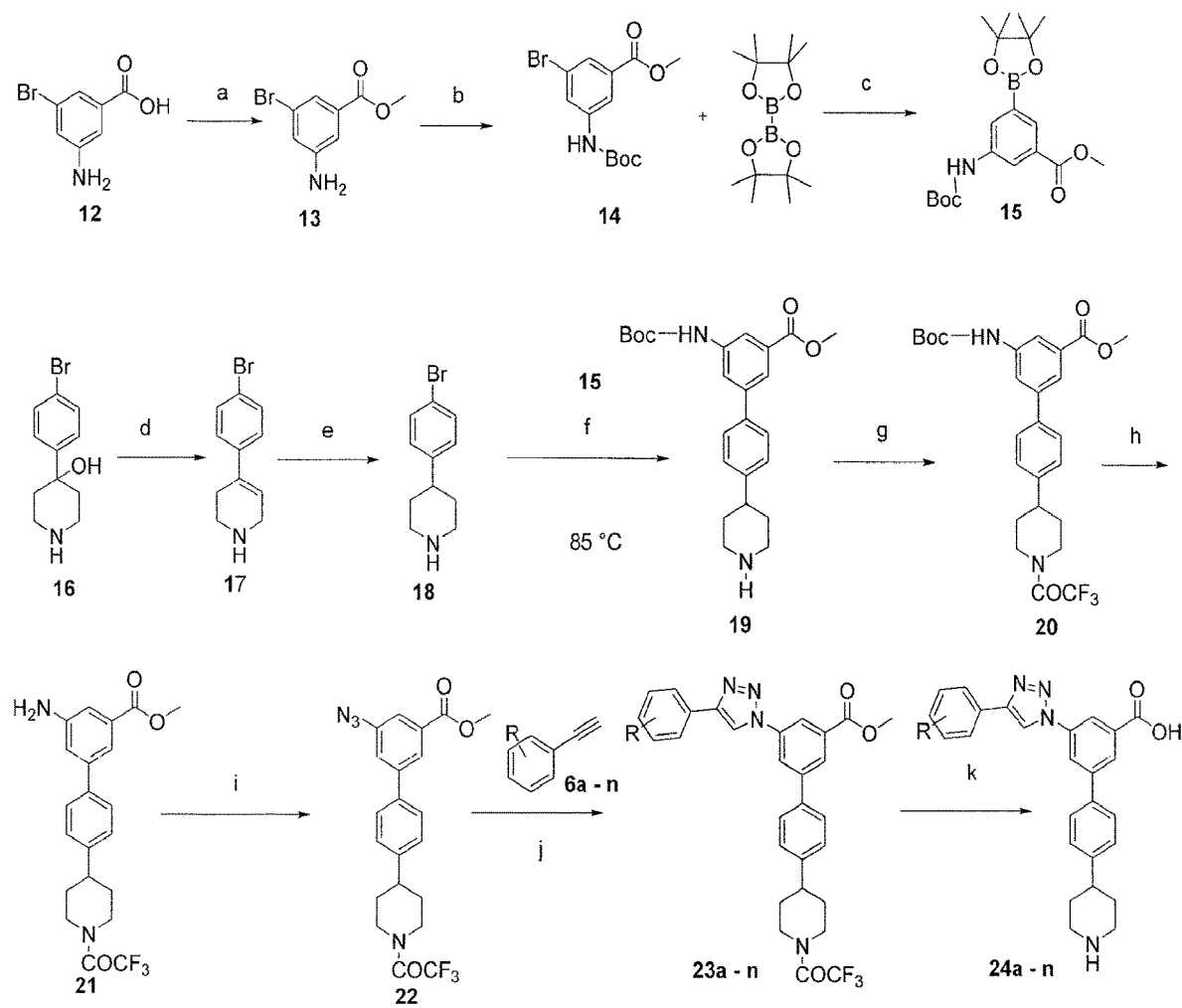
FIG. 2 is a chemical scheme of the synthesis of triazolyl derivatives of formula (I) (24a-n) as $P2Y_{14}R$ antagonists in accordance with an embodiment of the invention. Reagents and conditions: a. $CH_3OH$, $SOCl_2$, 0 to 23° C. (98%); b. 1) $Boc_2O$, $(C_2H_5)_3N$, DMAP, DCM; 2) $K_2CO_3$, MeOH, reflux (70%); c. $PdCl_2$(DPPF) (DPPF: 1,1'-bis(diphenylphosphino)ferrocene), AcOK, DMF, 95° C. (74%); d. TFA, 90° C. (97%); e. $H_2$, Rh/C, 100 psi (98%); f. $Pd(Ph_3P)_4$, $K_2CO_3$, DME, 85° C. (71%); g. $(CF_3CO)_2O$, $NEt_3$, $Et_2O$; h. TFA, DCM (70%); i. 1) Ts-OH, $NaNO_2$, $H_2O/ACN$; 2) $NaN_3$, (83%); j. $CuSO_4$, sodium ascorbate (1M aq.) k. KOH (1M aq.).

This example demonstrates the synthesis of the intermediate methyl 3-amino-5-bromobenzoate (13) in an embodiment of the invention (FIG. 2).

3-Bromo-5-aminobenzoic acid 12 (1.0 g, 4.62 mmol) was stirred in methanol (15 mL) with ice cooling, and the yellow solution was treated with thionyl chloride (4.00 mL, 55.0 mmol) dropwise over 20 min. The resulting mixture was allowed to warm up to room temperature and left stirring overnight. The reaction mixture was quenched with aqueous saturated NaHCO$_3$ solution at 0° C. The solvent was then removed under vacuum, and the residue was suspended in ethyl acetate (200 mL). The organic phase was washed with brine (100 mL), dried (Na$_2$SO$_4$) and concentrated to afford the title compound as a yellow solid (1.08 g, 98%). $^1$H NMR (400 MHz, Methanol-d) δ 7.10 (t, J=1.6 Hz, 1H), 6.83 (t, J=1.6 Hz, 1H), 6.57 (t, J=1.6 Hz, 1H), 3.46 (s, 3H). 13C NMR (100 MHz, CDCl$_3$) δ: 52.3, 114.6, 121.6, 122.3, 122.9, 132.6, 147.7, 166.0. m/z (ESI, MH$^+$) 231. ESI-HRMS (MH$^+$) calcd. for C$_8$H$_8$BrNO$_2$ 229.9817, found 229.9818. HPLC purity 98.8% (R$_t$=12.3 min).

Example 2

This example demonstrates the synthesis of the intermediate methyl 3-bromo-5-((tert-butoxycarbonyl)amino)benzoate (14) in an embodiment of the invention (FIG. 2).

To a solution of 13 (3.73 g, 16.2 mmol) in DCM (40 mL), Boc$_2$O (4.2 g, 19.4 mmol) and DMAP (1.9 g, 16.2 mmol) were sequentially added with ice cooling bath. The resulting mixture was allowed to stir at 0° C. for 2 h. The solvent was removed under vacuum, and the resulting residue was purified by silica gel chromatography using as eluant hexane/EtOAc (75:25) to afford the title compound as a white solid (4.3 g, 80%). $^1$H NMR (400 MHz, CDCl$_3$): δ 7.98 (s, 1H), 7.82 (s, 1H), 7.80 (s, 1H), 6.60 (s, 1H), 3.91 (s, 3H), 1.52 (s, 9H). $^{13}$C NMR (100 MHz, MeOD): δ 165.6, 153.3, 141.3, 132.1, 125.4, 124.7, 121.9, 117.5, 51.5, 27.2. MS (ESI, m/z) 331 [M+H]+; ESI-HRMS calcd. m/z for C$_{13}$H$_{16}$BrNO$_4$ 329.0263, found 329.0260 [M+H]$^+$. HPLC purity 99.6% (R$_t$=20.14 min).

Example 3

This example demonstrates the synthesis of the intermediate methyl 3-((tert-butoxycarbonyl)amino)-5-(4,4,5,5-tetramethyl-1,3,2-dioxaborolan-2-yl)benzoate (15) in an embodiment of the invention (FIG. 2).

A solution of 14 (1.36 g, 4.11 mmol), bis(pinacolato)diboron (1.25 g, 4.94 mmol), KOAc (1.21 g, 12.3 mmol) in dry DMF (12 mL) was degassed with N$_2$ for 30 min. Then, PdCl$_2$(DPPF) (DPPF: 1,1'-bis(diphenylphosphino)ferrocene) (0.30 g, 0.41 mmol) was added while continuing degassing for additional 5 min. The reaction mixture was heated at 95° C. and left stirring overnight. After cooling, the resulting mixture was suspended in EtOAc and filtered through CELITE™ (Sigma Aldrich, St. Louis, Mo.). The solvent was removed under vacuum leaving a black residue, which was purified by silica gel chromatography using as eluant hexane:EtOAc (75:25). The title compound was obtained as a white solid (1.1 g, 74%). $^1$H NMR (400 MHz, Chloroform-d) δ 8.16 (t, J=2.0 Hz, 1H), 8.14 (t, J=2.0 Hz, 1H), 7.90 (t, J=2.0 Hz, 1H), 6.53 (s, 1H), 3.90 (s, 3H), 1.52 (s, 9H), 1.34 (s, 12H). 13C NMR (100 MHz, CDCl$_3$) δ: 24.9, 28.3, 52.1, 84.1, 122.2, 128.9, 130.0, 138.2, 152.6, 166.9. m/z (ESI, MH$^+$) 378. ESI-HRMS (MH$^+$) calcd. for C$_{19}$H$_{28}$BNO$_6$ 376.2046, found 376.2049.

Example 4

This example demonstrates the synthesis of the intermediate 4-(4-bromophenyl)-1,2,3,6-tetrahydropyridine (17) in an embodiment of the invention (FIG. 2).

4-(4-Bromophenyl)piperidin-4-ol 16 (1.0 g, 3.90 mmol) was carefully added to CF$_3$COOH (2.99 mL, 39 mmol), and the resulting mixture was heated at 90° C. for 3 h. After cooling, the solvent was removed under vacuum to give the title product as a white solid (0.90 g, 97%). $^1$H NMR (400 MHz, Methanol-d$_4$) δ 7.54 (d, J=8.6 Hz, 2H), 7.41 (d, J=8.6 Hz, 2H), 6.34-6.00 (m, 1H), 3.85 (dd, J=2.7 Hz, 2H), 3.48 (t, J=6.1 Hz, 2H), 2.93-2.60 (m, 2H). 13C NMR (100 MHz, MeOD) δ: 23.3, 40.7, 42.0, 116.4, 121.7, 126.6, 131.4, 134.6, 138.1. m/z (ESI, MH$^+$) 239. ESI-HRMS (MH$^+$) calcd. for C$_{11}$H$_{12}$BrN 238.0231, found 238.0230.

Example 5

This example demonstrates the synthesis of the intermediate 4-(4-bromophenyl)piperidine (18) in an embodiment of the invention (FIG. 2).

To a solution of 4-(4-bromophenyl)-1,2,3,6-tetrahydropyridine 17 (0.90 g, 3.78 mmol) in dry MeOH (20 mL) and Et$_3$N (2 ml) was added Rh/C catalyst (0.060 g, J. Bishop & Co. Platinum). The resulting reaction mixture was stirred at room temperature in a hydrogen atmosphere (100 psi) for 24 h. The mixture was filtered through a cake of CELITE™ (Sigma Aldrich, St. Louis, Mo.), and the filtrate was concentrated to give the title compound as a white solid (0.91 g, 98%). TH NMR (400 MHz, MeOD) &: 1.55-1.59 (2H, m). 1.61-1.70 (2H, m), 2.55-2.56 (1H, m), 2.64-2.70 (2H, m), 3.09-3.06 (2H, m), 713 (2H, J=8.0, d), 7.31 (2H, J=8.0, d). $^{13}$C NMR (100 MHz, MeOD) δ: 32.7, 41.4, 45.6, 119.4, 126.4, 128.2, 128.5, 131.2, 145.3. m/z (EST, MH$^+$) 241.

Example 6

This example demonstrates the synthesis of the intermediate methyl 5-((tert-butoxycarbonyl)amino)-4'-(piperidin-4-yl)-[1,1'-biphenyl]-3-carboxylate (19) in an embodiment of the invention (FIG. 2).

A suspension of 15 (0.514 g, 01.3 mmol), K$_2$CO$_3$ (0.565 g, 4.0 mmol) in dry DME (10 mL) was stirred for 15 min. 18 (0.555 g, 1.9 mmol) was added and the yellow suspension was degassed with N$_2$ for 40 min. Then, Pd(Ph$_3$P)$_4$ (0.078 g, 0.068 mmol) was added to the resulting mixture while flushing N$_2$ for an additional 5 min. The reaction was heated at 85° C. for 7 h; after cooling the mixture was filtered through CELITE™ (Sigma Aldrich, St. Louis, Mo.), and the solvent was removed under vacuum. The residue was purified by silica gel chromatography using as eluant DCM: MeOH: Et$_3$N (9:1:0.1) to afford to the title compound as a white solid (0.548 g, 70%). $^1$H NMR (400 MHz, CDCl$_3$) δ:1.47 (9H, s), 1.85-1.90 (4H, m), 2.65-2.68 (1H, m), 2.78-2.83 (2H, m), 3.28-3.37 (2H, m), 3.85 (3H, s), 6.67 (1H, br s), 7.04-7.06 (1H, m), 7.24 (2H, J=8, d), 7.52 (2H, J=8, d), 7.84 (2H, m). $^{13}$C NMR (100 MHz, CDCl$_3$) δ: 28.4, 29.7, 33.8, 42.3, 42.7, 46.7, 52.2, 61.1, 118.0, 122.6, 126.2, 126.8, 127.3, 128.4, 128.6, 131.5 137.9, 139.3, 142.1, 146.0, 152.8, 166.9. m/z (ESI, MH$^+$) 411. ESI-HRMS (MH$^+$) calcd. for C$_{24}$H$_{30}$N$_2$O$_4$ 411.2284, found 411.2285.

Example 7

This example demonstrates the synthesis of the intermediate methyl 5-((tert-butoxycarbonyl)amino)-4'-(1-(2,2,2-trifluoroacetyl)piperidin-4-yl)-[1,1'-biphenyl]-3-carboxylate (20) in an embodiment of the invention (FIG. 2).

To a suspension of 19 (0.538 g, 1.3 mmol) in dry Et$_2$O (2.5 mL) at 0° C. and N$_2$ atmosphere, Et$_3$N (0.43 ml, 3.1 mmol) and TFAA (0.34 ml, 2.4 mmol) were added, and the resulting mixture was stirred for 1 h. The organic solvent was removed under vacuum and the resulting orange oil was used in the next step without any further purification. m/z (ESI, MH$^+$) 507. ESI-HRMS (MH$^+$) calcd. for C$_{26}$H$_{29}$F$_3$N$_2$O$_5$ 529.1926, found 529.1935.

Example 8

This example demonstrates the synthesis of the intermediate methyl 5-amino-4'-(1-(2,2,2-trifluoroacetyl)piperidin-4-yl)-[1,1'-biphenyl]-3-carboxylate (21) in an embodiment of the invention (FIG. 2).

To a solution of 20 (0.538 g, 1.06 mmol) in DCM (12 mL), TFA (2.44 ml, 31.8 mmol) was added and the resulting mixture was stirred overnight. A saturated solution of NaHCO$_3$ was gradually added to get neutral pH and the aqueous layer was extracted with DCM (3×30 mL). The collected organic fractions were dried over Na$_2$SO$_4$, filtered and the solvent was removed under vacuum. The residue was purified by silica gel chromatography using as eluant hexane/EtOAc (60:40) to give a yellow oil (0.371 g, 70%). (ESI, MH$^+$) 407. $^1$H NMR (400 MHz, Chloroform-d) δ 7.65 (t, J=1.5 Hz, 1H), 7.55 (d, J=8.3 Hz, 2H), 7.33 (t, J=1.5 Hz, 1H), 7.26 (d, J=8.2 Hz, 2H), 7.06 (t, J=1.5 Hz, 1H), 4.72 (dd, 1H), 4.16 (d, J=13.7 Hz, 1H), 3.91 (s, 3H), 3.27 (td, 1H), 3.01-2.72 (m, 2H), 2.02 (d, J=12.9 Hz, 2H), 1.75 (qd, J=4.0, 12.7 Hz, 2H). $^{13}$C NMR (100 MHz, CDCl$_3$) δ: 32.6, 33.6, 42.1, 44.2, 46.4, 52.1, 114.8, 117.8, 118.7, 120.3, 121.2, 122.7, 127.5 (t, J$_{C-F}$=41 Hz), 131.6, 138.9, 139.1 142.1, 143.7, 146.7, 167.1. (ESI, MH$^+$) 407. ESI-HRMS (MH$^+$) calcd. for C$_{21}$H$_{21}$F$_3$N$_2$O$_3$ 407.1583, found 407.1576.

Example 9

This example demonstrates the synthesis of the intermediate methyl 5-azido-4'-(1-(2,2,2-trifluoroacetyl)piperidin-4-yl)-[1,1'-biphenyl]-3-carboxylate (22) in an embodiment of the invention (FIG. 2).

To a solution of 21 (0.121 g, 0.29 mmol) in a 3:7 mixture of H$_2$O and ACN (10 ml), pTs-OH (0.509 g, 2.6 mmol) was added, and the mixture was stirred for 5 min. NaNO$_2$ (0.184 g, 2.6 mmol) was then added, and the yellow solution was stirred at room temperature. The course of the reaction was followed using TLC (Hex/EtOAc 60:40), and the reaction was allowed to continue until the starting material disappeared. NaN$_3$ (0.030 g, 0.47 mmol) was added at room temperature, and the reaction mixture was stirred overnight. Et$_2$O was added and the phases were separated. The organic phase was dried over Na$_2$SO$_4$, filtered and concentrated under vacuum to give an orange oil that was purified by silica gel chromatography using as eluant hexane/EtOAc (70:30) to afford the title compound as a yellow oil (0.107 g, 83%). $^1$H NMR (400 MHz, chloroform-d) δ 8.03 (t, J=1.6 Hz, 1H), 7.68 (t, J=1.6 Hz, 1H), 7.56 (d, J=8.3 Hz, 2H), 7.37 (t, J=2.0 Hz, 1H), 7.30 (d, J=8.2 Hz, 2H), 4.80-4.63 (m, 1H), 4.17 (dd, J=4.0, 14.2 Hz, 1H), 3.96 (s, 3H), 3.27 (td, J=2.4, 13.3 Hz, 1H), 2.99-2.76 (m, 2H), 2.02 (d, J=15.0 Hz, 2H), 1.76 (qd, J=4.2, 12.8 Hz, 2H). $^{13}$C NMR (101 MHz, Chloroform-d) δ 166.6, H, 155.9, H, 144.9, H, 143.2, H, 141.5, H, 138.1, H, 132.7, H, 127.8, H, 125.1, H, 122.1, H, 118.7, H, 52.9, H, 46.8, H, 44.6, H, 42.5, H, 34.0, H, 33.0, H.

Example 10

This example demonstrates a general procedure for the click cycloaddition reaction for the synthesis of compounds or intermediates in an embodiment of the invention (FIG. 2).

To a solution of aryl azide (1 eq) and aryl alkyne (1.5 eq) in 2 mL of tetrahydrofuran (THF):water (1:1), sodium ascorbate (freshly prepared 1 M aqueous solution) and CuSO$_4$ (0.5 eq) were sequentially added. The resulting reaction was vigorously stirred for 12 h at room temperature. The reaction mixture was then concentrated in vacuo and purified by flash chromatography (hexane:ethyl acetate=6:4).

Methyl 5-(4-phenyl-1H-1,2,3-triazol-1-yl)-4'-(1-(2,2,2-trifluoroacetyl)piperidin-4-yl)-[1,1'-biphenyl]-3-carboxylate (23a). Yellow solid, m/z (ESI, MH$^+$) 535; ESI-HRMS (MH$^+$) calcd. for C$_{29}$H$_{26}$F$_3$N$_4$O$_3$ 535.1952, found 535.1957.

Methyl 5-(4-(4-(trifluoromethyl)phenyl)-1H-1,2,3-triazol-1-yl)-4'-(1-(2,2,2-trifluoroacetyl)piperidin-4-yl)-[1,1'-biphenyl]-3-carboxylate (23b). Orange sticky solid, m/z (ESI, MH$^+$) 603; ESI-HRMS (MH$^+$) calcd. for C$_{30}$H$_{25}$F$_6$N$_4$O$_3$ 603.1825, found 603.1831.

Methyl 5-(4-(4-(ethylphenyl)-1H-1,2,3-triazol-1-yl)-4'-(1-(2,2,2-trifluoroacetyl)piperidin-4-yl)-[1,1'-biphenyl]-3-carboxylate (23c). Yellow solid 2.8 mg (43%), m/z (ESI, MH$^+$) 563.2; ESI-HRMS (MH$^+$) calcd. for C$_{31}$H$_{30}$F$_3$N$_4$O$_3$ 563.2270, found 563.2274.

Methyl 5-(4-(4-(hydroxymethyl)phenyl)-1H-1,2,3-triazol-1-yl)-4'-(1-(2,2,2-trifluoroacetyl)piperidin-4-yl)-[1,1'-biphenyl]-3-carboxylate (23d). Yellow solid 1.6 mg (25%), m/z (ESI, M+H$^+$) 565.2; ESI-HRMS (M+H$^+$) calcd. for C$_{30}$H$_{28}$F$_3$N$_4$O$_4$ 565.2063, found 565.2068.

Methyl 5-(4-(3-methoxyphenyl)-1H-1,2,3-triazol-1-yl)-4'-(1-(2,2,2-trifluoroacetyl)piperidin-4-yl)-[1,1'-biphenyl]-3-carboxylate (23e). Yellow solid 4 mg (80%), m/z (ESI, M+H$^+$) 565.1; ESI-HRMS (M+H$^+$) calcd. for $C_{30}H_{28}F_3N_4O_4$ 565.2063, found 565.2056.

Methyl 5-(4-(4-aminophenyl)-1H-1,2,3-triazol-1-yl)-4'-(1-(2,2,2-trifluoroacetyl) piperidin-4-yl)-[1,1'-biphenyl]-3-carboxylate (23f). Yellow solid 1.7 mg (27%), m/z (ESI, M+H$^+$) 550.2; ESI-HRMS (M+H$^+$) calcd. for $C_{29}H_{27}F_3N_5O_3$ 550.2066, found 550.2075.

Methyl 5-(4-(4-chlorophenyl)-1H-1,2,3-triazol-1-yl)-4'-(1-(2,2,2-trifluoroacetyl) piperidin-4-yl)-[1,1'-biphenyl]-3-carboxylate (23g). Yellow solid 3.6 mg (55%), m/z (ESI, M+H$^+$) 569.2; ESI-HRMS (M+H$^+$) calcd. for $C_{29}H_{25}{}^{35}ClF_3N_4O_3$ 569.1567, found 569.1561.

Methyl 5-(4-(4-bromophenyl)-1H-1,2,3-triazol-1-yl)-4'-(1-(2,2,2-trifluoroacetyl) piperidin-4-yl)-[1,1'-biphenyl]-3-carboxylate (23h). Yellow solid 3.8 mg (54%), m/z (ESI, M+H$^+$) 613.1; ESI-HRMS (M+H$^+$) calcd. for $C_{29}H_{25}{}^{79}BrF_3N_4O_3$ 613.1062, found 613.1057.

Methyl 5-(4-(thiophen-3-yl)-1H-1,2,3-triazol-1-yl)-4'-(1-(2,2,2-trifluoroacetyl)piperidin-4-yl)-[1,1'-biphenyl]-3-carboxylate (23i). Yellow solid 4.2 mg (67%), m/z (ESI, M+H$^+$) 541.1.

Methyl 5-(4-(thiophen-2-yl)-1H-1,2,3-triazol-1-yl)-4'-(1-(2,2,2-trifluoroacetyl)piperidin-4-yl)-[1,1'-biphenyl]-3-carboxylate (23j). Yellow solid 1.6 mg (26%), m/z (ESI, M+H$^+$) 541.2; ESI-HRMS (M+H$^+$) calcd. for $C_{27}H_{24}F_3N_4O_3{}^{32}S$ 541.1521, found 541.1523.

Methyl 5-(4-(5-chlorothiophen-2-yl)-1H-1,2,3-triazol-1-yl)-4'-(1-(2,2,2-trifluoroacetyl)-piperidin-4-yl)-[1,1'-biphenyl]-3-carboxylate (23k). Brown solid, m/z (ESI, MH$^+$) 575; ESI-HRMS (MH$^+$) calcd. for $C_{27}H_{23}F_3N_4O_3SCl$ 575.1131, found 575.1132.

Methyl 5-(4-(5-bromothiophen-2-yl)-1H-1,2,3-triazol-1-yl)-4'-(1-(2,2,2-trifluoroacetyl)-piperidin-4-yl)-[1,1'-biphenyl]-3-carboxylate (23l). Orange solid 5.1 mg (72%), m/z (ESI, MH$^+$) 619.0; ESI-HRMS (MH$^+$) calcd. for $C_{27}H_{23}F_3N_4O_3S^{79}Br$ 619.0626, found 619.0618.

Methyl 5-(4-(4-methylphenyl)-1H-1,2,3-triazol-1-yl)-4'-(1-(2,2,2-trifluoroacetyl)piperidin-4-yl)-[1,1'-biphenyl]-3-carboxylate (23o). Yellow solid 4 mg (80%), m/z (ESI, M+H$^+$) 549.2; ESI-HRMS (M+H$^+$) calcd. for $C_{30}H_{28}F_3N_4O_4$ 549.2114, found 549.2119.

Methyl 5-(4-(4-isopropylphenyl)-1H-1,2,3-triazol-1-yl)-4'-(1-(2,2,2-trifluoroacetyl)piperidin-4-yl)-[1,1'-biphenyl]-3-carboxylate (24q). Colorless oil 4 mg (60%), m/z (ESI, M+H$^+$) 577.2; ESI-HRMS (M+H$^+$) calcd. for $C_{32}H_{32}F_3N_4O_3$ 577.2427, found 577.2417.

Methyl 5-(4-(4-(tert-butyl)phenyl)-1H-1,2,3-triazol-1-yl)-4'-(1-(2,2,2-trifluoroacetyl)piperidin-4-yl)-[1,1'-biphenyl]-3-carboxylate (23r). Yellow solid 5.5 mg (81%), m/z (ESI, M+H$^+$) 591.2; ESI-HRMS (M+H$^+$) calcd. for $C_{33}H_{34}F_3N_4O_3$ 591.2583, found 591.2589.

Methyl 5-(4-(3-(trifluoromethyl)phenyl)-1H-1,2,3-triazol-1-yl)-4'-(1-(2,2,2-trifluoroacetyl)piperidin-4-yl)-[1,1'-biphenyl]-3-carboxylate (23t). Yellow solid 6.15 mg (89%), m/z (ESI, M+H$^+$) 603.2.

Methyl 5-(4-(4-methoxyphenyl)-1H-1,2,3-triazol-1-yl)-4'-(1-(2,2,2-trifluoroacetyl) piperidin-4-yl)-[1,1'-biphenyl]-3-carboxylate (23u). Yellow solid 3.2 mg (49%), m/z (ESI, M+H$^+$) 565.2; ESI-HRMS (M+H$^+$) calcd. for $C_{30}H_{28}F_3N_4O_4$ 565.2063, found 565.2062.

Methyl 5-(4-(4-(pentyloxy)phenyl)-1H-1,2,3-triazol-1-yl)-4'-(1-(2,2,2-trifluoroacetyl)piperidin-4-yl)-[1,1'-biphenyl]-3-carboxylate (23v). Pale yellow oil 5.7 mg (81%), m/z (ESI, M+H$^+$) 621.2; ESI-HRMS (M+H$^+$) calcd. for $C_{34}H_{36}F_3N_4O_4$ 621.2689, found 621.2687.

Methyl 5-(4-(2-methoxyphenyl)-1H-1,2,3-triazol-1-yl)-4'-(1-(2,2,2-trifluoroacetyl)piperidin-4-yl)-[1,1'-biphenyl]-3-carboxylate (23w). Yellow solid 6.5 mg (99%), m/z (ESI, M+H$^+$) 565.1; ESI-HRMS (M+H$^+$) calcd. for $C_{30}H_{28}F_3N_4O_4$ 565.2063, found 565.2061.

Methyl 5-(4-(4-(trifluoromethoxy)phenyl)-1H-1,2,3-triazol-1-yl)-4'-(1-(2,2,2-trifluoroacetyl)piperidin-4-yl)-[1,1'-biphenyl]-3-carboxylate (23x). Yellow solid 3.4 mg (48%), m/z (ESI, M+H$^+$) 619.1; ESI-HRMS (M+H$^+$) calcd. for $C_{30}H_{25}F_6N_4O_4$ 619.1780, found 619.1784.

Methyl 5-(4-(3-(trifluoromethoxy)phenyl)-1H-1,2,3-triazol-1-yl)-4'-(1-(2,2,2-trifluoroacetyl)piperidin-4-yl)-[1,1'-biphenyl]-3-carboxylate (23y). Yellow solid 6 mg (84%), m/z (ESI, M+H$^+$) 619.2; ESI-HRMS (M+H$^+$) calcd. for $C_{30}H_{25}F_6N_4O_4$ 619.1780, found 619.1778.

Methyl 5-(4-(3-chlorophenyl)-1H-1,2,3-triazol-1-yl)-4'-(1-(2,2,2-trifluoroacetyl) piperidin-4-yl)-[1,1'-biphenyl]-3-carboxylate (23z). Yellow solid 3.5 mg (54%), m/z (ESI, M+H$^+$) 569.2; ESI-HRMS (M+H$^+$) calcd. for $C_{29}H_{25}{}^{35}ClF_3N_4O_3$ 569.1567, found 569.1570.

Methyl 5-(4-(4-fluorophenyl)-1H-1,2,3-triazol-1-yl)-4'-(1-(2,2,2-trifluoroacetyl) piperidin-4-yl)-[1,1'-biphenyl]-3-carboxylate (23aa). Yellow solid 3.9 mg (61%), m/z (ESI, M+H$^+$) 553.1; ESI-HRMS (M+H$^+$) calcd. for $C_{29}H_{25}F_4N_4O_3$ 553.1863, found 553.1855.

Methyl 5-(4-(3-fluorophenyl)-1H-1,2,3-triazol-1-yl)-4'-(1-(2,2,2-trifluoroacetyl) piperidin-4-yl)-[1,1'-biphenyl]-3-carboxylate (23bb). Yellow solid 4.5 mg (77%), m/z (ESI, M+H$^+$) 553.2; ESI-HRMS (M+H$^+$) calcd. for $C_{29}H_{25}F_4N_4O_3$ 553.1863, found 553.1872.

Methyl 5-(4-(2-fluorophenyl)-1H-1,2,3-triazol-1-yl)-4'-(1-(2,2,2-trifluoroacetyl) piperidin-4-yl)-[1,1'-biphenyl]-3-carboxylate (23cc). Yellow solid 4.9 mg (71%), m/z (ESI, M+H$^+$) 553.2; ESI-HRMS (M+H$^+$) calcd. for $C_{29}H_{25}F_4N_4O_3$ 553.1863, found 553.1866.

Methyl 5-(4-(3,4-difluorophenyl)-1H-1,2,3-triazol-1-yl)-4'-(1-(2,2,2-trifluoroacetyl)piperidin-4-yl)-[1,1'-biphenyl]-3-carboxylate (23dd). Pale yellow solid 4.23 mg (65%), m/z (ESI, M+H$^+$) 571.1; ESI-HRMS (M+H$^+$) calcd. for $C_{29}H_{24}F_5N_4O_3$ 571.1769, found 571.1758.

Methyl 5-(4-(3,5-difluorophenyl)-1H-1,2,3-triazol-1-yl)-4'-(1-(2,2,2-trifluoroacetyl)piperidin-4-yl)-[1,1'-biphenyl]-3-carboxylate (23ee). Yellow solid 4.2 mg (63%), m/z (ESI, M+H$^+$) 571.1; ESI-HRMS (M+H$^+$) calcd. for $C_{29}H_{24}F_4N_5O_3$ 571.1769, found 571.1762.

Methyl 5-(4-(4-cyanophenyl)-1H-1,2,3-triazol-1-yl)-4'-(1-(2,2,2-trifluoroacetyl)piperidin-4-yl)-[1,1'-biphenyl]-3-carboxylate (23ff). Yellow solid 6 mg (94%), m/z (ESI, M+H$^+$) 560.2; ESI-HRMS (M+H$^+$) calcd. for $C_{30}H_{25}F_4N_5O_3$ 560.1909, found 560.1913.

Methyl 5-(4-(4-acetylphenyl)-1H-1,2,3-triazol-1-yl)-4'-(1-(2,2,2-trifluoroacetyl)piperidin-4-yl)-[1,1'-biphenyl]-3-carboxylate (23hh). Yellow solid 4.45 mg (67%), m/z (ESI, M+H$^+$) 577.2; ESI-HRMS (M+H$^+$) calcd. for $C_{31}H_{28}F_3N_4O_4$ 577.2063, found 577.2056.

Methyl 5-(4-(3,4-dimethoxyphenyl)-1H-1,2,3-triazol-1-yl)-4'-(1-(2,2,2-trifluoroacetyl)piperidin-4-yl)-[1,1'-biphenyl]-3-carboxylate (23ii). Yellow solid 5.65 mg (83%), m/z (ESI, M+H$^+$) 595.2; ESI-HRMS (M+H$^+$) calcd. for $C_{31}H_{30}F_3N_4O_5$ 595.2168, found 595.2173.

Methyl 5-(4-(3-hydroxyphenyl)-1H-1,2,3-triazol-1-yl)-4'-(1-(2,2,2-trifluoroacetyl) piperidin-4-yl)-[1,1'-biphenyl]-3-carboxylate (23jj). Yellow solid 5.15 mg (81%), m/z (ESI, M+H$^+$) 551.1; ESI-HRMS (M+H$^+$) calcd. for $C_{29}H_{26}F_3N_4O_4$ 551.1906, found 551.1901.

Methyl 5-(4-(3-aminophenyl)-1H-1,2,3-triazol-1-yl)-4'-(1-(2,2,2-trifluoroacetyl) piperidin-4-yl)-[1,1'-biphenyl]-3-carboxylate (23kk). Yellow solid 2.4 mg (38%), m/z (ESI, M+H$^+$) 550.1; ESI-HRMS (M+H$^+$) calcd. for $C_{29}H_{27}F_3N_5O_3$ 550.2066, found 550.2056.

Methyl 5-(4-(pyridin-4-yl)-1H-1,2,3-triazol-1-yl)-4'-(1-(2,2,2-trifluoroacetyl)piperidin-4-yl)-[1,1'-biphenyl]-3-carboxylate (23ll). Yellow solid 2.3 mg (37%), m/z (ESI, M+H$^+$) 536.1; ESI-HRMS (M+H$^+$) calcd. for $C_{28}H_{25}F_3N_5O_3$ 536.1909, found 536.1913.

Methyl 5-(4-(pyrazin-2-yl)-1H-1,2,3-triazol-1-yl)-4'-(1-(2,2,2-trifluoroacetyl)piperidin-4-yl)-[1,1'-biphenyl]-3-carboxylate (23 mm). Yellow solid 3.5 mg (57%).

Methyl 5-(4-(furan-2-yl)-1H-1,2,3-triazol-1-yl)-4'-(1-(2,2,2-trifluoroacetyl)piperidin-4-yl)-[1,1'-biphenyl]-3-carboxylate (23nn). Yellow solid 3 mg (50%), m/z (ESI, M+H$^+$) 525.1; ESI-HRMS (M+H$^+$) calcd. for $C_{27}H_{24}F_3N_4O_4$ 525.1750, found 525.1744.

Methyl 5-(4-(benzofuran-2-yl)-1H-1,2,3-triazol-1-yl)-4'-(1-(2,2,2-trifluoroacetyl)piperidin-4-yl)-[1,1'-biphenyl]-3-carboxylate (23oo). Brown solid 4 mg (60%), m/z (ESI, M+H$^+$) 575.2; ESI-HRMS (M+H$^+$) calcd. for $C_{31}H_{26}F_3N_4O_4$ 575.1906, found 575.1909.

Methyl 5-(4-(thiazol-2-yl)-1H-1,2,3-triazol-1-yl)-4'-(1-(2,2,2-trifluoroacetyl)piperidin-4-yl)-[1,1'-biphenyl]-3-carboxylate (23pp). Yellow solid 4.6 mg (74%), m/z (ESI, M+H$^+$) 542.1; ESI-HRMS (M+H$^+$) calcd. for $C_{26}H_{23}F_3N_5O_3{}^{32}S$ 542.1474, found 542.1465.

Methyl 5-(4-cyclohexyl-1H-1,2,3-triazol-1-yl)-4'-(1-(2,2,2-trifluoroacetyl)piperidin-4-yl)-[1,1'-biphenyl]-3-carboxylate (23qq). Yellow solid 5.4 mg (87%), m/z (ESI, M+H$^+$) 541.2; ESI-HRMS (M+H$^+$) calcd. for $C_{29}H_{32}F_3N_4O_3$ 541.2427, found 541.2419.

Methyl 5-(4-cyclopropyl-1H-1,2,3-triazol-1-yl)-4'-(1-(2,2,2-trifluoroacetyl)piperidin-4-yl)-[1,1'-biphenyl]-3-carboxylate (23rr). Yellow solid 5.7 mg (99%), m/z (ESI, M+H$^+$) 499.2; ESI-HRMS (M+H$^+$) calcd. for $C_{26}H_{26}F_3N_4O_3$ 499.1957, found 499.1959.

Example 11

This example demonstrates the synthesis of 5-(4-phenyl-1H-1,2,3-triazol-1-yl)-4'-(piperidin-4-yl)-[1,1'-biphenyl]-3-carboxylic acid (24a) in an embodiment of the invention (FIG. 2).

To a solution of 23a (9 mg, 17 μmol) in 2 mL of MeOH:H$_2$O (1:1), KOH (9.5 mg, 170 μmol) was added and the resulting mixture was heated at 50° C. for 12 h. After removing the solvents under vacuum, the mixture was purified by preparative HPLC (Method B, R$_t$=25.7 min). The product was obtained as a white solid by lyophilization (1.9 mg, 26%). (ESI, MH$^+$) 425; ESI-HRMS (MH$^+$) calcd. for $C_{26}H_{25}N_4O_2$ 425.1978, found 425.1978, HPLC purity 97.1% (Rt=8.9 min). $^1$H NMR (400 MHz, MeOD) δ:1.77-1.80 (3H, m), 1.94-1.97 (2H, m), 2.90-2.96 (4H, m), 7.31-7.35 (3H, m), 7.39-7.43 (2H, m), 7.68 (2H, J=8 Hz, d), 7.88 (2H, J=8 Hz, d), 8.29 (2H, J=8 Hz, d), 8.94 (1H, s).

Example 12

This example demonstrates the synthesis of 5-(4-(4-(trifluoromethyl)phenyl)-1H-1,2,3-triazol-1-yl)-4'-(piperidin-4-yl)-[1,1'-biphenyl]-3-carboxylic acid (24b) in an embodiment of the invention (FIG. 2).

To a solution of 23b (6.3 mg, 10 μmol) in 2 mL of MeOH:H$_2$O (1:1), KOH (5.6 mg, 100 μmol) was added, and the resulting mixture was heated at 50° C. for 12 h. After removing the solvents under vacuum, the mixture was purified by preparative HPLC (Method B, R$_t$=30.2 min). The product was obtained as a white solid by lyophilization (2.1 mg, 42%). (ESI, MH$^+$) 493; ESI-HRMS (MH$^+$) calcd. for $C_{27}H_{24}F_3N_4O_2$ 493.1851, found 493.1851; HPLC purity 96.9% (R$_t$=10.1 min). $^1$H NMR (400 MHz, MeOD) δ:1.79-1.84 (2H, m), 1.98-2.04 (2H, m), 3.01-3.06 (4H, m), 7.45 (2H, J=8 Hz, d), 7.69-7.73 (4H, m), 8.10 (2H, J=8 Hz, d), 8.43 (2H, J=8 Hz, d), 8.99 (1H, s).

Example 13

This example demonstrates the synthesis of 5-(4-(4-ethylphenyl)-1H-1,2,3-triazol-1-yl)-4'-(piperidin-4-yl)-[1,1'-biphenyl]-3-carboxylic acid (24c) in an embodiment of the invention (FIG. 2).

To a solution of 23c (2.8 mg, 5 μmol) in 2 mL of MeOH:H$_2$O (1:1), KOH (5.6 mg, 100 μmol) was added, and the resulting mixture was heated at 50° C. for 12 h. After removing the solvents under vacuum, the mixture was purified by preparative HPLC (Method B, R$_t$=27.0 min). The product was obtained as a white solid by lyophilization (2.4 mg, 67%). (ESI, MH$^+$) 453.2; ESI-HRMS (MH$^+$) calcd. for $C_{28}H_{29}N_4O_2$ 453.2291, found 453.2294; HPLC purity 98.6% (R$_t$=11.5 min).

Example 14

This example demonstrates the synthesis of 5-(4-(4-(hydroxymethyl)phenyl)-1H-1,2,3-triazol-1-yl)-4'-(piperidin-4-yl)-[1,1'-biphenyl]-3-carboxylic acid (24d) in an embodiment of the invention (FIG. 2).

To a solution of 23d (1.6 mg, 2.8 μmol) in 2 mL of MeOH:H$_2$O (1:1), KOH (5.6 mg, 100 μmol) was added, and the resulting mixture was heated at 50° C. for 12 h. After removing the solvents under vacuum, the mixture was purified by preparative HPLC (Method B, R$_t$=23.3 min). The product was obtained as a white solid by lyophilization (1.4 mg, 99%). (ESI, MH$^+$) 455.2; ESI-HRMS (MH$^+$) calcd. for $C_{27}H_{27}N_4O_3$ 455.2083, found 455.2081; HPLC purity 96.3% (R$_t$=8.42 min).

Example 15

This example demonstrates the synthesis of 5-(4-(3-methoxyphenyl)-1H-1,2,3-triazol-1-yl)-4'-(piperidin-4-yl)-[1,1'-biphenyl]-3-carboxylic acid (24e) in an embodiment of the invention (FIG. 2).

To a solution of 23e (4 mg, 7 μmol) in 2 mL of MeOH:H$_2$O (1:1), KOH (5.6 mg, 100 μmol) was added, and the resulting mixture was heated at 50° C. for 12 h. After removing the solvents under vacuum, the mixture was purified by preparative HPLC (Method B, R$_t$=23.2 min). The product was obtained as a white solid by lyophilization (2.4 mg, 67%). (ESI, MH$^+$) 455.2; ESI-HRMS (MH$^+$) calcd. for $C_{27}H_{27}N_4O_3$ 455.2083, found 455.2083; HPLC purity 99.8% (R$_t$=10.1 min). $^1$H NMR (500 MHz, DMSO-d$_6$): δ (ppm)=9.52 (s, 1H, CH$_{triazole}$), 8.42 (s, 1H), 8.33 (s, 1H), 8.19 (s, 1H), 7.78 (d, J=7.8 Hz, 2H), 7.63-7.52 (m, 1H), 7.42 (m, 3H), 6.95 (d, J=8.1 Hz, 1H), 6.81 (s, 1H), 3.84 (s, 3H, CH$_3$), 2.90 (m, 3H), 1.91 (m, 5H). Proton signals for 2-CH$_{piperidine}$, 6-CH$_{piperidine}$ and 3-CH$_{piperidine}$, 5-CH$_{piperidine}$ are hidden under the H$_2$O and DMSO-d$_6$ signals. $^{13}$C NMR (500 MHz, DMSO-d$_6$): δ (ppm)=172.8 (1C), 168.7 (1C), 160.3 (1C), 147.7 (1C), 145.9 (1C), 141.3 (1C), 137.8 (1C), 137.3 (1C), 132.2 (1C), 130.7 (2C), 127.9

(2C), 127.5 (2C), 127.4 (1C), 120.5 (1C), 119.5 (1C), 119.1 (2C), 118.1 (1C), 114.5 (1C), 111.0 (2C), 55.7 (2C), 44.6 (2C), 30.8 (1C), 29.5 (1C).

Example 16

This example demonstrates the synthesis of 5-(4-(4-aminophenyl)-1H-1,2,3-triazol-1-yl)-4'-(piperidin-4-yl)-[1,1'-biphenyl]-3-carboxylic acid (24f) in an embodiment of the invention (FIG. 2).

To a solution of 23f (3.3 mg, 6 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, R$_t$=17.4 min). The product was obtained as a white solid by lyophilization (2.84 mg, 95%). (ESI, MH$^+$) 440.2; HPLC purity 96% (R$_t$=8.38 min).

Example 17

This example demonstrates the synthesis of 5-(4-(4-chlorophenyl)-1H-1,2,3-triazol-1-yl)-4'-(piperidin-4-yl)-[1,1'-biphenyl]-3-carboxylic acid (24g) in an embodiment of the invention (FIG. 2).

To a solution of 23g (3.6 mg, 6.3 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, R$_t$=22.7 min). The product was obtained as a white solid by lyophilization (3.3 mg, 99%). (ESI, MH$^+$) 459.2; ESI-HRMS (MH$^+$) calcd. for C$_{26}$H$_{24}$$^{35}$ClN$_4$O$_2$ 459.1588, found 459.1588; HPLC purity 98.4% (R$_t$=11.4 min). $^1$H NMR (500 MHz, DMSO-d$_6$): δ (ppm)=9.49 (s, 1H), 8.34 (s, 1H), 8.24 (s, 1H), 8.10 (s, 1H), 8.01 (d, J=8.6 Hz, 2H), 7.72 (d, J=8.4 Hz, 2H), 7.58 (d, J=8.6 Hz, 2H), 7.38 (d, J=8.4 Hz, 2H), 3.08 (d, J=12.2 Hz, 2H), 2.69-2.59 (m, 3H), 1.81-1.70 (m, 5H), 1.60 (qd, J=3.8, 12.4 Hz, 2H). $^{13}$C NMR (500 MHz, DMSO-d$_6$): δ (ppm)=173.6 (1C), 167.6 (1C), 145.0 (1C), 146.6 (1C), 144.2 (1C), 141.1 (2C), 137.5 (1C), 136.9 (2C), 133.0 (2C), 129.7 (2C), 129.5 (2C), 127.8 (2C), 127.5 (2C), 127.3 (2C), 120.6 (2C), 119.6 (2C), 118.3 (2C), 49.0 (1C), 46.5 (2C), 42.2 (1C), 33.9 (2C), 23.6 (1C).

Example 18

This example demonstrates the synthesis of 5-(4-(4-bromophenyl)-1H-1,2,3-triazol-1-yl)-4'-(piperidin-4-yl)-[1,1'-biphenyl]-3-carboxylic acid (24h) in an embodiment of the invention (FIG. 2).

A solution of 23h (3.8 mg, 6.2 µmol) in of 2 mL MeOH:1.0 M KOH (1:1) was heated at 50° C. for 12 h. After removing the solvents under vacuum, the mixture was purified by preparative HPLC (Method B, R$_t$=24.2 min). The product was obtained as a white acetate salt by lyophilization (3.5 mg, 99%). (ESI, MH$^+$) 503.1; ESI-HRMS (MH$^+$) calcd. for C$_{26}$H$_{24}$N$_4$O$_2$$^{79}$Br 503.1083, found 503.1080.

Example 19

This example demonstrates the synthesis of 5-(4-(thiophen-3-yl)-1H-1,2,3-triazol-1-yl)-4'-(piperidin-4-yl)-[1,1'-biphenyl]-3-carboxylic acid (24i) in an embodiment of the invention (FIG. 2).

A solution of 23i (4.2 mg, 7.7 µmol) in of 2 mL MeOH:1.0 M KOH (1:1) was heated at 50° C. for 12 h. After removing the solvents under vacuum, the mixture was purified by preparative HPLC (Method B, R$_t$=22.3 min). The product was obtained as a white acetate salt by lyophilization (3.77 mg, 99%). (ESI, MH$^+$) 431.1; ESI-HRMS (MH$^+$) calcd. for C$_{24}$H$_{23}$N$_4$O$_2$$^{32}$S 431.1542, found 431.1548, HPLC purity 99% (Rt=9.7 min).

Example 20

This example demonstrates the synthesis of 5-(4-(thiophen-2-yl)-1H-1,2,3-triazol-1-yl)-4'-(piperidin-4-yl)-[1,1'-biphenyl]-3-carboxylic acid (24j) in an embodiment of the invention (FIG. 2).

A solution of 23j (2.6 mg, 5 µmol) in of 2 mL MeOH:1.0 M KOH (1:1) was heated at 50° C. for 12 h. After removing the solvents under vacuum, the mixture was purified by preparative HPLC (Method B, R$_t$=21.8 min). The product was obtained as a white acetate salt by lyophilization (2.2 mg, 99%). (ESI, MH$^+$) 431.2; ESI-HRMS (MH$^+$) calcd. for C$_{24}$H$_{23}$N$_4$O$_2$$^{32}$S 431.1542, found 431.1538, HPLC purity 97.1% (Rt=8.9 min).

Example 21

This example demonstrates the synthesis of 5-(4-(5-chlorothiophen-2-yl)-1H-1,2,3-triazol-1-yl)-4'-(piperidin-4-yl)-[1,1'-biphenyl]-3-carboxylic acid (24k) in an embodiment of the invention (FIG. 2).

To a solution of 23k (8.3 mg, 14 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=28.6 min). The product was obtained as a white solid by lyophilization (2.8 mg, 42%). (ESI, MH$^+$) 465; ESI-HRMS (MH$^+$) calcd. for C$_{24}$H$_{22}$N$_4$O$_2$SCl 465.1152, found 465.1151; HPLC purity 97.7% (Rt=10.6 min).

Example 22

This example demonstrates the synthesis of 5-(4-(5-bromothiophen-2-yl)-1H-1,2,3-triazol-1-yl)-4'-(piperidin-4-yl)-[1,1'-biphenyl]-3-carboxylic acid (24l) in an embodiment of the invention (FIG. 2).

To a solution of 23l (5.1 mg, 8.2 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=27.2 min). The product was obtained as a white solid by lyophilization (2.31 mg, 50%). (ESI, MH$^+$) 509.1; ESI-HRMS (MH$^+$) calcd. for C$_{24}$H$_{22}$N$_4$O$_2$SBr 509.0647, found 509.0648; HPLC purity 97.7% (Rt=11.8 min).

Example 23

This example demonstrates the synthesis of 5-(4-(4-methylphenyl)-1H-1,2,3-triazol-1-yl)-4'-(piperidin-4-yl)-[1,1'-biphenyl]-3-carboxylic acid (24o) in an embodiment of the invention (FIG. 2).

To a solution of 23o (6 mg, 10 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=24.4 min). The product was obtained as a white solid by lyophilization (1.9 mg, 43%).

Example 24

This example demonstrates the synthesis of 5-(4-(4-propylphenyl)-1H-1,2,3-triazol-1-yl)-4'-(piperidin-4-yl)-[1,1'-biphenyl]-3-carboxylic acid (24p) in an embodiment of the invention (FIG. 2).

To a solution of 23p (5 mg, 8.7 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=23.7 min). The product was obtained as a white solid by lyophilization (4.5 mg, 98%). (ESI, MH$^+$) 467.2; ESI-HRMS (MH$^+$) calcd. for C$_{29}$H$_{31}$N$_4$O$_2$ 467.2447, found 467.2454.

Example 25

This example demonstrates the synthesis of 5-(4-(4-isopropylphenyl)-1H-1,2,3-triazol-1-yl)-4'-(piperidin-4-yl)-[1,1'-biphenyl]-3-carboxylic acid (24q) in an embodiment of the invention (FIG. 2).

To a solution of 23q (4 mg, 6.9 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=18.1 min). The product was obtained as a white solid by lyophilization (3.55 mg, 97%). (ESI, MH$^+$) 467.2; ESI-HRMS (MH$^+$) calcd. for C$_{29}$H$_{31}$N$_4$O$_2$ 467.2447, found 467.2440.

Example 26

This example demonstrates the synthesis of 5-(4-(4-(tert-butyl)phenyl)-1H-1,2,3-triazol-1-yl)-4'-(piperidin-4-yl)-[1,1'-biphenyl]-3-carboxylic acid (24r) in an embodiment of the invention (FIG. 2).

To a solution of 23r (5.5 mg, 9.3 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=31.1 min). The product was obtained as a white solid by lyophilization (5.03 mg, 99%). (ESI, MH$^+$) 481.3; ESI-HRMS (MH$^+$) calcd. for C$_{30}$H$_{33}$N$_4$O$_2$ 481.2604, found 481.2597. HPLC purity 98.2% (R$_t$=12.9 min).

Example 27

This example demonstrates the synthesis of 5-(4-(3-(trifluoromethyl)phenyl)-1H-1,2,3-triazol-1-yl)-4'-(piperidin-4-yl)-[1,1'-biphenyl]-3-carboxylic acid (24t) in an embodiment of the invention (FIG. 2).

To a solution of 23t (6.15 mg, 10 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=27.6 min). The product was obtained as a white solid by lyophilization (2.53 mg, 46%). (ESI, MH$^+$) 493.1; ESI-HRMS (MH$^+$) calcd. for C$_{27}$H$_{24}$N$_4$O$_2$F$_3$ 493.1851, found 493.1851. HPLC purity 99% (R$_t$=11.8 min).

Example 28

This example demonstrates the synthesis of 5-(4-(4-methoxyphenyl)-1H-1,2,3-triazol-1-yl)-4'-(piperidin-4-yl)-[1,1'-biphenyl]-3-carboxylic acid (24u) in an embodiment of the invention (FIG. 2).

To a solution of 23u (3.2 mg, 5.7 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=23.0 min). The product was obtained as a white solid by lyophilization (2.14 mg, 73%). (ESI, MH$^+$) 455.2; ESI-HRMS (MH$^+$) calcd. for C$_{27}$H$_{27}$N$_4$O$_3$ 455.2083, found 455.2086. HPLC purity 97% (R$_t$=10.14 min).

Example 29

This example demonstrates the synthesis of 5-(4-(4-(pentyloxy)phenyl)-1H-1,2,3-triazol-1-yl)-4'-(piperidin-4-yl)-[1,1'-biphenyl]-3-carboxylic acid (24v) in an embodiment of the invention (FIG. 2).

To a solution of 23v (5.8 mg, 9.3 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=34.1 min). The product was obtained as a white solid by lyophilization (5.3 mg, 99%). (ESI, MH$^+$) 511.3; ESI-HRMS (MH$^+$) calcd. for C$_{31}$H$_{35}$N$_4$O$_3$ 511.2709, found 511.2703.

Example 30

This example demonstrates the synthesis of 5-(4-(2-methoxyphenyl)-1H-1,2,3-triazol-1-yl)-4'-(piperidin-4-yl)-[1,1'-biphenyl]-3-carboxylic acid (24w) in an embodiment of the invention (FIG. 2).

To a solution of 23w (6.5 mg, 11.5 µmol) in 2 mL of MeOH:H$_2$O (1:1), KOH (7.9 mg, 140 µmol) was added and the resulting mixture was heated at 60° C. for 6 h. After removing the solvents under vacuum, the mixture was purified by preparative HPLC (Method B, R$_t$=23.0 min). The product was obtained as a white solid by lyophilization (3.05 mg, 52%). (ESI, MH$^+$) 455.2; ESI-HRMS (MH$^+$) calcd. for C$_{27}$H$_{27}$N$_4$O$_3$ 455.2083, found 455.2086. HPLC purity 98% (R$_t$=10.44 min).

Example 31

This example demonstrates the synthesis of 5-(4-(3-(trifluoromethoxy)phenyl)-1H-1,2,3-triazol-1-yl)-4'-(piperidin-4-yl)-[1,1'-biphenyl]-3-carboxylic acid (24y) in an embodiment of the invention (FIG. 2).

A solution of 23y (6 mg, 9.7 µmol) in of 2 mL MeOH:1.0 M KOH (1:1) was heated at 50° C. for 12 h. After removing the solvents under vacuum, the mixture was purified by preparative HPLC (Method B, R$_t$=29.2 min). The product was obtained as a white acetate salt by lyophilization (3.63 mg, 66%). (ESI, MH$^+$) 509.2; ESI-HRMS (MH$^+$) calcd. for C$_{27}$H$_{24}$N$_4$O$_3$F$_3$ 509.1801, found 509.1798.

Example 32

This example demonstrates the synthesis of 5-(4-(3-chlorophenyl)-1H-1,2,3-triazol-1-yl)-4'-(piperidin-4-yl)-[1,1'-biphenyl]-3-carboxylic acid (24z) in an embodiment of the invention (FIG. 2).

To a solution of 23z (3.5 mg, 6.2 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, R$_t$=21.2 min). The product was obtained as a white solid by lyophilization (2.2 mg, 68%). (ESI, MH$^+$) 459.2; ESI-HRMS (MH$^+$) calcd. for C$_{26}$H$_{24}$$^{35}$ClN$_4$O$_2$ 459.1588, found 459.1583; HPLC purity 98% (R$_t$=11.1 min).

Example 33

This example demonstrates the synthesis of 5-(4-(4-fluorophenyl)-1H-1,2,3-triazol-1-yl)-4'-(piperidin-4-yl)-[1,1'-biphenyl]-3-carboxylic acid (24aa) in an embodiment of the invention (FIG. 2).

A solution of 23aa (3.87 mg, 7 µmol) in of 2 mL MeOH:1.0 M KOH (1:1) was heated at 50° C. for 12 h. After removing the solvents under vacuum, the mixture was purified by preparative HPLC (Method B, R$_t$=20.6 min). The product was obtained as a salt by lyophilization (3.06 mg, 99%). (ESI, MH$^+$) 443.1; ESI-HRMS (MH$^+$) calcd. for C$_{26}$H$_{24}$FN$_4$O$_2$ 443.1883, found 443.1890, HPLC purity 96% (R$_t$=10.8 min).

Example 34

This example demonstrates the synthesis of 5-(4-(3-fluorophenyl)-1H-1,2,3-triazol-1-yl)-4'-(piperidin-4-yl)-[1,1'-biphenyl]-3-carboxylic acid (24bb) in an embodiment of the invention (FIG. 2).

A solution of 23bb (4.5 mg, 8.2 µmol) in of 2 mL MeOH:1.0 M KOH (1:1) was heated at 50° C. for 12 h. After removing the solvents under vacuum, the mixture was purified by preparative HPLC (Method B, R$_t$=20.5 min). The product was obtained as a white acetate salt by lyophilization (3.4 mg, 84%). (ESI, MH$^+$) 443.1; ESI-HRMS (MH$^+$) calcd. for C$_{26}$H$_{24}$FN$_4$O$_2$ 443.1883, found 443.1884, HPLC purity 98.2% (Rt=10.5 min). $^1$H NMR (500 MHz, DMSO-d6): δ (ppm)=9.57 (s, 1H), 8.37 (s, 1H), 8.24 (s, 1H), 8.11 (s, 1H), 7.85 (t, J=8.1 Hz, 1H), 7.80 (t, J=8.1 Hz, 1H), 7.72 (d, J=8.3 Hz, 2H), 7.56 (p, J=8.1 Hz, 1H), 7.38 (d, J=8.3 Hz, 2H), 3.10 (t, J=8.8 Hz, 2H), 2.75-2.59 (m, 3H), 1.81-1.72 (m, 5H), 1.63 (m, 2H).

Example 35

This example demonstrates the synthesis of 5-(4-(2-fluorophenyl)-1H-1,2,3-triazol-1-yl)-4'-(piperidin-4-yl)-[1,1'-biphenyl]-3-carboxylic acid (24cc) in an embodiment of the invention (FIG. 2).

A solution of 23cc (4.9 mg, 8.8 µmol) in of 2 mL MeOH:1.0 M KOH (1:1) was heated at 50° C. for 12 h. After removing the solvents under vacuum, the mixture was purified by preparative HPLC (Method B, R$_t$=24.3 min). The product was obtained as a white acetate salt by lyophilization (2.64 mg, 60%). (ESI, MH$^+$) 443.1; ESI-HRMS (MH$^+$) calcd. for C$_{26}$H$_{24}$FN$_4$O$_2$ 443.1887, found 443.1884.

Example 36

This example demonstrates the synthesis of 5-(4-(3,4-difluorophenyl)-1H-1,2,3-triazol-1-yl)-4'-(piperidin-4-yl)-[1,1'-biphenyl]-3-carboxylic acid (24dd) in an embodiment of the invention (FIG. 2).

A solution of 23dd (4.2 mg, 7.4 µmol) in of 2 mL MeOH:1.0 M KOH (1:1) was heated at 50° C. for 12 h. After removing the solvents under vacuum, the mixture was purified by preparative HPLC (Method B, R$_t$=21.1 min). The product was obtained as a white acetate salt by lyophilization (3.85 mg, 99%). (ESI, MH$^+$) 461.2; ESI-HRMS (MH$^+$) calcd. for C$_{26}$H$_{23}$F$_2$N$_4$O$_2$ 461.1789, found 461.1790.

Example 37

This example demonstrates the synthesis of 5-(4-(3,5-difluorophenyl)-1H-1,2,3-triazol-1-yl)-4'-(piperidin-4-yl)-[1,1'-biphenyl]-3-carboxylic acid (24ee) in an embodiment of the invention (FIG. 2).

A solution of 23ee (4.16 mg, 7.3 µmol) in of 2 mL MeOH:1.0 M KOH (1:1) was heated at 50° C. for 12 h. After removing the solvents under vacuum, the mixture was purified by preparative HPLC (Method B, R$_t$=22.2 min). The product was obtained as a white acetate salt by lyophilization (1.24 mg, 33%). (ESI, MH$^+$) 461.2; ESI-HRMS (MH$^+$) calcd. for C$_{26}$H$_{23}$F$_2$N$_4$O$_2$ 461.1789, found 461.1782.

Example 38

This example demonstrates the synthesis of 5-(4-(4-carboxyphenyl)-1H-1,2,3-triazol-1-yl)-4'-(piperidin-4-yl)-[1,1'-biphenyl]-3-carboxylic acid (24ff) in an embodiment of the invention (FIG. 2).

A solution of 23ff (6 mg, 10 µmol) in of 2 mL MeOH:1.0 M KOH (1:1) was heated at 50° C. for 12 h. After removing the solvents under vacuum, the mixture was purified by preparative HPLC (Method B, R$_t$=9.4 min). The product was obtained as a white acetate salt by lyophilization, (ESI, MH$^+$) 469.2; ESI-HRMS (MH$^+$) calcd. for C$_{27}$H$_{25}$F$_2$N$_4$O$_4$ 469.1876, found 469.1870.

Example 39

This example demonstrates the synthesis of 5-(4-(3-carboxyphenyl)-1H-1,2,3-triazol-1-yl)-4'-(piperidin-4-yl)-[1,1'-biphenyl]-3-carboxylic acid (24gg) in an embodiment of the invention (FIG. 2).

To a solution of aryl azide (5 mg, 11.5 µmol, 1 eq) and 3-ethynylbenzoic acid (2.5 mg, 17 µmol, 1.5 eq) in 2 mL of THF:water (1:1), sodium ascorbate (17 µmol, freshly prepared 1 M aqueous solution, 1.5 eq) and CuSO$_4$ (1.4 mg, 6 µmol, 0.5 eq) were sequentially added. The resulting reaction was vigorously stirred for 12 h at room temperature. The reaction mixture was then concentrated in vacuo and added to a solution of 2 mL MeOH:1.0 M KOH (1:1), the mixture was heated at 50° C. for 12 h. After removing the solvents under vacuum, the mixture was purified by preparative HPLC (Method B, R$_t$=10.4 min). The product was obtained as a white acetate salt by lyophilization (5.7 mg, 93%), (ESI, MH$^+$) 469.2; ESI-HRMS (MH$^+$) calcd. for C$_{27}$H$_{25}$F$_2$N$_4$O$_4$ 469.1876, found 469.1884.

Example 40

This example demonstrates the synthesis of 5-(4-(4-acetylphenyl)-1H-1,2,3-triazol-1-yl)-4'-(piperidin-4-yl)-[1,1'-biphenyl]-3-carboxylic acid (24hh) in an embodiment of the invention (FIG. 2).

A solution of 23hh (4.5 mg, 7.7 µmol) in of 2 mL MeOH:1.0 M KOH (1:1) was heated at 50° C. for 12 h. After removing the solvents under vacuum, the mixture was purified by preparative HPLC (Method B, R$_t$=19.4 min). The product was obtained as a white acetate salt by lyophilization (3.88 mg, 95%). (ESI, MH$^+$) 467.2; ESI-HRMS (MH$^+$) calcd. for C$_{28}$H$_{27}$N$_4$O$_3$ 467.2083, found 467.2084, HPLC purity 96.6% (R$_t$=10.4 min).

Example 41

This example demonstrates the synthesis of 5-(4-(3,4-dimethoxyphenyl)-1H-1,2,3-triazol-1-yl)-4'-(piperidin-4- yl)-[1,1'-biphenyl]-3-carboxylic acid (24ii) in an embodiment of the invention (FIG. 2).

A solution of 23ii (5.65 mg, 9.5 µmol) in of 2 mL MeOH:1.0 M KOH (1:1) was heated at 50° C. for 12 h. After removing the solvents under vacuum, the mixture was purified by preparative HPLC (Method B, $R_t$=13.5 min). The product was obtained as a white acetate salt by lyophilization (5.2 mg, 99%). (ESI, MH$^+$) 485.2; ESI-HRMS (MH$^+$) calcd. for $C_{28}H_{29}N_4O_4$ 485.2189, found 485.2195.

Example 42

This example demonstrates the synthesis of 5-(4-(3-hydroxyphenyl)-1H-1,2,3-triazol-1-yl)-4'-(piperidin-4-yl)-[1, 1'-biphenyl]-3-carboxylic acid (24jj) in an embodiment of the invention (FIG. 2).

A solution of 23jj (5.15 mg, 9.3 µmol) in of 2 mL MeOH:1.0 M KOH (1:1) was heated at 50° C. for 12 h. After removing the solvents under vacuum, the mixture was purified by preparative HPLC (Method B, $R_t$=17.9 min). The product was obtained as a white acetate salt by lyophilization (4.7 mg, 99%). (ESI, MH$^+$) 441.2; ESI-HRMS (MH$^+$) calcd. for $C_{26}H_{25}N_4O_3$ 441.1927, found 441.1931, HPLC purity 96.2% ($R_t$=8.7 min).

Example 43

This example demonstrates the synthesis of 5-(4-(3-aminophenyl)-1H-1,2,3-triazol-1-yl)-4'-(piperidin-4-yl)-[1, 1'-biphenyl]-3-carboxylic acid (24kk) in an embodiment of the invention (FIG. 2).

To a solution of 23kk (2.4 mg, 4.3 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, $R_t$=17.4 min). The product was obtained as a white solid by lyophilization (2.2 mg, 99%). (ESI, MH$^+$) 440.2; ESI-HRMS (MH$^+$) calcd. for $C_{26}H_{26}N_5O_2$ 440.2087, found 440.2093.

Example 44

This example demonstrates the synthesis of 5-(4-(pyridin-4-yl)-1H-1,2,3-triazol-1-yl)-4'-(piperidin-4-yl)-[1,1'-biphenyl]-3-carboxylic acid (24ll) in an embodiment of the invention (FIG. 2).

To a solution of 23ll (2.3 mg, 4.3 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, $R_t$=15.7 min). The product was obtained as a white solid by lyophilization (2 mg, 94%). (ESI, MH$^+$) 426.1; ESI-HRMS (MH$^+$) calcd. for $C_{25}H_{24}N_5O_2$ 426.1930, found 426.1933.

Example 45

This example demonstrates the synthesis of 5-(4-(pyrazin-2-yl)-1H-1,2,3-triazol-1-yl)-4'-(piperidin-4-yl)-[1, 1'-biphenyl]-3-carboxylic acid (24 mm) in an embodiment of the invention (FIG. 2).

To a solution of 23 mm (3.55 mg, 6.6 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, $R_t$=16.8 min). The product was obtained as a white solid by lyophilization (2.81 mg, 88%). (ESI, MH$^+$) 427.2; ESI-HRMS (MH$^+$) calcd. for $C_{24}H_{23}N_6O_2$ 427.1882, found 427.1881.

Example 46

This example demonstrates the synthesis of 5-(4-(furan-2-yl)-1H-1,2,3-triazol-1-yl)-4'-(piperidin-4-yl)-[1,1'-biphenyl]-3-carboxylic acid (24nn) in an embodiment of the invention (FIG. 2).

To a solution of 23nn (3 mg, 5.7 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, $R_t$=19.8 min). The product was obtained as a white solid by lyophilization (2.28 mg, 84%). (ESI, MH$^+$) 415.2; ESI-HRMS (MH$^+$) calcd. for $C_{24}H_{23}N_4O_3$ 415.1770, found 415.1767, HPLC purity 98% ($R_t$=9.2 min).

Example 47

This example demonstrates the synthesis of 5-(4-(benzofuran-2-yl)-1H-1,2,3-triazol-1-yl)-4'-(piperidin-4-yl)-[1,1'-biphenyl]-3-carboxylic acid (24oo) in an embodiment of the invention (FIG. 2).

To a solution of 23oo (4 mg, 7 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, $R_t$=21.9 min). The product was obtained as a white solid by lyophilization, (ESI, MH$^+$) 465.2; ESI-HRMS (MH$^+$) calcd. for $C_{28}H_{25}N_4O_3$ 465.1927, found 465.1936.

Example 48

This example demonstrates the synthesis of 5-(4-(thiazol-2-yl)-1H-1,2,3-triazol-1-yl)-4'-(piperidin-4-yl)-[1,1'-biphenyl]-3-carboxylic acid (24pp) in an embodiment of the invention (FIG. 2).

A solution of 23pp (4.6 mg, 8.5 µmol) in of 2 mL MeOH:1.0 M KOH (1:1) was heated at 50° C. for 12 h. After removing the solvents under vacuum, the mixture was purified by preparative HPLC (Method B, $R_t$=18.7 min). The product was obtained as a white acetate salt by lyophilization (4.18 mg, 99%). (ESI, MH$^+$) 431.2; ESI-HRMS (MH$^+$) calcd. for $C_{23}H_{22}N_5O_2{}^{32}S$ 432.1494, found 432.1494, HPLC purity 96.4% ($R_t$=9.1 min).

Example 49

This example demonstrates the synthesis of 5-(4-cyclohexyl-1H-1,2,3-triazol-1-yl)-4'-(piperidin-4-yl)-[1,1'-biphenyl]-3-carboxylic acid (24qq) in an embodiment of the invention (FIG. 2).

To a solution of 23qq (5.4 mg, 9.9 µmol) in 2 mL of MeOH:H$_2$O (1:1), KOH (5.6 mg, 100 µmol) was added, and the resulting mixture was heated at 50° C. for 12 h. After removing the solvents under vacuum, the mixture was purified by preparative HPLC (Method B, $R_t$=21.2 min). The product was obtained as a white solid by lyophilization (2.65 mg, 55%). (ESI, MH$^+$) 431.3; ESI-HRMS (MH$^+$) calcd. for $C_{26}H_{31}N_4O_2$ 431.2447, found 431.2444. HPLC purity 97% ($R_t$=10.4 min).

Example 50

This example demonstrates the synthesis of 5-(4-cyclopropyl-1H-1,2,3-triazol-1-yl)-4'-(piperidin-4-yl)-[1,1'-biphenyl]-3-carboxylic acid (24rr) in an embodiment of the invention (FIG. 2).

To a solution of 23rr (5.7 mg, 11.5 μmol) in 2 mL of MeOH:H$_2$O (1:1), KOH (5.6 mg, 100 μmol) was added, and the resulting mixture was heated at 50° C. for 12 h. After removing the solvents under vacuum, the mixture was purified by preparative HPLC (Method B, R$_t$=12.6 min). The product was obtained as a white solid by lyophilization (5.1 mg, 99%). (ESI, MH$^+$) 389.2; ESI-HRMS (MH$^+$) calcd. for C$_{23}$H$_{25}$N$_4$O$_2$ 389.1978, found 389.1971.

Example 51

Figure 3:
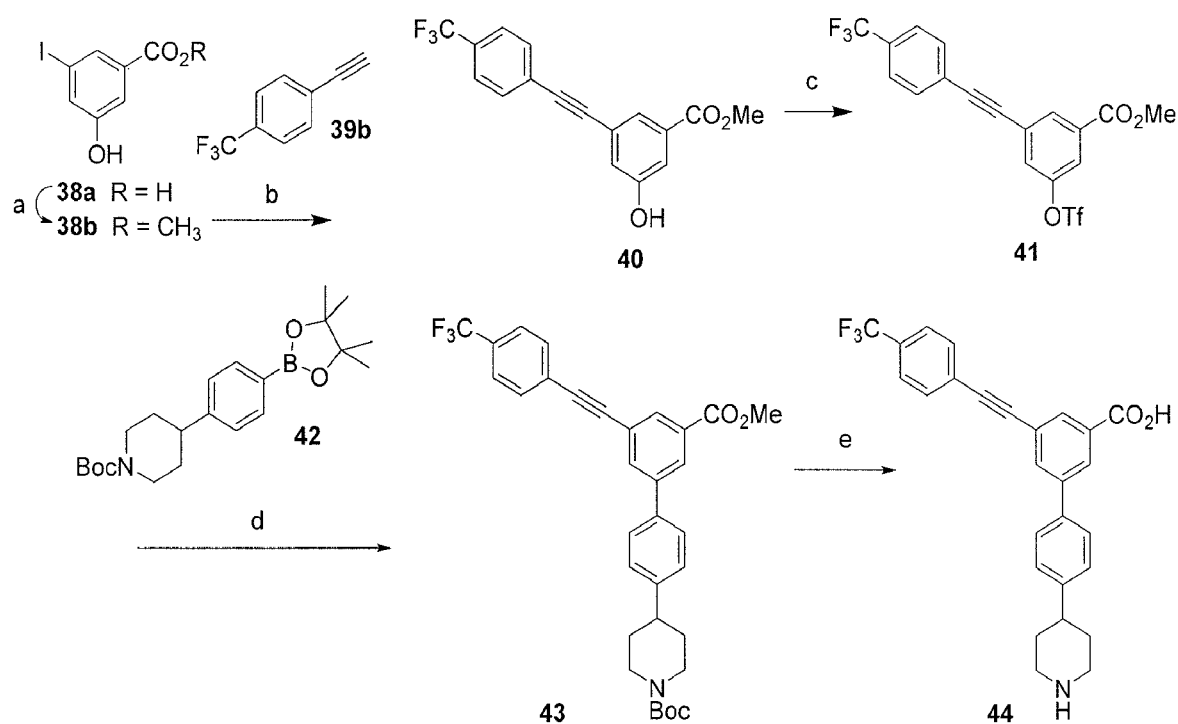
FIG. 3 is a chemical scheme of the synthesis of alkynyl derivative 44 as a $P2Y_{14}R$ antagonist. Reagents and conditions: a. $CH_3OH$, $SOCl_2$, 0 to 23° C. (33%); b. 1-ethynyl-4-(trifluoromethyl)benzene, CuI, $PdCl_2(PPh_3)_2$, DMF, $(C_2H_5)_3N$, 0 to 23° C. (81%); c. $(CF_3SO_2)_2O$, $(C_2H_5)_3N$, $CH_2Cl_2$ (98%); d. tert-butyl 4-(4-(4,4,5,5-tetramethyl-1,3,2-dioxaborolan-2-yl)phenyl)piperidine-1-carboxylate, $Pd(PPh_3)_4$, $K_2CO_3$, DMF (67%); e. LiOH (aqueous 0.5M), $CH_3OH$ reflux, then HCl (aqueous 1M), pH 1 (28%).

This example demonstrates the synthesis of 4'-(piperidin-4-yl)-5-((4-(trifluoromethyl)phenyl)ethynyl)-[1,1'-biphenyl]-3-carboxylic acid hydrochloride (44) in an embodiment of the invention (FIG. 3).

3-Hydroxy-5-iodobenzoic acid (38a, 264 mg, 1 mmol) was suspended in methanol (3 mL), and the solution was cooled to 0° C. in an ice bath. Thionyl chloride (0.5 mL, 7 mmol) was added to the mixture over the course of 30 min at 0° C. The mixture was allowed to warm to room temperature and stirred for 16 h. The solvent was removed from the resulting light yellow solution under vacuum and the residue was redissolved in dichloromethane (3 mL). The solution was washed with saturated aqueous sodium bicarbonate solution (1 mL) and water (1 mL). The organic layer was dried with sodium sulfate and filtered through a pad of silica gel eluting with additional volume of dichloromethane. The combined eluants were evaporated to dryness to provide 38b (92 mg, 33%). $^1$H NMR (400 MHz, CDCl$_3$) δ 7.94 (s, 1H), 7.54 (s, 1H), 7.44 (s, 1H), 5.68 (s, 1H), 3.93 (s, 3H). $^{13}$C NMR (101 MHz, CDCl$_3$) δ 165.9, 156.3, 132.6, 130.9, 129.2, 116.1, 93.9, 52.7. Positive ESI-MS (m/z) 279.

1-Ethynyl-4-(trifluoromethyl)benzene (39b, 102 mg, 0.6 mmol) was added to a degassed suspension of 38b (110 mg, 0.4 mmol), bis(triphenylphosphine)palladium(II) dichloride (14 mg, 5 mol %) and copper(I) iodide (4 mg, 5 mol %) and triethylamine (0.3 mL, mmol) in anhydrous DMF (6 mL) at 0° C. The reaction mixture was allowed to warm up to stirred until the complete consumption of 38b. The reaction mixture was quenched with water (25 mL) and the organic products were extracted with ethyl acetate (3×5 mL). The combined extracts were washed with water (2×5 mL), brine (5 mL), dried with sodium sulfate and evaporated to dryness. The residue of evaporation was subjected to column chromatography (silica gel), eluting with chloroform/methanol 90/10 (v/v) mixture, to provide 40 (103 mg, 81%). $^1$H NMR (400 MHz, CDCl$_3$) δ 7.80 (t, J=1.38 Hz, 1H), 7.63 (s, 4H), 7.60 (dd, J=1.51, 2.51 Hz, 1H), 7.24 (dd, J=1.51, 2.51 Hz, 1H), 6.06 (br. s., 1H), 3.95 (s, 3H). $^{13}$C NMR (101 MHz, CDCl$_3$) δ 166.5, 155.9, 131.9, 131.7, 126.6, 125.4, 125.3, 125.3, 124.2, 122.8, 117.1, 116.1, 90.3, 88.7, 52.6. Positive ESI-MS (m/z) 321.

Trifluoromethanesulfonic anhydride (54 μL, 0.32 mmol) was added to a solution of 40 (93 mg, 0.29 mmol) and triethylamine (61 μL, 0.43 mmol) in anhydrous dichloromethane (2 mL) at −20° C. under inert atmosphere. The reaction mixture was removed from cooling bath and left to stir at 23° C. for 2.5 h. The solution was diluted with dichloromethane (3 mL), washed with water (1 mL), saturated aqueous sodium bicarbonate solution (1 mL), dried with sodium sulfate and evaporated to dryness under vacuum. The residue following evaporation was subjected to column chromatography (silica gel), eluting with ethyl acetate/hexane 20/80 (v/v) mixture. The combined fractions containing 41 were evaporated to dryness to afford product (128 mg, 98%). $^1$H NMR (400 MHz, CDCl$_3$) δ 8.25 (t, J=1.38 Hz, 1H), 7.92 (dd, J=1.38, 2.38 Hz, 1H), 7.66 (s, 4H), 7.63 (s, 1H), 3.99 (s, 3H). Positive ESI-MS (m/z) 453.

A mixture of triflate 41 (25 mg, 56 μmol), tert-butyl 4-(4-(4,4,5,5-tetramethyl-1,3,2-dioxaborolan-2-yl)phenyl) piperidine-1-carboxylate (42, 22 mg, 56 μmol), tetrakis(triphenylphosphine)palladium(0) (127 mg, 0.11 mmol), potassium carbonate (15 mg, 0.11 mmol) and DMF (1 mL) was degassed and heated to 90° C. under the atmosphere of inert gas for 8 h. After cooling to 23° C., the solvent was removed under vacuum. The residue was resuspended in ethyl acetate (3 mL), washed with water (2×1 mL) and dried with sodium sulfate. Ethyl acetate was removed under vacuum, and the residue was subjected to column chromatography (silica gel), eluting with chloroform/methanol 95/5 (v/v) mixture to obtain the title compound 43 (21 mg, 67%). $^1$H NMR (400 MHz, CDCl$_3$) δ 7.86 (s, 1H), 7.56 (m, 4H), 7.46-7.49 (m, 1H), 7.29 (m, 5H), 5.36 (m, 2H), 3.94 (s, 3H), 2.84 (br. s., 2H), 2.71 (t, J=12.05 Hz, 1H), 1.86 (m, 2H), 1.68 (m, 2H), 1.50 (s, 9H). Positive ESI-MS (m/z) 564.

Lithium hydroxide (aqueous 0.5M, 70 μL, 25 μmol) was added to a solution of 43 (13 mg, 23 μmol) in methanol (0.2 mL), and the mixture was heated at reflux for 1.5 h. During this time 43 was completely consumed. The mixture was allowed to cool to 23° C. and acidified with hydrochloric acid (1M) until pH 1. The acidified mixture was stirred for additional 2 h before solvents were removed under vacuum. The residue was subjected to column chromatography (silica gel), eluting with chloroform/methanol/acetic acid 100/10/1 (v/v) mixture. Hydrochloric acid (1 M) was added to fractions containing the desired product and the solvent was removed under vacuum to provide the desired product 44 as a hydrochloride salt (3.1 mg, 28%). $^1$H NMR (400 MHz, DMSO-d$_6$) δ 8.24 (s, 1H), 8.11 (t, J=1.63 Hz, 1H), 8.08 (s, 1H), 7.85 (s, 1H), 7.79 (td, J=1.51, 7.78 Hz, 1H), 7.73 (td, J=1.38, 7.53 Hz, 1H), 7.69 (d, J=8.03 Hz, 2H), 7.41 (t, J=7.65 Hz, 1H), 7.35 (d, J=8.28 Hz, 2H), 3.26 (br. s., 2H), 3.10-3.19 (m, 2H), 2.87 (d, J=12.55 Hz, 3H), 2.42 (dt, J=2.64, 7.22 Hz, 2H), 2.33 (td, J=1.79, 3.70 Hz, 1H). Positive ESI-MS (m/z) 450.

Example 52

The synthesis of fluorescent antagonist 4 as previously reported (Kiselev et al., *ACS Chem. Biol.* 2014, 9, 2833-2842) suffered from a low yield in the final click cycloaddition step to link the azide-functionalized fluorophore and the alkyne-functionalized pharmacophore. For the purpose of screening antagonist analogues, larger quantities of a fluorescent probe were needed. Therefore, an alternate route to 4 was designed and also explored another fluorescent antagonist analogue for possible use in screening. Given the unusually high affinity of 4 and its low nonspecific character, an alternate synthesis of the same probe was developed, in addition to modifying its structure, in order to provide a sufficient supply of 4 for use in routine assays. See FIGS. 4A and 4B.

Figure 4A:
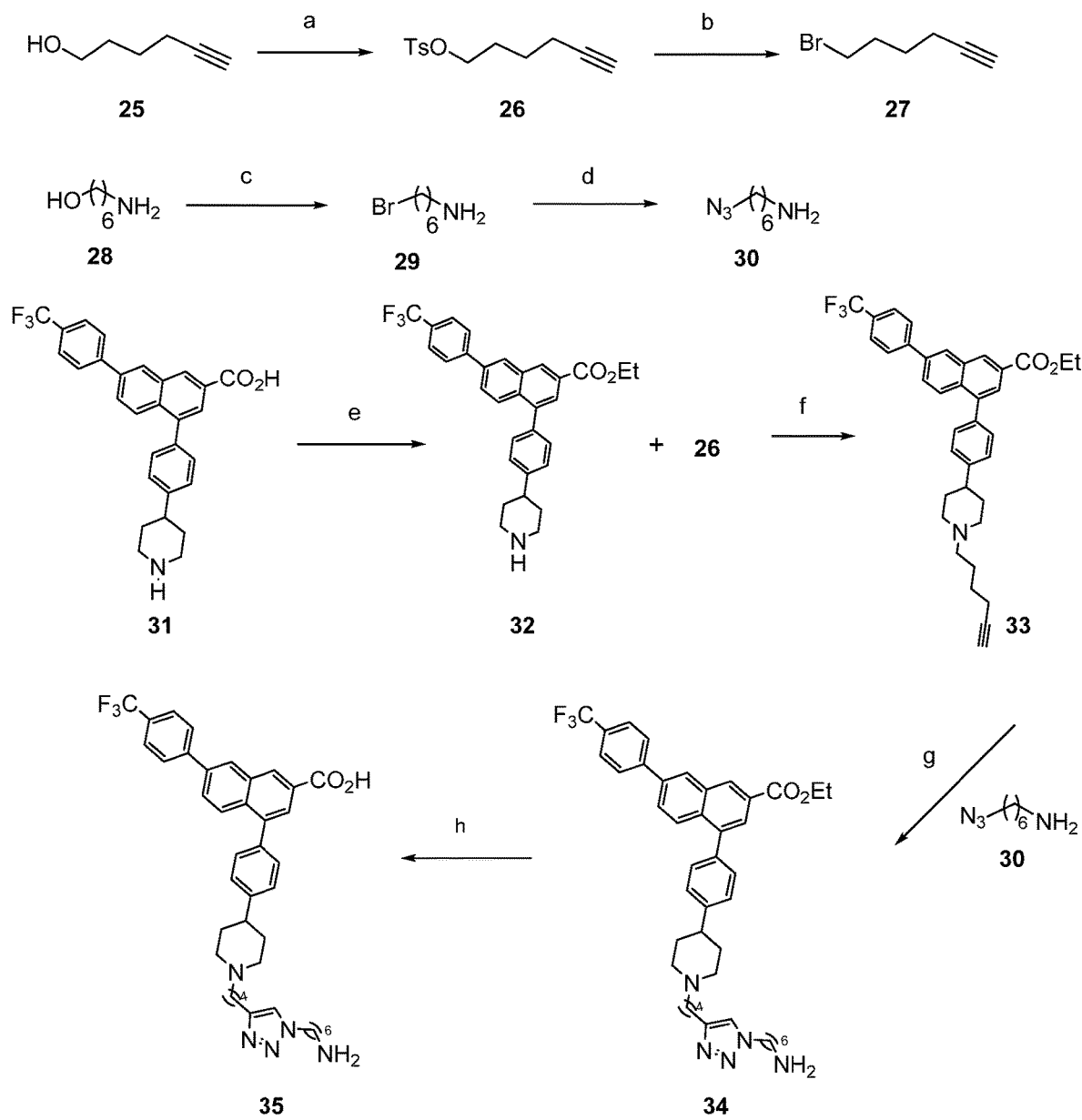
FIG. 4A is a chemical scheme of the synthesis of ethyl 4-(4-(1-(4-(1-(6-aminohexyl)-1H-1,2,3-triazol-4-yl)butyl)piperidin-4-yl)phenyl)-7-(4-(trifluoromethyl)phenyl)-2-naphthoate (34) and 4-(4-(1-(4-(1-(6-aminohexyl)-1H-1,2,3-triazol-4-yl)butyl)piperidin-4-yl)phenyl)-7-(4-(trifluoromethyl)phenyl)-2-naphthoic acid (35) in accordance with an embodiment of the invention. Reagents and conditions: a. TsCl, $NEt_3$, DMAP, $CH_2Cl_2$, r.t. 15 h (88%); b. LiBr, DMF, r.t., 12 h (82%); c. HBr 48% sol., 80° C., 20 h (61%); d. $NaN_3$, $H_2O$, reflux, 12 h (80%); e. $SOCl_2$, EtOH, 0° C. to r.t. (78%); f. $K_2CO_3$, DMF (92%); g. $CuSO_4$ (15 mol %), sodium ascorbate (45 mol %), t-BuOH: $H_2O$: $CH_2Cl_2$ (51%); h. LiOH (aqueous 0.5M), $CH_3OH$ reflux, then HCl (aqueous 1M), pH 1 (21%).

This example demonstrates the synthesis of the intermediate hex-5-yn-1-yl 4-methylbenzenesulfonate (26) in an embodiment of the invention (FIG. 4A).

To a solution of hex-5-yn-1-ol 25 (0.84 mL, 7.64 mmol), triethylamine (1.28 mL, 9.17 mmol), and 4-(dimethylamino) pyridine (20 mg, 0.15 mmol) in dichloromethane (DCM) (25 mL) at 0° C. was added p-toluenesulfonyl chloride (1.53 g, 8.02 mmol) in three portions. The reaction mixture was brought to room temperature and stirred for 15 h. Aqueous NaOH (1 N, 15 mL) was added, and the mixture was vigorously stirred for 15 min at room temperature. The usual workup (DCM, brine) gave the title compound (1.68 g, 88%) as a yellowish oil. $^1$H NMR (400 MHz, CDCl$_3$) δ: 1.42-1.48 (2H, m), 1.65-1.68 (2H, m), 1.84 (1H, J=4, t), 2.05-2.09 (2H, m), 2.31 (3H, s), 3.96 (2H, J=6, t), 7.26 (2H, J=8.0, d), 7.69 (2H, J=8.0, d). $^{13}$C NMR (100 MHz, CDCl$_3$) δ: 17.7, 21.6, 24.2, 27.7, 69.0, 69.9, 83.4, 127.0, 129.9, 133.0, 144.8.

Example 53

This example demonstrates the synthesis of the intermediate 6-bromohex-1-yne (27) in an embodiment of the invention (FIG. 4A).

LiBr (1.7 g, 19.6 mmol) was added to a stirred solution of 26 (1.64 g, 6.52 mmol) in dry DMF (20 mL). After the exothermic reaction, the mixture was stirred at room temperature for 24 h. Then, water (25 mL) was added and the aqueous phase extracted with Et$_2$O (3×25 mL). The collected organic fractions were dried over Na$_2$SO$_4$, filtered and concentrated in vacuo. The residue was purified by flash chromatography using as eluant Hex:EtOAc (5:1) to afford a colorless oil (0.86 g, 82%). $^1$H NMR (400 MHz, CDCl$_3$) δ: 1.66-1.70 (2H, m), 1.90-1.98 (3H, m), 2.24 (2H, m), 3.59 (2H, J=6.4, t). 13C NMR (100 MHz, CDCl$_3$) δ: 19.7, 29.4, 29.7, 45.6, 69.2, 83.8.

Example 54

This example demonstrates the synthesis of the intermediate 6-bromohexan-1-amine hydrochloride (29) in an embodiment of the invention (FIG. 4A).

6-Aminohexanol 28 (0.5 g, 4.27 mmol) was slowly added to a stirring 48% hydrogen bromide solution (5.1 mL) at 0° C., and the resulting mixture was stirred at 80° C. for 20 h. The mixture was neutralized by adding NaOH 2N (20 mL) and extracted with EtOAc (3×20 mL). The combined organic fraction was washed with water (50 mL) followed by brine (50 mL) and then dried over Na$_2$SO$_4$, filtered, and concentrated in vacuo. The obtained viscous oil was then dissolved in 4M hydrogen chloride solution in dioxane to give a sticky solid that was washed with Et$_2$O and then filtered for affording to a yellowish solid (0.55 g, 61%). $^1$H NMR (400 MHz, MeOD) δ:1.42-1.46 (4H, m), 1.59-1.70 (2H, m), 1.74-1.82 (2H, m), 2.86 (2H, J=8, t), 3.39 (2H, J=4, t). $^{13}$C NMR (100 MHz, MeOD) δ: 25.2, 27.0, 27.2, 32.2, 32.8, 44.2.

Example 55

This example demonstrates the synthesis of the intermediate 6-azidohexan-1-amine (30) in an embodiment of the invention (FIG. 4A).

To a solution of 29 (0.55 g, 2.54 mmol) in water (25 mL), NaN$_3$ (0.49 g, 7.69 mmol) was added and the resulting mixture was heated at 100° C. for 12 h. After cooling, 37% ammonia solution was added until a basic pH was reached, and the aqueous phase was extracted with Et$_2$O (3×20 mL). The organic fractions were collected, dried over Na$_2$SO$_4$ and filtered, and the solvent removed under vacuum to give a yellow oil (0.29 g, 80%). $^1$H NMR (400 MHz, CDCl$_3$) δ:1.29-1.34 (4H, m), 1.35-1.40 (2H, m), 1.50-1.54 (2H, m), 2.15 (2H, br s), 2.62 (2H, J=4, t), 3.18 (2H, J=8.0, t). $^{13}$C NMR (100 MHz, CDCl$_3$) δ: 26.4, 26.6, 28.8, 33.1, 41.8, 51.4

Example 56

This example demonstrates the synthesis of ethyl 4-(4-(piperidin-4-yl)phenyl)-7-(4-(trifluoromethyl)phenyl)-2-naphthoate (32) in an embodiment of the invention (FIG. 4A).

To a solution of 31 (0.50 g, 1.57 mmol) in EtOH (50 mL), thionyl chloride (1.37 mL, 18.84 mmol) was carefully added over 30 min at 0° C. The reaction was allowed to warm up at room temperature and stirred overnight. The resulting mixture was quenched by adding 5% solution NaOH (25 mL) until basic pH. Then, the solvent was evaporated under vacuum, and the aqueous residue was extracted with EtOAc (3×20 mL). The collected organic fractions were dried over Na$_2$SO$_4$, filtered and the solvent was removed under vacuum. The residue was purified by chromatography using as eluant DCM/MeOH/NH$_4$OH (7:3:0.3). The title compound was obtained as a white solid (0.61 g, 78%). $^1$H NMR (400 MHz, MeOD) δ: 1.35 (3H, J=4 Hz, t), 1.65-1.69 (2H, m), 1.81-1.84 (2H, m), 2.73-2.79 (3H, m), 3.15-3.19 (2H, m), 4.35 (2H, J=8 Hz, q), 7.33-7.37 (4H, m), 7.69 (2H, J=8 Hz, d), 7.76-7.79 (1H, m), 7.83-7.90 (4H, m), 8.26 (1H, s), 8.58 (1H, s). m/z (ESI, MH$^+$) 504; ESI-HRMS (MH$^+$) calcd. for C$_{31}$H$_{29}$F$_3$NO$_2$ 504.2150, found 504.2150.

Example 57

This example demonstrates the synthesis of ethyl 4-(4-(1-(hex-5-yn-1-yl)piperidin-4-yl)phenyl)-7-(4-(trifluoromethyl)phenyl)-2-naphthoate (33) in an embodiment of the invention (FIG. 4A).

K$_2$CO$_3$ (0.12 g, 0.9 mmol) was added to a stirring solution of 32 (0.15 g, 0.3 mmol) in dry dimethylformamide (DMF) (15 mL), and the resulting mixture was left stirring for 20 min. Compound 26 (0.06 g, 0.6 mmol) was subsequently added, and the reaction mixture was first stirred at room temperature for 2h and then at 50° C. for 2.5h. After cooling at room temperature, NaHCO$_3$ saturated solution (15 mL) was added, and the aqueous phase was extracted with EtOAc (3×20 mL). The collected organic fractions were dried over Na$_2$SO$_4$, filtered and the solvent removed under vacuum. The residue was purified by chromatography using as eluant DCM/MeOH/NH$_4$OH (9.5:0.5:0.05). The desired compound was obtained as a colorless oil (0.16 g, 92%). m/z $^1$H NMR (400 MHz, CDCl$_3$) δ: 1.38 (3H, J=4 Hz, t), 1.51-1.55 (2H, m), 1.65-1.69 (2H, m), 1.90-1.99 (4H, m), 2.06-2.17 (5H, m), 2.40-2.44 (2H, m), 2.56-2.59 (1H, m), 3.10-3.13 (2H, m), 4.38 (2H, J=8 Hz, q), 7.33 (2H, J=8 Hz, d), 7.38 (2H, J=8 Hz, d), 7.67-7.70 (3H, m), 7.71-7.76 (2H, m), 7.91-7.95 (2H, m), 8.15 (1H, s), 8.60 (1H, s) (ESI, MH$^+$) 584. $^{13}$C NMR (101 MHz, CDCl3) δ 14.42, 18.35, 25.69, 25.77, 26.49, 29.71, 32.99, 42.33, 54.27, 58.31, 61.26, 68.58, 84.31, 125.89, 126.65, 126.99, 127.11, 127.44, 127.94, 128.03, 129.55, 130.07, 130.61, 133.30, 137.61, 140.47, 143.91, 166.56. (ESI, MH$^+$) 584; ESI-HRMS (MH$^+$) calcd. for C$_{37}$H$_{37}$F$_3$NO$_2$ 584.2783, found 584.2776.

Example 58

This example demonstrates the synthesis of ethyl 4-(4-(1-(4-(1-(6-aminohexyl)-1H-1,2,3-triazol-4-yl)butyl)piperidin-4-yl)phenyl)-7-(4-(trifluoromethyl)phenyl)-2-naphthoate (34) in an embodiment of the invention (FIG. 4A).

To a solution of 33 (50 mg, 0.09 mmol) in DCM:t-BuOH:H$_2$O (1:1:1) (2 mL), compound 30 was added, followed by copper (II) sulfate pentahydrate (15 mol %) and sodium ascorbate (45 mol %). The reaction mixture was stirred for 24 h at room temperature. The solvents were removed under vacuum and the residue rinsed with 37% ammonia solution (5 mL) and extracted with EtOAc (3×8 mL). The collected organic fractions were dried over Na$_2$SO$_4$, filtered, and the solvent was removed under vacuum. The residue was purified by chromatography using as eluant a gradient of DCM/MeOH/NH$_4$OH (from 9.5:0.5:0.05 to 7:3:0.3). The title product was obtained as a white solid (32 mg, 51%). $^1$H NMR (400 MHz, CDCl$_3$) δ: 1.35-1.39 (7H, m), 1.58-1.65 (6H, m), 1.83-1.88 (6H, m), 2.04-2.07 (2H, m), 2.39-2.42 (3H, m), 2.65-2.71 (6H, m) 3.09-3.17 (2H, m), 4.23-4.26 (2H, m), 4.38 (2H, J=8 Hz, q), 7.21-7.23 (1H, m), 7.30-7.33 (2H, m), 7.38-7.40 (2H, m), 7.66-7.70 (3H, m), 7.73-7.76 (2H, m), 7.96-7.99 (2H, m), 8.15 (1H, s), 8.62 (1H, s). (ESI, MH$^+$) 726; ESI-HRMS (MH$^+$) calcd. for C$_{43}$H$_{51}$F$_3$N$_5$O$_2$ 726.3984, found 726.3995.

Example 59

This example demonstrates the synthesis of 4-(4-(1-(4-(1-(6-aminohexyl)-1H-1,2,3-triazol-4-yl)butyl)piperidin-4-yl)phenyl)-7-(4-(trifluoromethyl)phenyl)-2-naphthoic acid (35) in an embodiment of the invention (FIG. 4A).

To a solution of 34 (32 mg, 44 µmol) in MeOH (1 mL), a solution of 0.5 M LiOH (1 mL) was added and the resulting mixture was heated at 60° C. and stirred overnight. After cooling, the solvents were evaporated and the residue purified by preparative HPLC(R$_t$=31.08 min). The product was obtained as a white solid by freeze drying (6.5 mg, 21%). $^1$H NMR (400 MHz, MeOD) δ: 1.26-1.33 (4H, m), 1.52-1.64 (6H, m), 1.81-1.86 (6H, m), 2.19-2.25 (2H, m), 2.46-2.50 (2H, m), 2.66-2.70 (3H, m), 2.79 (2H, J=8 Hz, t), 3.09-3.12 (2H, m), 4.30 (2H, J=8 Hz, t), 7.32 (2H, J=8 Hz, d), 7.38 (2H, J=8 Hz, d), 7.66-7.70 (3H, m), 7.70-7.72 (4H, m), 7.89-7.94 (4H, m), 8.27 (1H, s), 8.49 (1H, s). (ESI, MH$^+$) 698; ESI-HRMS (MH$^+$) calcd. for C$_{41}$H$_{47}$F$_3$N$_5$O$_2$ 698.3690, found 698.3682.

Example 60

Figure 4B:
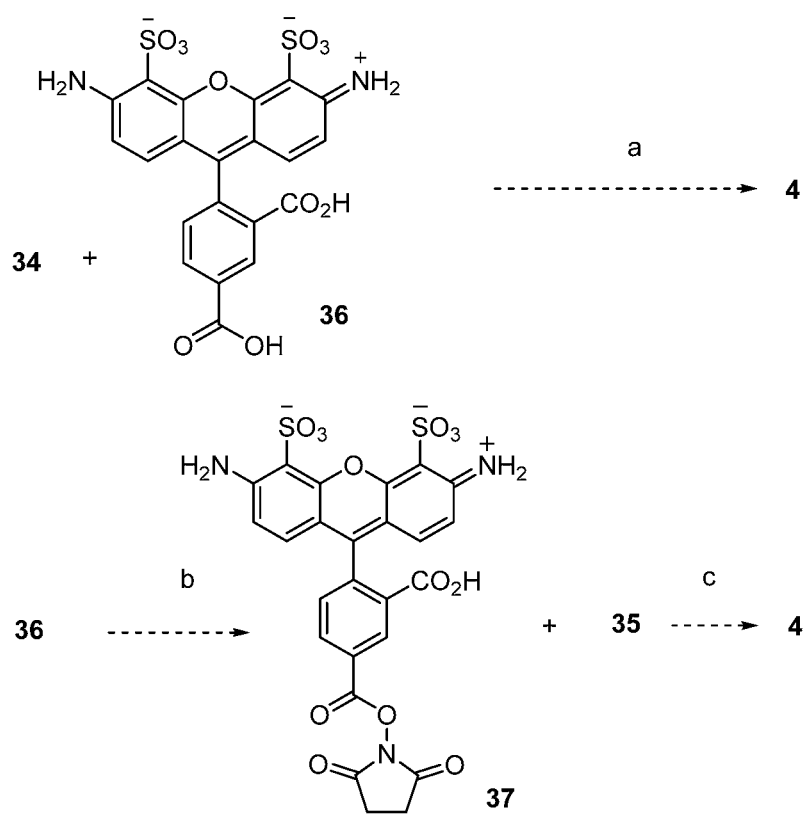
FIG. 4B is an improved chemical scheme of the synthesis of prior art compound 6-amino-9-(2-carboxy-4-((6-(4-(4-(4-(4-(3-carboxy-6-(4-(trifluoromethyl)phenyl)-naphthalen-1-yl)phenyl)piperidin-1-yl)butyl)-1H-1,2,3-triazol-1-yl)hexyl)carbamoyl)-phenyl)-3-iminio-5-sulfo-3H-xanthene-4-sulfonate (4). Reagents and conditions: a. 1) N,N,N',N'-tetramethyl-O—(N-succinimidyl)-uronium tetrafluoroborate (TSTU), N,N-diisopropylethylamine (DIPEA), dimethylformamide (DMF); 2) LiOH, 0.5 M, MeOH: $H_2O$; b. TSTU, DIPEA, DMF, water, 0° C.

This example demonstrates the synthesis of 6-amino-9-(2-carboxy-4-((6-(4-(4-(4-(4-(3-carboxy-6-(4-(trifluoromethyl)phenyl)-naphthalen-1-yl)phenyl)piperidin-1-yl)butyl)-1H-1,2,3-triazol-1-yl)hexyl)carbamoyl)-phenyl)-3-iminio-5-sulfo-3H-xanthene-4-sulfonate (4) (FIG. 4B).

The coupling of the AlexaFluor488 fluorophore and pharmacophore of formula (I) was attempted by two methods, either: 1) condensation of the fluorophore as a carboxylic acid 36 to the ethyl ester of 34 followed by ester saponification; or 2) by reaction of the fluorophore in situ activated as N-succinimidyl ester 37 with the carboxylic acid derivative 35. In particular, to a solution of AlexaFluor 488, 35 (4.44 mg, 7.08 µmol) and N,N-diisopropylethylamine (DIPEA) (1.34 µL, 7.72 µmol) in dry N,N-dimethylformamide (DMF) (400 µL), and N,N,N',N'-tetramethyl-O—(N-succinimidyl)-uronium tetrafluoroborate (TSTU) (2.42 mg, 7.72 µmol) was added at 0° C. The resulting mixture was allowed to warm up at room temperature and stirred for 2-3 h. Then, a solution of 34 (4.5 mg, 6.44 µmol) and DIPEA (1.30 µL, 7.08 µmol) in dry DMF (300 µL) was added and the reaction was stirred overnight at room temperature. After removal of the solvent, the residue was purified by preparative HPLC (Method A, R$_t$ 24.9 min). The product 4 was obtained as an orange solid after lyophilization (0.8 mg, 10%). (ESI, (M–H$^+$)$^-$) 1212; ESI-HRMS (M–H$^+$)$^-$ calcd. for C$_{62}$H$_{57}$F$_3$N$_2$O$_{12}$S$_2$ 1212.3462, found 1212.3459. HPLC purity 96.1% (R$_t$=5.7 min).

The second synthetic route provided compound 4 with an improved the reaction yield compared to the previous synthetic method (Kiselev et al., ACS Chem. Biol. 2014, 9, 2833-2842).

Example 61

This example demonstrates compounds of formula (I) assayed in a competition assay by flow cytometry using Chinese hamster ovary (CHO) cells expressing P2Y$_{14}$R and fluorescent antagonist ligand 4 as a tracer.

The following compounds of formula (I)

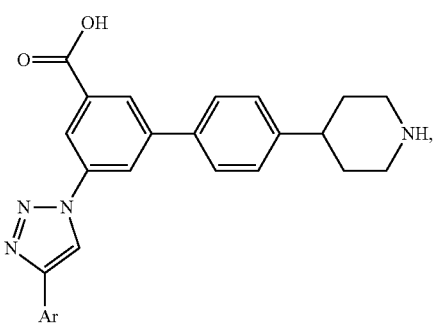

in which Ar is defined in Table 1 below, were subjected to docking and molecular dynamics simulation (10 ns) in a P2Y$_{14}$R homology model with 3 bound, which was refined using molecular dynamics (standard protocol), as detailed below.

P2Y$_{14}$R models were uploaded to the "Orientations of Proteins in Membranes (OPM)" database and a suggested orientation for each structure was provided based on the 2MeSADP-bound P2Y$_{12}$R orientation (PDB: 4PXZ) (Zhang et al., Nature 2014, 509, 119-122). Each receptor model was then positioned in a 1-palmitoyl-2-oleoyl-sn-glycero-3-phosphocholine (POPC) lipid bilayer (70 A×70 A) generated by a grid-based method using the VMD Membrane Plugin tool, and overlapping lipids within 0.6 A were removed upon combining the protein membrane system (Lomize et al., Bioinformatics 2006, 22, 623-5; and Sommer et al., Comput. Struct. Biotechnol. J. 2013, 5, e201302014). Each protein-membrane system was then solvated with TIP3P water using the Solvate 1.0 VMD Plugin tool and neutralized by 0.154 M Na+/Cl− counterions.

This study utilized the high-performance computational capabilities of the Biowulf Linux GPU cluster at the National Institutes of Health, Bethesda, Md. (http://biowulf-.nih.gov). Molecular dynamics simulations with periodic boundary conditions were carried out using Nanoscale Molecular Dynamics (NAMD) software and the CHARMM36 Force Field (Jorgensen et al., The Journal of Chemical Physics 1983, 79, 926-935; and Phillips et al., J Comput Chem 2005, 26, 1781-1802). The ligands were parameterized by analogy using the ParamChem service (1.0.0) and implementing the CHARMM General Force Field for organic molecules (3.0.1) (Best et al., Journal of Chemical Theory and Computation 2012, 8, 3257-3273; Vanommeslaeghe et al., J Comput. Chem. 2010, 31, 671-90; Vanommeslaeghe et al., J. Chem. Inf. Model. 2012, 52, 3144-3154; and Vanommeslaeghe et al., J Chem. Inf. Model.

2012, 52, 3155-3168) 10,000-step conjugate gradient minimization was initially performed to minimize steric clashes. The protein and ligand atoms were kept fixed during an initial 8 ns equilibration of the lipid and water molecules. Atom constraints were then removed and the entire system was allowed to equilibrate. The temperature was maintained at 300 K using a Langevin thermostat with a damping constant of 3 ps$^{-1}$. The pressure was maintained at 1 atm using a Berendsen barostat. An integration time step of 1 fs was used, while hydrogen-oxygen bond lengths and hydrogen-hydrogen angles in water molecules were constrained using the SHAKE algorithm (Ryckaert et al., *J Comput. Phys.* 1977, 23, 327-341). VMD 1.9 was used for trajectory analysis and movie making. The PyMOL Molecular Graphics System, Version 1.6.0 Schrodinger, LLC was used for making figures. Each structure was simulated for 30 ns without constraints. Root-mean-square deviation (RMSD) plots for ligand atoms during the 30 ns trajectories were used to compare relative ligand stability in the binding pocket during simulation, and thus used to refine initial ranking scores from ligand docking.

TABLE 1

| Compound Identifier | Ar | P2Y$_{14}$R affinity$^a$ (μM) or % inhibition at 3 μM |
|---|---|---|
| 3 PPTN | n/a | 92.6 ± 1.2% |
| 24a MRS4218 | 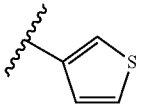 | 30.1 ± 2.1% |
| 24b MRS4217 | 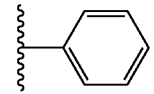 | 92.3 ± 0.5% |
| 24c MRS4228 | 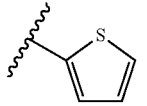 [SMILES: *c1cccs1] | 67.2 ± 2.2% |
| 24d MRS4235 |  | 14.5 ± 2.1% |
| 24e MRS4226 | 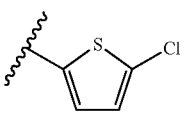 [SMILES: *c1ccc(Cl)s1] | 21.2 ± 2.9% |
| 24f AJ139 MRS4244 | 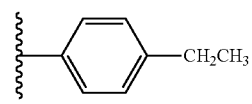 | 26.5 ± 5.2% |
| 24g AJ137D MRS4242 | 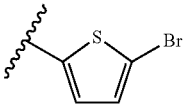 | 82.7 ± 1.5% |
| 24h AJ136D MRS4241 | 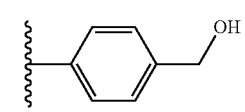 | 88.8 ± 0.8% |

TABLE 1-continued

| Compound Identifier | Ar | P2Y$_{14}$R affinity$^a$ (μM) or % inhibition at 3 μM |
|---|---|---|
| 24i | 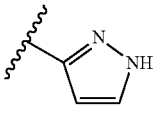 | 67.3 ± 2.5% |
| 24j MRS4225 | 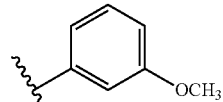 | 44.2 ± 1.9% |
| 24k MRS4219 | 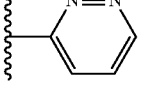 | 66.2 ± 2.0% |
| 24-l AJ144 MRS4261 |  | 93.1 ± 0.8% |
| 24m | 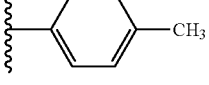 | NS |
| 24n | 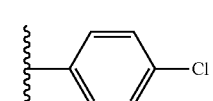 | NS |
| 24o MRS4227 | 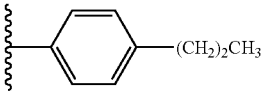 | 75.1 ± 2.8% |
| 24p | 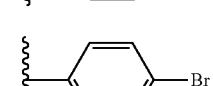 | 91.5 ± 0.3% |
| 24q | 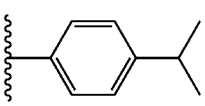 | 87.1 ± 0.5% |
| 24r MRS4236 | 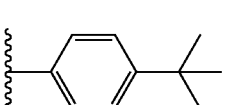 | 88.9 ± 4.6% |
| 24t MRS4229 | 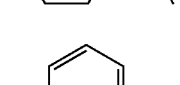 | 79.0 ± 2.2% |
| 24u MRS4232 | 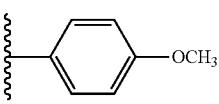 [SMILES: *c1ccc(OC)cc1] | 39.6 ± 7.4% |

TABLE 1-continued

| Compound Identifier | Ar | P2Y$_{14}$R affinity$^a$ (μM) or % inhibition at 3 μM |
|---|---|---|
| 24v | 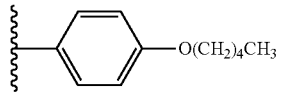 4-O(CH$_2$)$_4$CH$_3$ phenyl | 85.2 ± 0.8% |
| 24w MRS4233 | 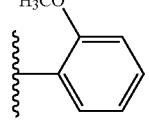 2-OCH$_3$ phenyl | 13.7 ± 3.1% |
| 24x MRS4230 | 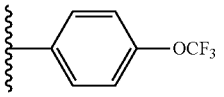 [SMILES: *c1ccc(OC(F)(F)F)cc1] 4-OCF$_3$ phenyl | 86.7 ± 1.0% |
| 24y | 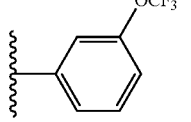 3-OCF$_3$ phenyl | 65.3 ± 4.5% |
| 24z AJ138D MRS4243 | 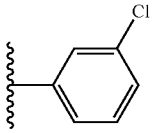 [SMILES: *c1cccc(Cl)c1] 3-Cl phenyl | 49.9 ± 2.2% |
| 24aa AJ122D MRS4237 | 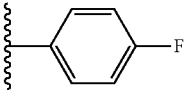 [SMILES: *c1ccc(F)cc1] 4-F phenyl | 65.2 ± 1.2% |
| 24bb AJ134D MRS4238 | 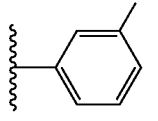 3-F phenyl | 37.3 ± 4.6% |
| 24cc MRS4239 | 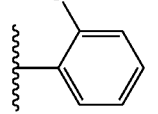 2-F phenyl | 42.2 ± 4.3% |
| 24dd | 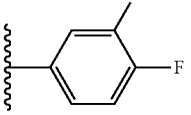 3,4-diF phenyl | 85.0 ± 0.6% |
| 24ee AJ135D MRS4240 | 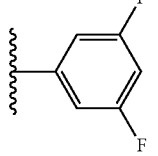 3,5-diF phenyl | 76.2 ± 1.7% |
| 24ff AJ142 MRS4259 | 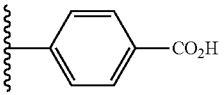 [SMILES: *c1ccc(C(=O)O)cc1] 4-CO$_2$H phenyl | 33.4 ± 1.3% |
| 24gg AJ143 MRS4260 | 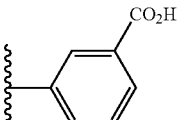 3-CO$_2$H phenyl | 35.7 ± 0.7% |
| 24hh | 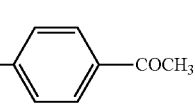 4-COCH$_3$ phenyl | 69.3 ± 3.8% |
| 24ii | 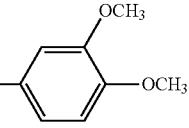 3,4-diOCH$_3$ phenyl | 33.6 ± 3.5% |
| 24jj AJ141 MRS4258 | 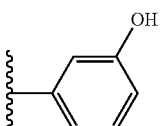 3-OH phenyl | 11.6 ± 1.2% |
| 24kk AJ140 MRS4245 | 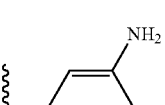 3-NH$_2$ phenyl | 14.0 ± 5.1% |
| 24-ll | 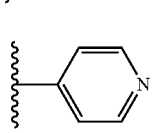 pyridyl | 13.1 ± 2.6% |
| 24mm MRS4231 | 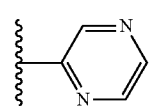 [SMILES: *c1cnccn1] pyrazinyl | 18.1 ± 5.8% |
| 24nn AJ145 MRS4262 | 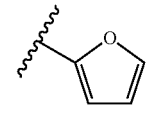 [SMILES: *c1ccco1] furyl | 32.4 ± 2.7% |
| 24oo | 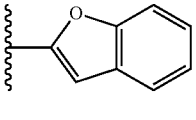 [SMILES: *c1cc2ccccc2o1] benzofuranyl | 73.4 ± 3.1% |
| 24pp MRS4234 | 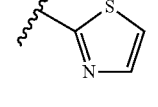 thiazolyl | 6.0 ± 1.3% |
| 24qq AJ146 MRS4263 | 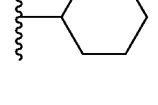 cyclohexyl | 53.1 ± 2.0% |

TABLE 1-continued

| Compound Identifier | Ar | $P2Y_{14}R$ affinity[a] (μM) or % inhibition at 3 μM |
|---|---|---|
| 24rr | (structure) | 50.1 ± 1.9% |

[a] % inhibition at 3 μM of binding of fluorescent antagonist 4 (20 nM) in $P2Y_{14}R$—CHO cells
NS: not synthesized The affinities of the various analogues were determined by the foregoing method, which provided sigmoidal concentration response curves displaying a smooth concentration dependence of the inhibition. For example, the 5-chlorothienyl analogue 24k displayed an $IC_{50}$ value of 0.73 μM. The rank order of potency was: 24k>24a≥24b.

Example 62

This example demonstrates the proposed synthesis of a dendron conjugate comprising a compound of formula (I) in an embodiment of the invention.

Figure 5:
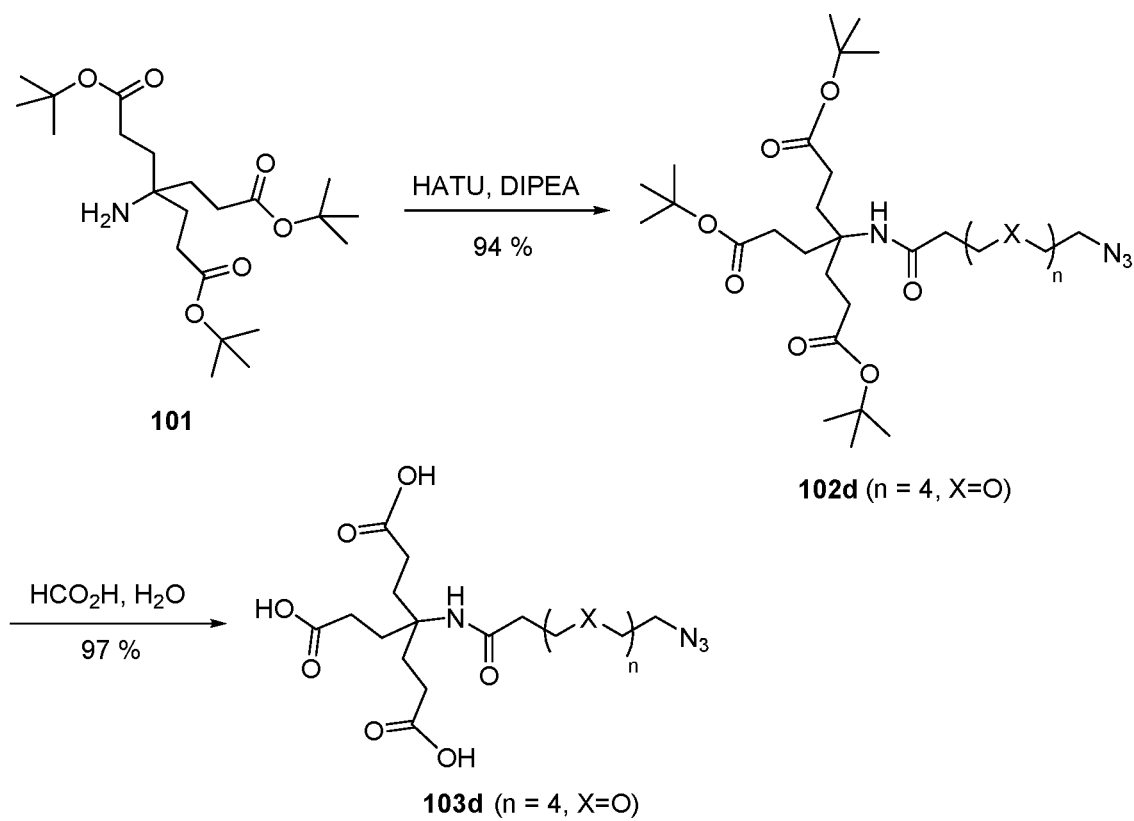
FIG. 5 is a chemical scheme of the proposed synthesis of dendron precursor 103d. X is O, NH, or $CH_2$, and n ranges from 0-36.
Figure 6:
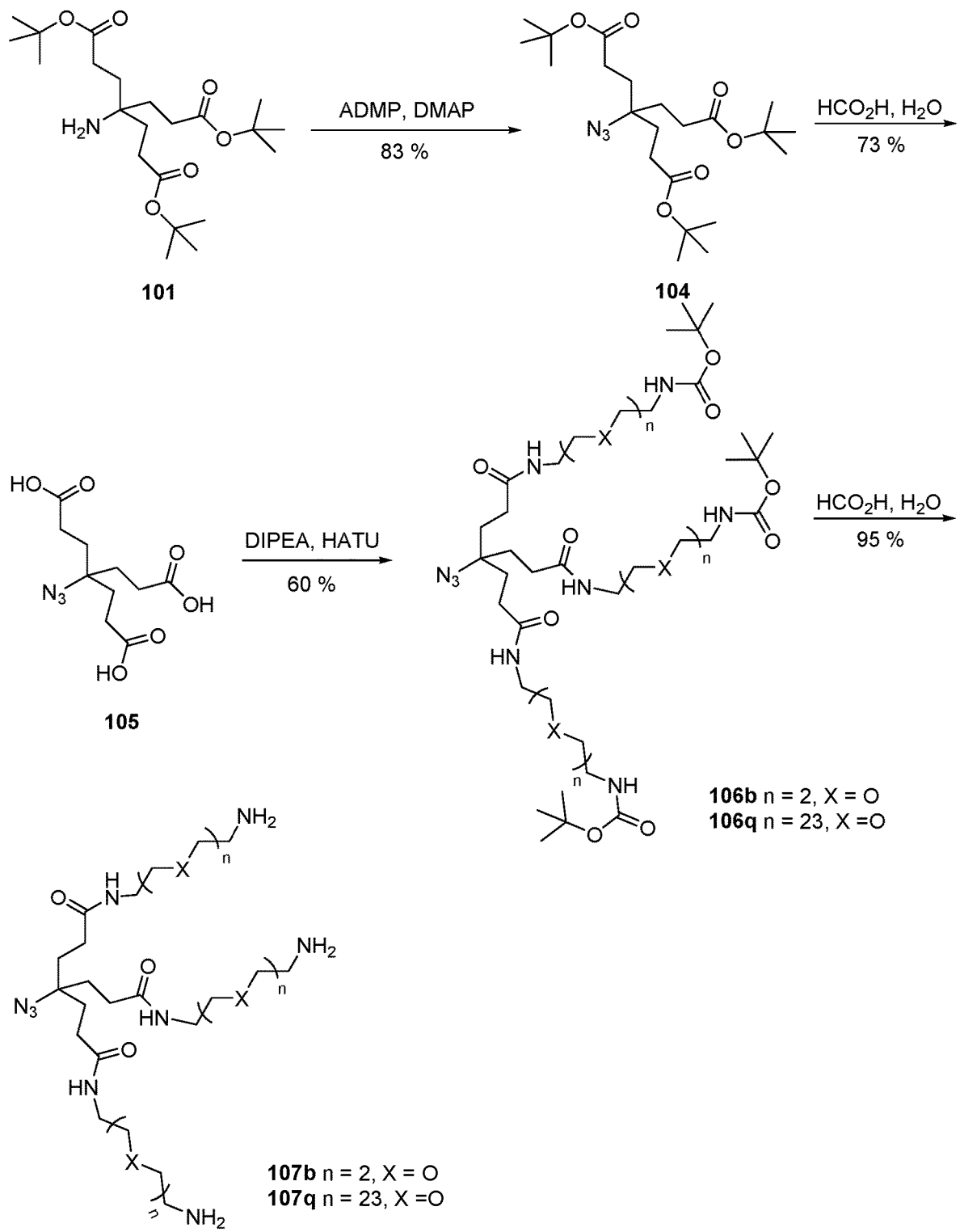
FIG. 6 is a chemical scheme of the proposed synthesis of dendron precursors 107b and 107q. X is O, NH, or $CH_2$, and n ranges from 0-36.

The proposed syntheses of precursors are set forth in FIGS. 5 and 6. The synthesis of compound 101 was previously published in WO 93/21144; Newkome et al., *J. Org. Chem.* 1991, 56, 7162; and Newkome et al., *J. Org. Chem.* 1992, 57, 358. For compounds (e.g., 102d, 103d), the letter defines the number of repeat units, as defined in Table 2.

TABLE 2

| Compound | n |
|---|---|
| 102a | 0 |
| 103a | |
| 106a | |
| 107a | |
| 102b | 2 |
| 103b | |
| 106b | |
| 107b | |
| 102c | 3 |
| 103c | |
| 106c | |
| 107c | |
| 102d | 4 |
| 103d | |
| 106d | |
| 107d | |
| 102e | 5 |
| 103e | |
| 106e | |
| 107e | |
| 102f | 6 |
| 103f | |
| 106f | |
| 107f | |
| 102g | 8 |
| 103g | |
| 106g | |
| 107g | |
| 102h | 10 |
| 103h | |
| 106h | |
| 107h | |
| 102i | 12 |
| 103i | |
| 106i | |
| 107i | |
| 102j | 11 |
| 103j | |
| 106j | |
| 107j | |
| 102k | 14 |
| 103k | |
| 106k | |
| 107k | |
| 102l | 15 |
| 103l | |
| 106l | |
| 107l | |
| 102m | 16 |
| 103m | |
| 106m | |
| 107m | |
| 102n | 18 |
| 103n | |
| 106n | |
| 107n | |
| 102o | 20 |
| 103o | |
| 106o | |
| 107n | |
| 102p | 22 |
| 103p | |
| 106p | |
| 107p | |
| 102q | 23 |
| 103q | |
| 106q | |
| 107q | |
| 102r | 24 |
| 103r | |
| 106r | |
| 107r | |
| 102s | 26 |
| 103s | |
| 106s | |
| 107s | |
| 102t | 28 |
| 103t | |
| 106t | |
| 107t | |
| 102u | 30 |
| 103u | |
| 106u | |
| 107u | |
| 102v | 32 |
| 103v | |
| 106v | |
| 107v | |
| 102w | 34 |
| 103w | |
| 106w | |
| 107w | |
| 102x | 36 |
| 103x | |
| 106x | |
| 107x | |

Figure 7:
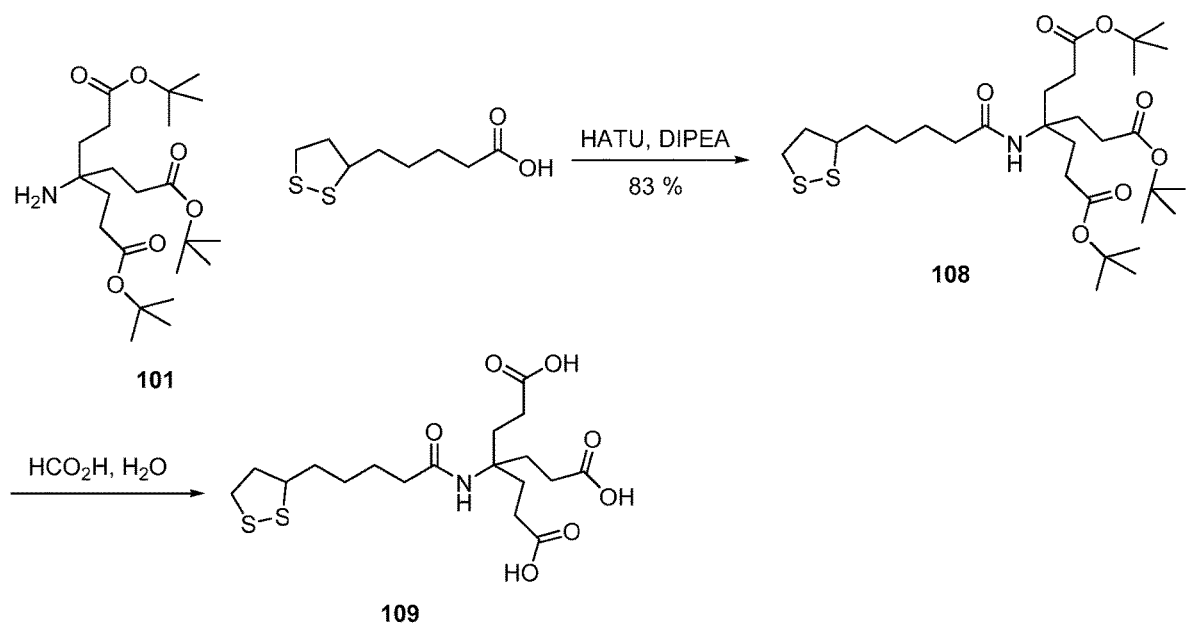
FIG. 7 is a chemical scheme of the proposed synthesis of dendron precursor 109.
Figure 8:
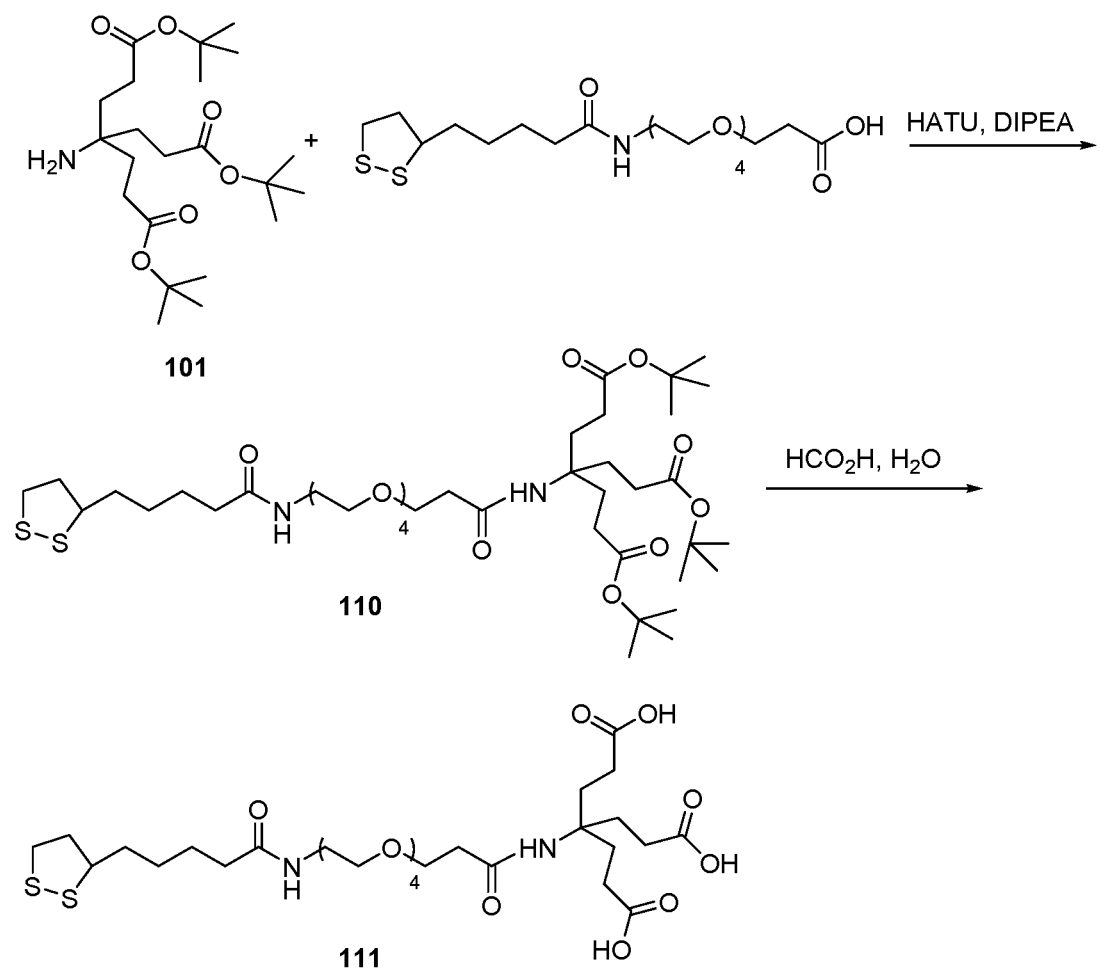
FIG. 8 is a chemical scheme of the proposed synthesis of dendron precursor 111.

Dendrons 109 and 111 comprising a lipoic acid residue as the reactive sulfur-containing moiety ($X^5$) is shown in FIGS. 7 and 8. Synthesis of dendrons 108 and 109 was previously described in WO 2005/075453; Cho et al., *Chem. Mater.* 2011, 23, 2665-2676; Cho et al., *Langmuir* 2014, 30, 3883-3893; and Tsai et al., *Nanoscale* 2013, 5, 5390-5395.

Figure 9A:
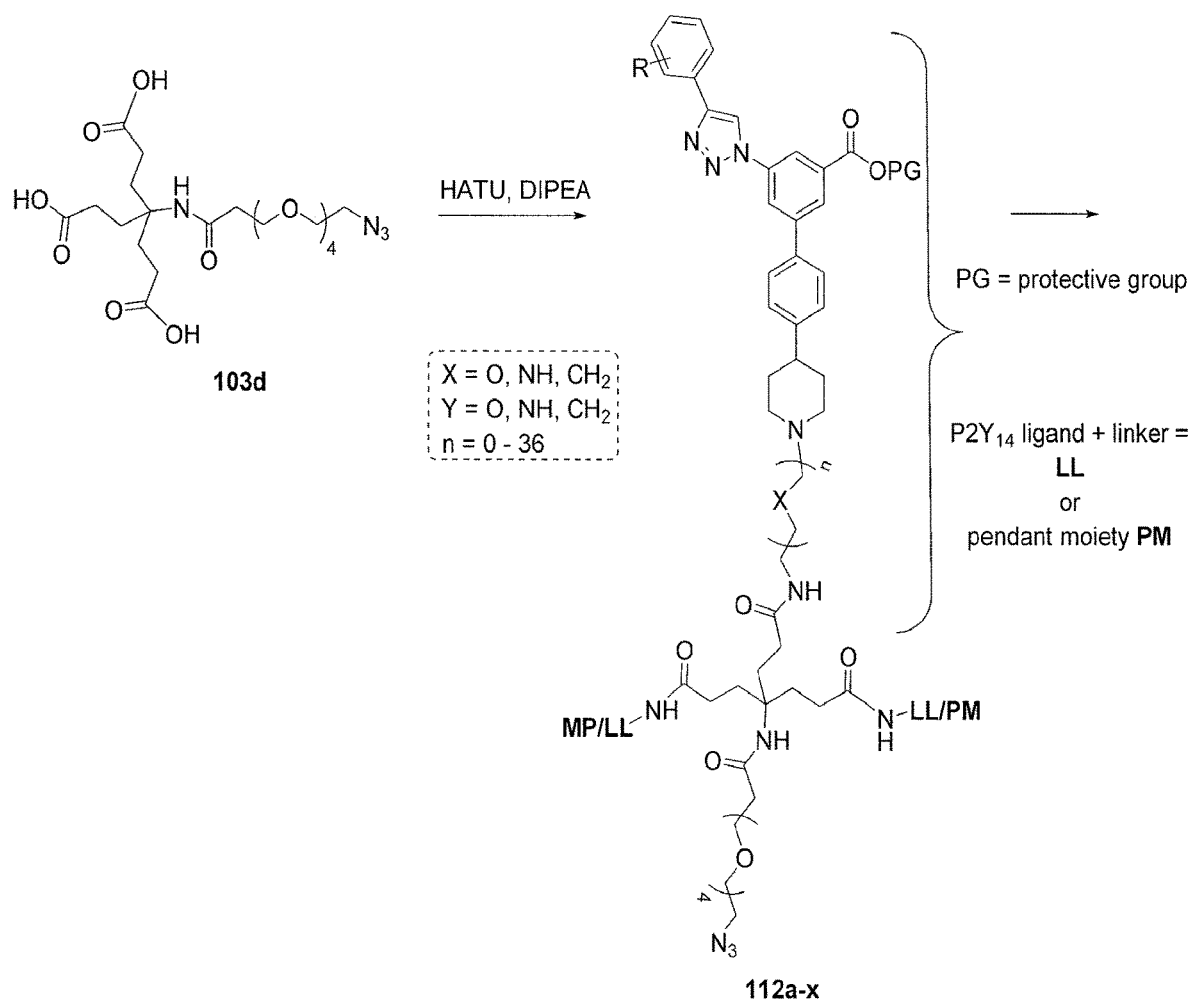
FIGS. 9A-9C represent a single chemical scheme of proposed Strategy 1 for preparing a dendron conjugate of formula (II).
Figure 9B:
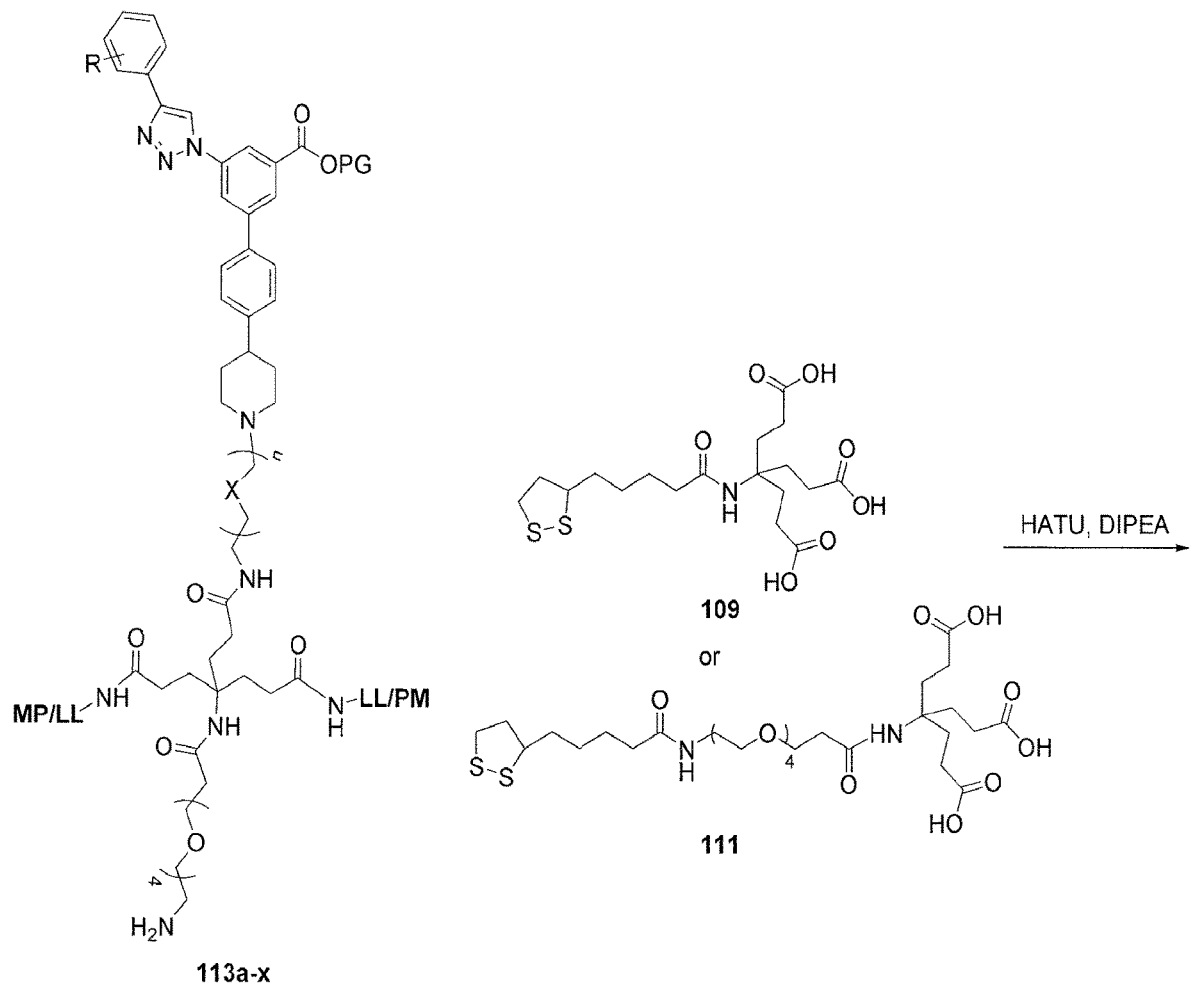
Figure 9C:
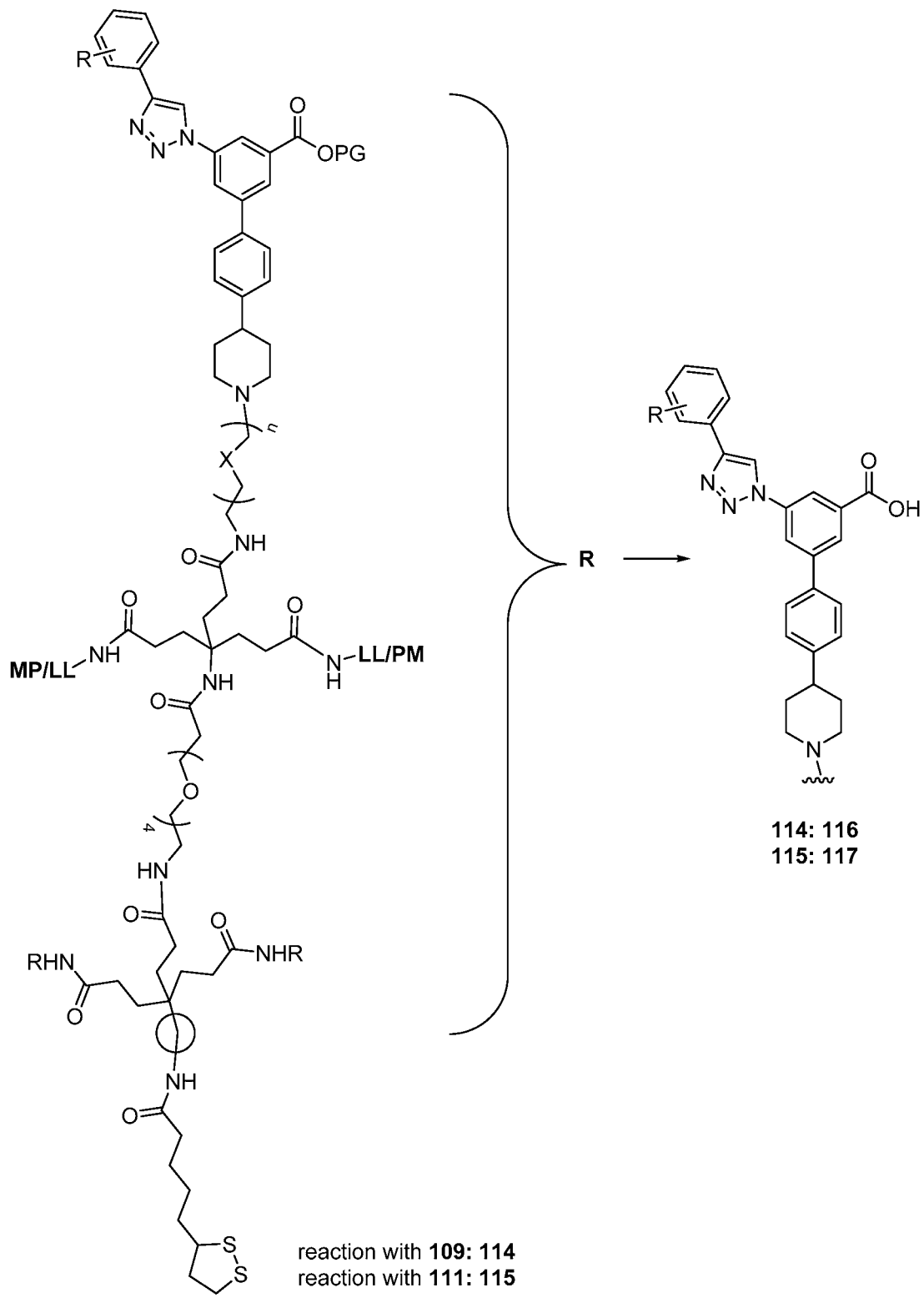
Figure 10A:
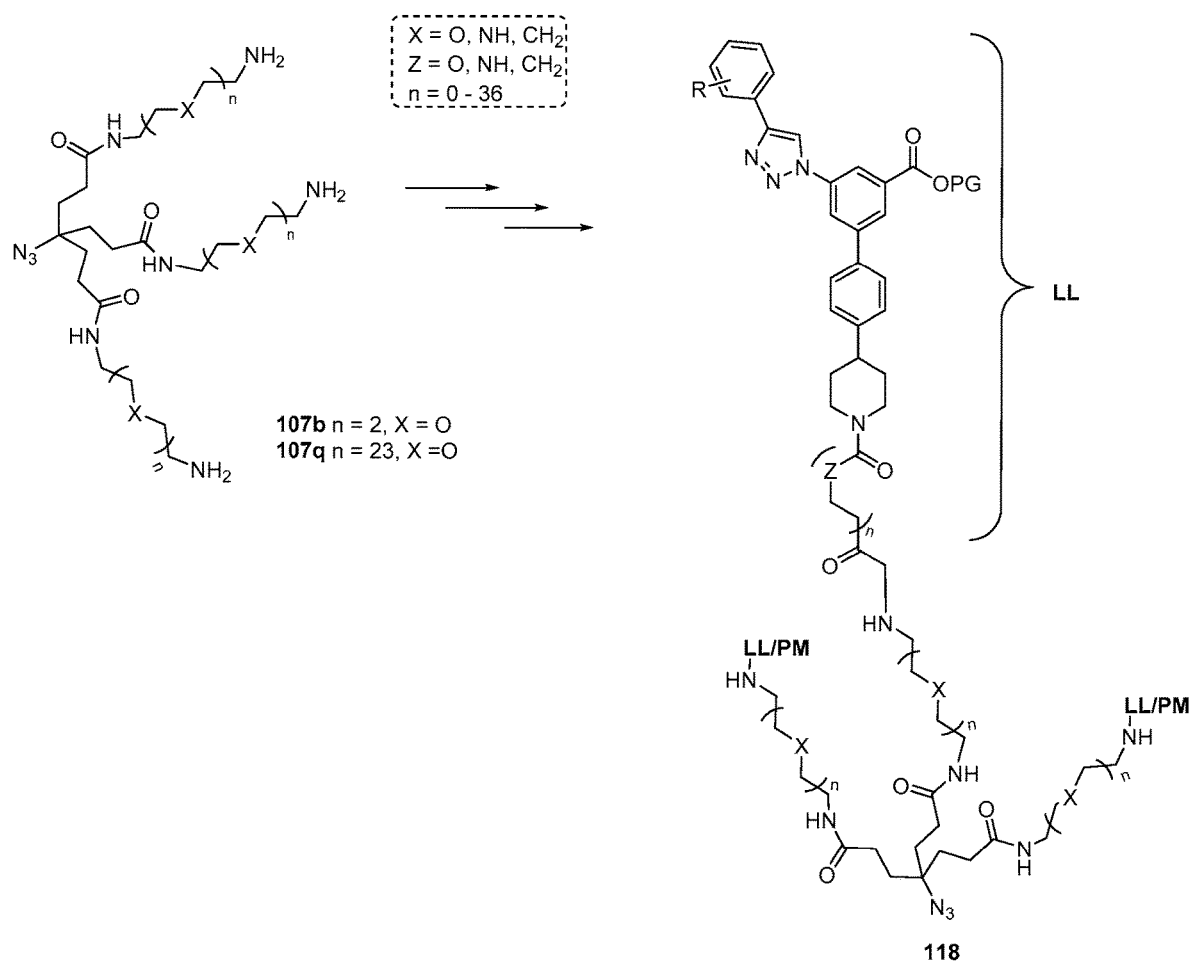
FIGS. 10A-10C represent a single chemical scheme of proposed Strategy 2 for preparing a dendron conjugate of formula (II).
Figure 10B:
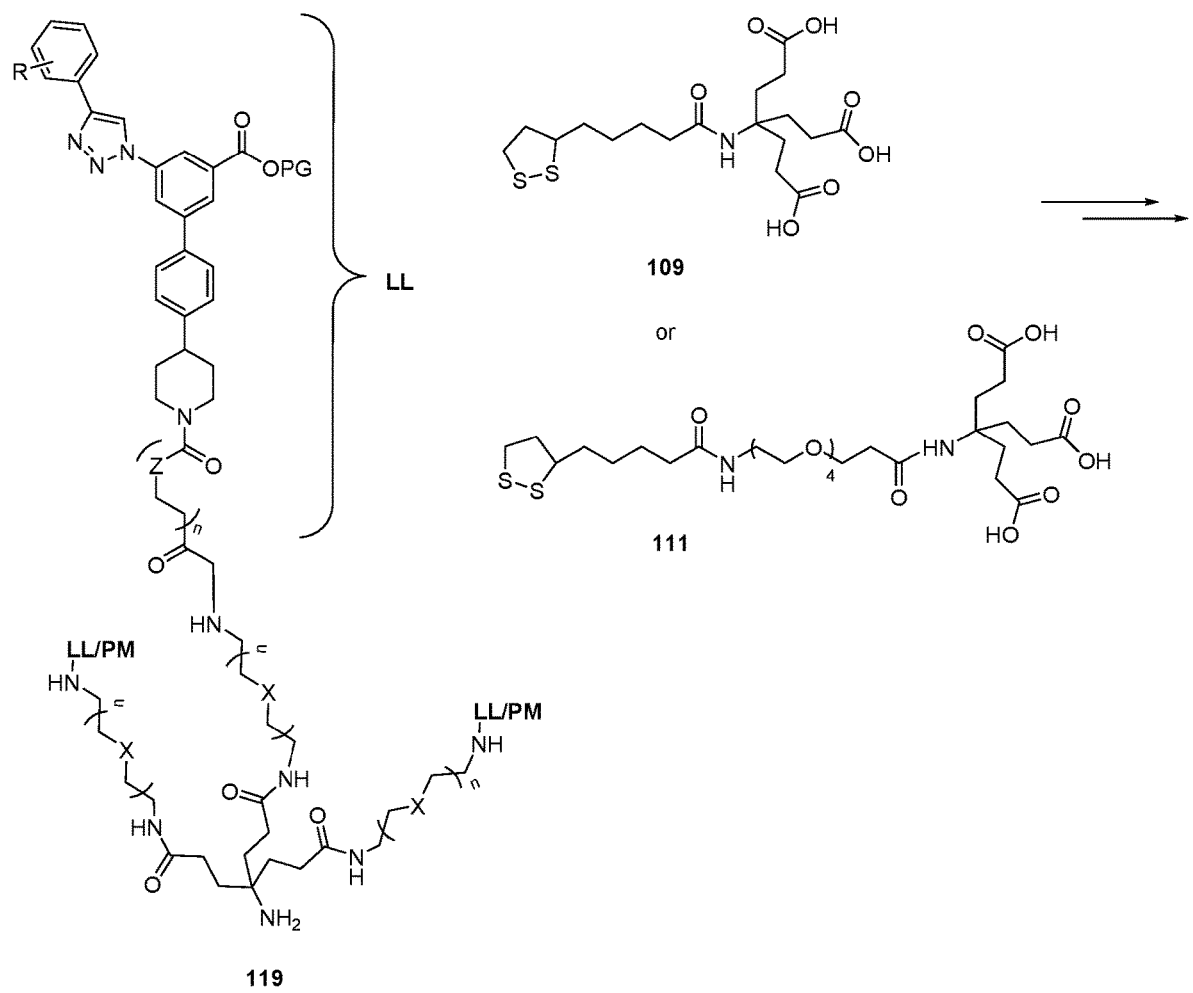
Figure 10C:
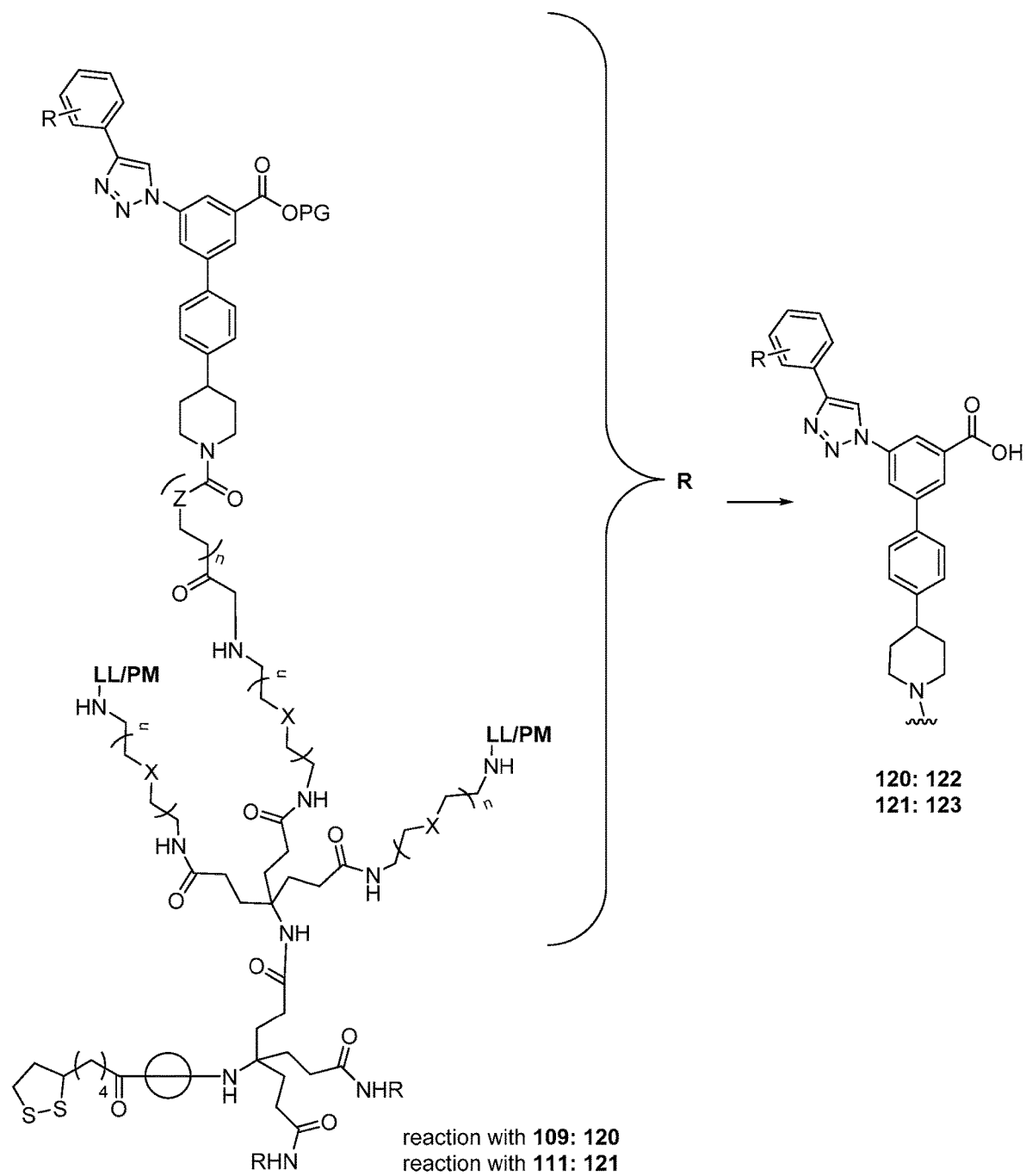
Figure 11:
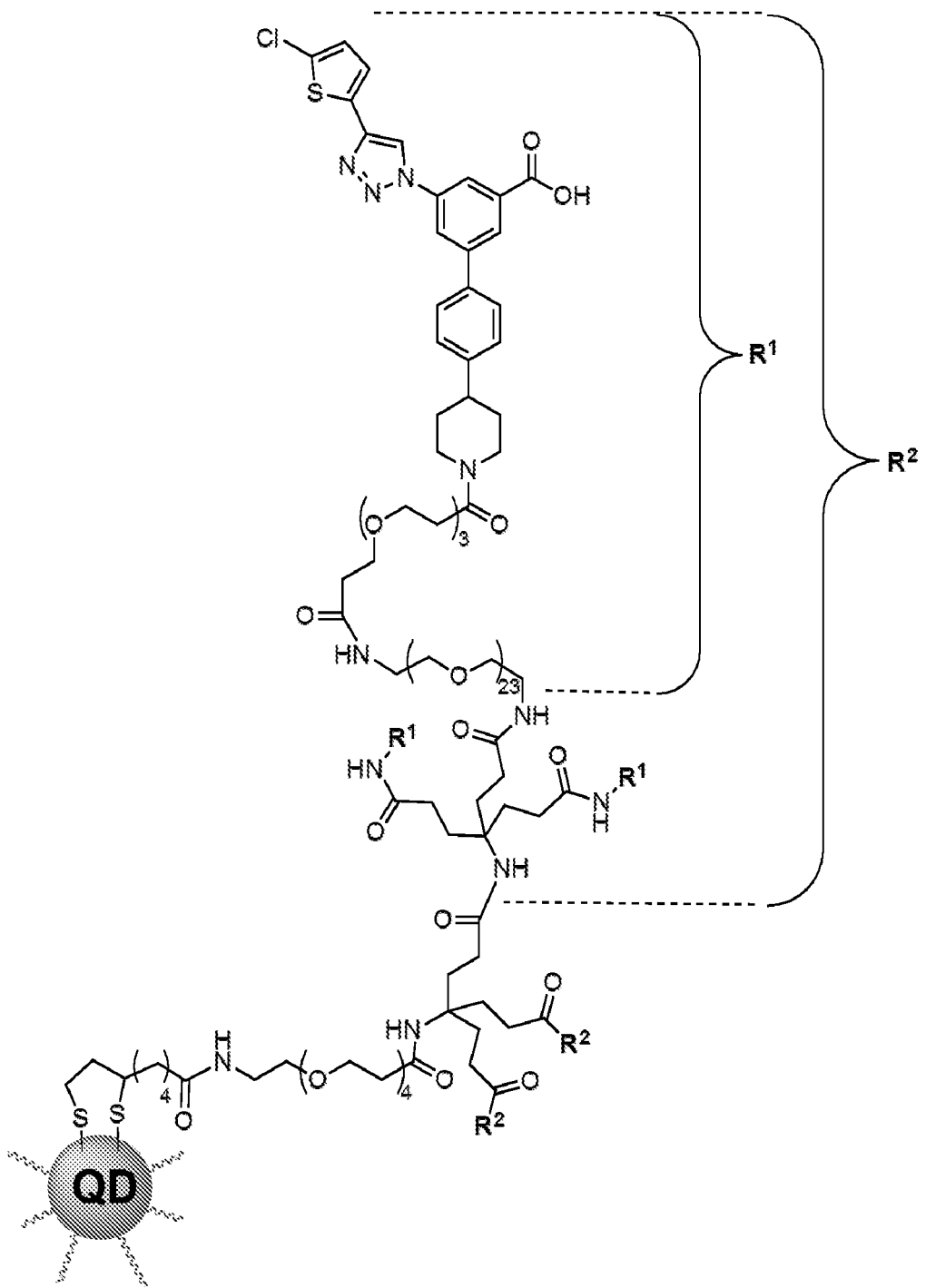
FIG. 11 illustrates a dendron conjugate of formula (II) covalently linked to a quantum dot.
Figure 12:
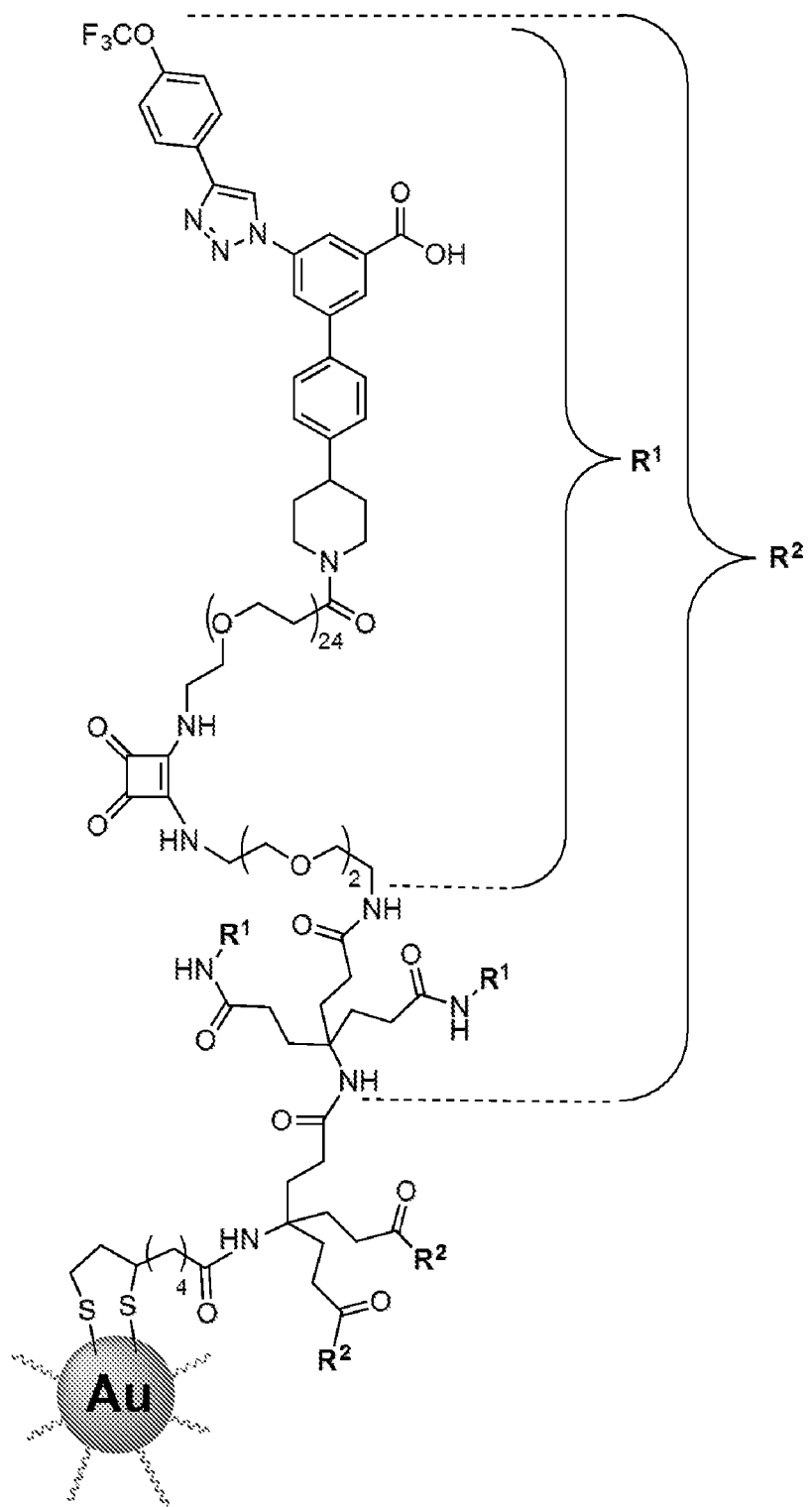
FIG. 12 illustrates a dendron conjugate of formula (II) covalently linked to a gold particle.

Two proposed routes to the final dendrimer conjugates are detailed in Strategy 1 (FIGS. 9A-9C) and Strategy 2 (FIGS. 10A-10C). FIGS. 11 and 12 illustrate the conjugation of a dendron conjugate of the invention to a particle, such as a quantum dot (FIG. 11) or a gold particle (FIG. 12), through a reactive sulfur atom that is part of $R^5$.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I), formula (II), formula (III), or formula (IV), wherein
   (a) the compound of formula (I) is of the formula:

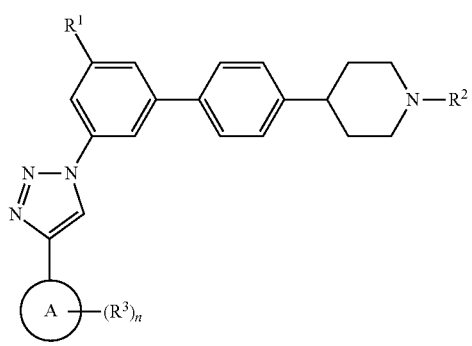

(I)

wherein
   ring A is aryl, heteroaryl, or cycloalkyl;
   $R^1$ is $CO_2H$, $—CO_2(C_1-C_8$ alkyl), or a bioisostere of carboxylate;
   $R^2$ is H, $C_1-C_8$ alkyl, $C_2-C_8$ alkenyl, $C_2-C_8$ alkynyl, $C_3-C_6$ cycloalkyl, $C_3-C_6$ cycloalkylalkyl, hydroxyalkyl, $C_1-C_8$ haloalkyl, cyanoalkyl, aryl, heteroaryl, heterocycloalkyl, $—(CH_2)_m$aryl, $—(CH_2)_m$heteroaryl, or $—(CH_2)_m$heterocycloalkyl;
   each $R^3$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy, $C_3-C_6$ cycloalkyloxy, aryloxy, halo, $C_1-C_8$ haloalkyl, $C_1-C_8$ haloalkoxy, $—CN$, $—NO_2$, $—NR^5R^6$, $—C(O)R^4$, $—CO_2R^4$, $—C(O)NR^5R^6$, $—NR^5C(O)R^4$, $—(CH_2)_m$aryl, $—(CH_2)_m$heteroaryl, or $—(CH_2)_m$heterocycloalkyl;
   $R^4$, $R^5$, and $R^6$ are the same or different and each is H or $C_1-C_8$ alkyl; and
   m and n are the same or different and each is 0 or an integer from 1-5;
or a pharmaceutically acceptable salt thereof;
   (b) the compound of formula (II) is of the formula:

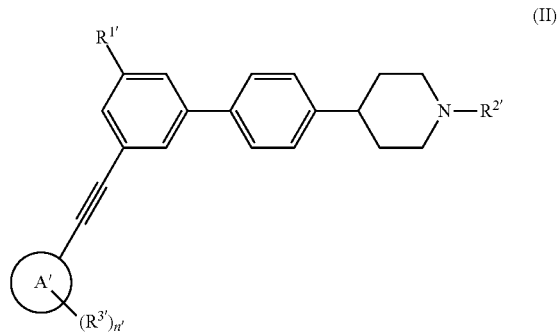

(II)

wherein
   ring A' is aryl, heteroaryl, or cycloalkyl;
   $R^{1'}$ is $CO_2H$, $—CO_2(C_1-C_8$ alkyl), or a bioisostere of carboxylate;
   $R^{2'}$ is H, $C_1-C_8$ alkyl, $C_2-C_8$ alkenyl, $C_2-C_8$ alkynyl, $C_3-C_6$ cycloalkyl, $C_3-C_6$ cycloalkylalkyl, hydroxyalkyl, $C_1-C_8$ haloalkyl, cyanoalkyl, aryl, heteroaryl, heterocycloalkyl, $—(CH_2)_m$aryl, $—(CH_2)_m$heteroaryl, or $—(CH_2)_m$heterocycloalkyl;
   each $R^{3'}$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy, $C_3-C_6$ cycloalkyloxy, aryloxy, halo, $C_1-C_8$ haloalkyl, $C_1-C_8$ haloalkoxy, $—CN$, $—NO_2$, $—NR^{5'}R^{6'}$, $—C(O)R^{4'}$, $—CO_2R^{4'}$, $—C(O)NR^{5'}R^{6'}$, $—NR^{5'}C(O)R^{4'}$, $—(CH_2)_m$aryl, $—(CH_2)_m$heteroaryl, or $—(CH_2)_m$heterocycloalkyl;
   $R^{4'}$, $R^{5'}$, and $R^{6'}$ are the same or different and each is H or $C_1-C_8$ alkyl; and
   m' and n' are the same or different and each is 0 or an integer from 1-5;
or a pharmaceutically acceptable salt thereof;
   (c) the compound of formula (III) is a conjugate of the formula:

(III)

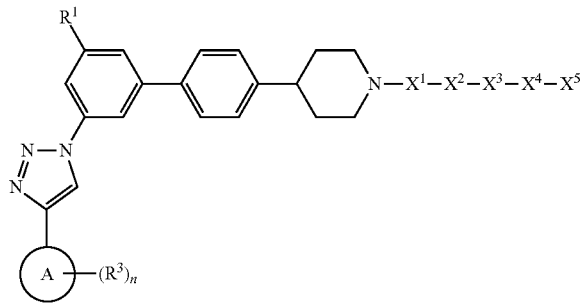

or a pharmaceutically acceptable salt thereof, wherein
ring A is aryl, heteroaryl, or cycloalkyl;
$R^1$ is —$CO_2H$, —$CO_2(C_1$-$C_8$ alkyl), or a bioisostere of carboxylate;
each $R^3$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —$NO_2$, —$NR^5R^6$, —$C(O)R^4$, —$CO_2R^4$, —$C(O)NR^5R^6$, —$NR^5C(O)R^4$, —$(CH_2)_m$aryl, —$(CH_2)_m$heteroaryl, or —$(CH_2)_m$heterocycloalkyl;
$R^4$, $R^5$, and $R^6$ are the same or different and each is H or $C_1$-$C_8$ alkyl;
$X^1$ is selected from the group consisting of —$(CH_2)_o$—, —C(O)—, —C(O)NH—, —OC(O)NH—, —OC(O)—, —C(O)O—, —C(S)NH—, and —$SO_2$—;
$X^2$ is selected from the group consisting of

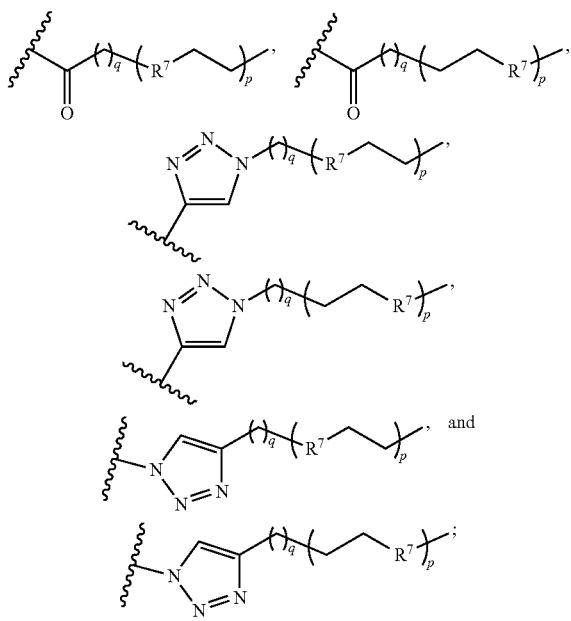

$R^7$ is $CH_2$, NH, or O;
$X^3$ is a dendron;
$X^4$ is selected from the group consisting of —$(CH_2)_o$—, —C(O)—, —C(O)NH—, —OC(O)NH—, —OC(O)—, —C(O)O—, —C(S)NH—, —$SO_2$—, —NHC(O)—, and

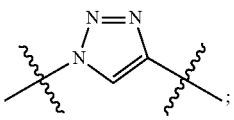 [SMILES: *c1cn(*)nn1]

$X^5$ is a reactive sulfur-containing moiety;
m, n, and q are the same or different and each is 0 or an integer from 1-5;
o is an integer from 1-5; and
p is 0 or an integer from 1-36;
wherein $X^5$ is optionally linked to a particle; and
(d) the compound of formula (IV) is a dendron conjugate of the formula:

(IV)

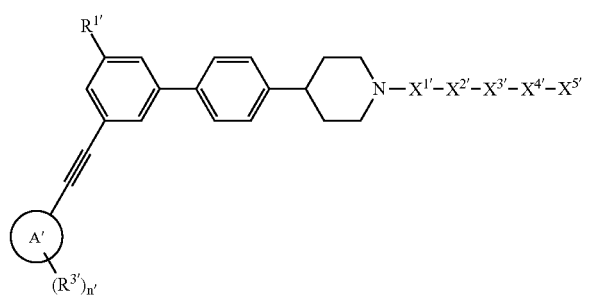

or a pharmaceutically acceptable salt thereof, wherein
ring A' is aryl, heteroaryl, or cycloalkyl;
$R^{1'}$ is —$CO_2H$, —$CO_2(C_1$-$C_8$ alkyl), or a bioisostere of carboxylate;
each $R^{3'}$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —$NO_2$, —$NR^{5'}R^{6'}$, —$C(O)R^{4'}$, —$CO_{2R}^{4'}$, —$C(O)NR^{5'}R^{6'}$, —$NR^{5'}C(O)R^{4'}$, —$(CH_2)_m$aryl, —$(CH_2)_m$heteroaryl, or —$(CH_2)_m$heterocycloalkyl;
$R^{4'}$, $R^{5'}$, and $R^{6'}$ are the same or different and each is H or $C_1$-$C_8$ alkyl;
$X^{1'}$ is selected from the group consisting of —$(CH_2)O$—, —C(O)—, —C(O)NH—, —OC(O)NH—, —OC(O)—, —C(O)O—, —C(S)NH—, and —$SO_2$—;
$X^{2'}$ is selected from the group consisting of;

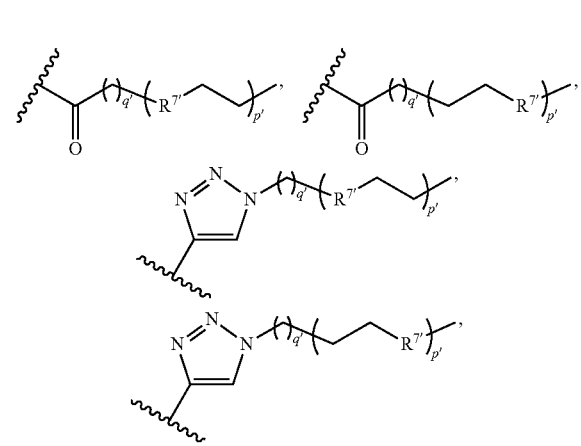

-continued

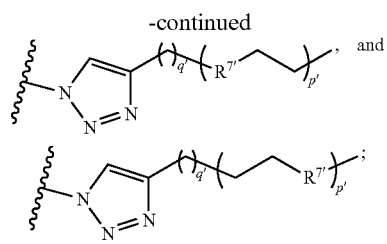

R[7'] is CH$_2$, NH, or O;
X[3'] is a dendron;
X[4'] is selected from the group consisting of —(CH$_2$)$_{o'}$—, —C(O)—, —C(O)NH—, —OC(O)NH—, —OC(O)—, —C(O)O—, —C(S)NH—, —SO$_2$—, —NHC(O)—, and

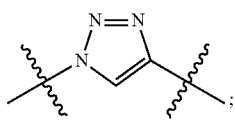 [SMILES: *c1cn(*)nn1]

m', n', and q' are the same or different and each is 0 or an integer from 1-5;
o' is an integer from 1-5; and
p' is 0 or an integer from 1-36;
wherein X[5'] is optionally linked to a particle.

2. The compound of claim 1, wherein in formula (I), ring A is phenyl, furanyl, thiazolyl, thienyl, pyrazolyl, pyridazinyl, pyridinyl, pyrazinyl, benzofuranyl, cyclopropyl, or cyclohexyl, or a pharmaceutically acceptable salt thereof.

3. The compound of claim 2, wherein in formula (I), ring A is phenyl, or a pharmaceutically acceptable salt thereof.

4. The compound of claim 1, wherein in formula (I), R[1] is —CO$_2$H, or a pharmaceutically acceptable salt thereof.

5. The compound of claim 1, wherein in formula (I), R[1] is a bioisostere of carboxylate selected from the group consisting of

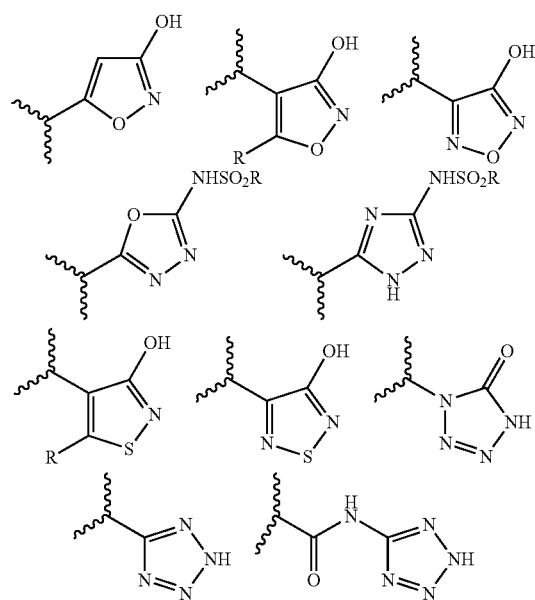

-continued

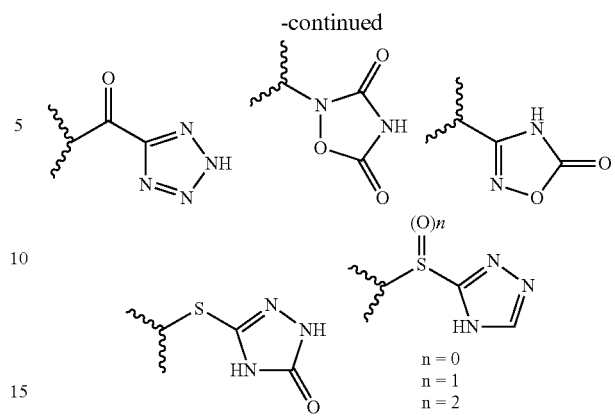

n = 0
n = 1
n = 2

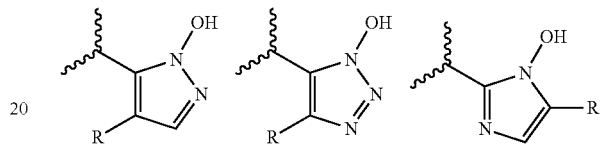

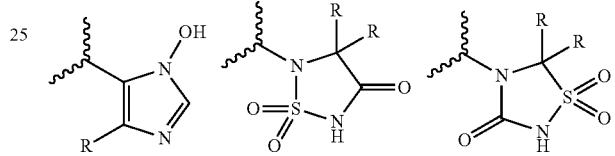

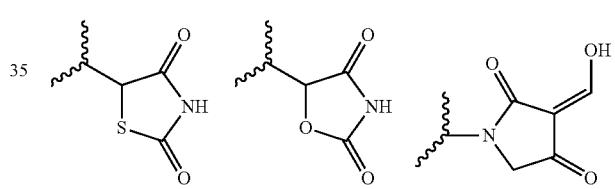

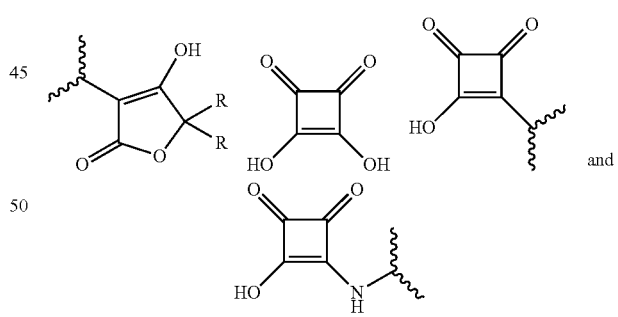

and or a pharmaceutically acceptable salt thereof.

6. The compound of claim 1, wherein in formula (I), R[2] is H or C$_2$-C$_8$ alkynyl, or a pharmaceutically acceptable salt thereof.

7. The compound of claim 1, wherein in formula (I), R[3] is C$_1$-C$_8$ alkyl, hydroxy, hydroxyalkyl, C$_1$-C$_8$ alkoxy, halo, C$_1$-C$_8$ haloalkyl, C$_1$-C$_8$ haloalkoxy, —CN, —NH$_2$, —CO$_2$R[4], or a pharmaceutically acceptable salt thereof.

8. The compound of claim 1, wherein in formula (I), n is 0, 1, or 2.

9. The compound of claim 1, wherein in formula (I),
R¹ is —CO₂H;
R² is H; and
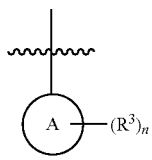
is selected from the group consisting of
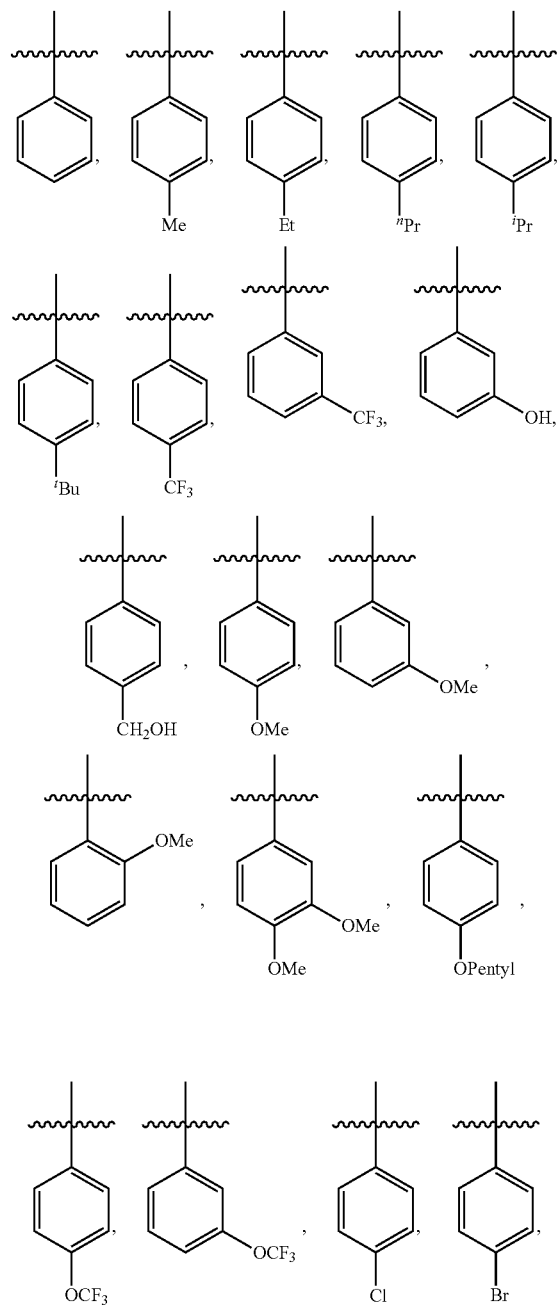
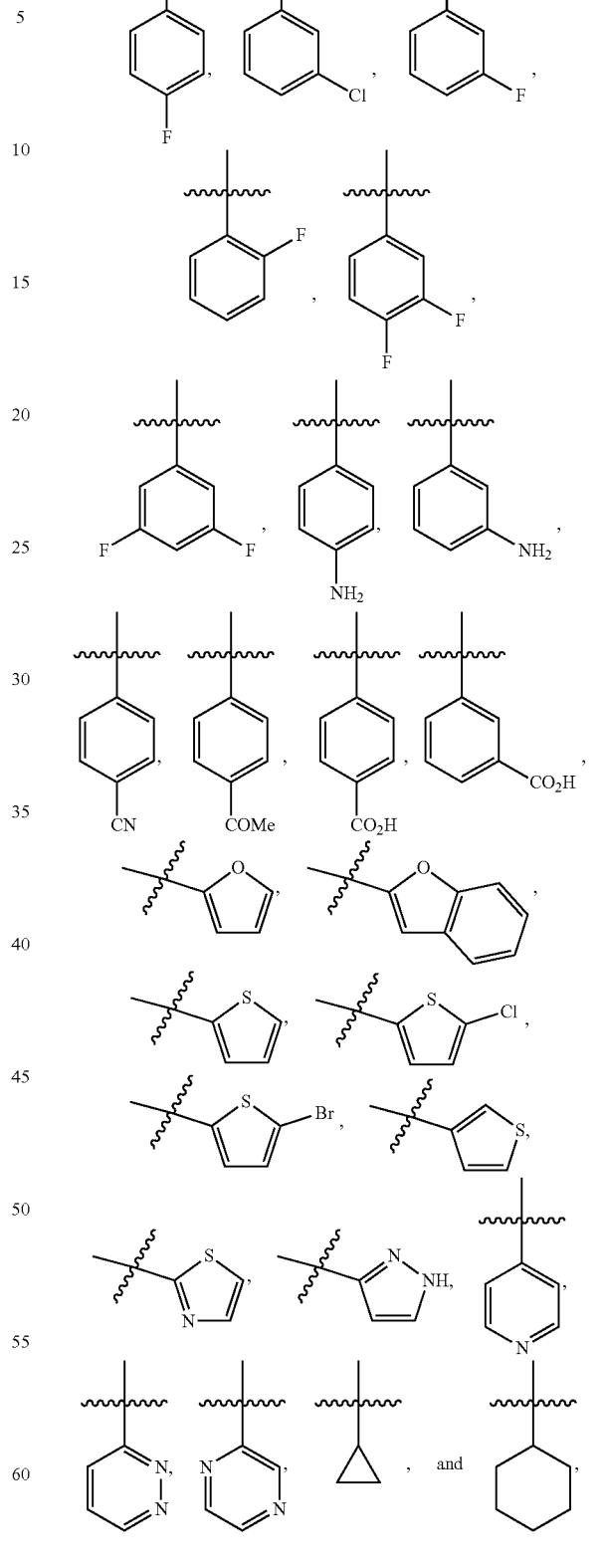
or a pharmaceutically acceptable salt thereof.
10. The compound of claim 1, wherein the compound is a compound of formula (II):

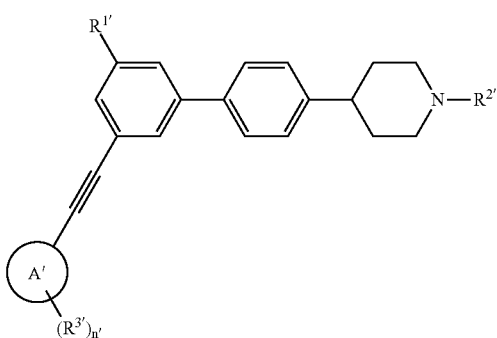

(II)

wherein
ring A' is aryl, heteroaryl, or cycloalkyl;
R$^{1'}$ is —CO$_2$H, —CO$_2$(C$_1$-C$_8$ alkyl), or a bioisostere of carboxylate;
R$^{2'}$ is H, C$_1$-C$_8$ alkyl, C$_2$-C$_8$ alkenyl, C$_2$-C$_8$ alkynyl, C$_3$-C$_6$ cycloalkyl, C$_3$-C$_6$ cycloalkylalkyl, hydroxyalkyl, C$_1$-C$_8$ haloalkyl, cyanoalkyl, aryl, heteroaryl, heterocycloalkyl, —(CH$_2$)$_m$aryl, —(CH$_2$)$_m$heteroaryl, or —(CH$_2$)$_m$heterocycloalkyl;
each R$^{3'}$ is the same or different and each is C$_1$-C$_8$ alkyl, C$_2$-C$_8$ alkenyl, C$_3$-C$_6$ cycloalkyl, hydroxy, hydroxyalkyl, C$_1$-C$_8$ alkoxy, C$_3$-C$_6$ cycloalkyloxy, aryloxy, halo, C$_1$-C$_8$ haloalkyl, C$_1$-C$_8$ haloalkoxy, —CN, —NO$_2$, —NR$^{5'}$R$^{6'}$, —C(O)R$^{4'}$, —CO$_2$R$^{4'}$, —C(O)NR$^{5'}$R$^{6'}$, —NR$^{5'}$C(O)R$^{4'}$, —(CH$_2$)$_m$aryl, —(CH$_2$)$_m$heteroaryl, or —(CH$_2$)$_m$heterocycloalkyl;
R$^{4'}$, R$^{5'}$, and R$^{6'}$ are the same or different and each is H or C$_1$-C$_8$ alkyl; and
m' and n' are the same or different and each is 0 or an integer from 1-5;
or a pharmaceutically acceptable salt thereof.

11. The compound of claim 1, wherein the compound is a conjugate of formula (III)

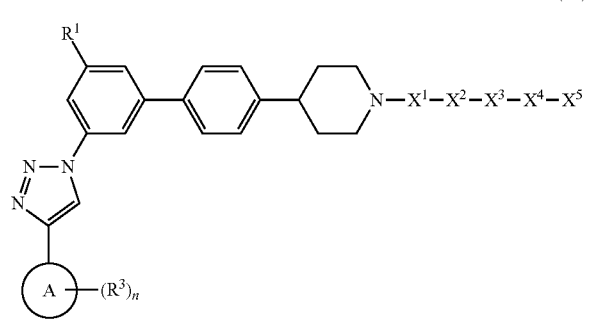

(III)

or a pharmaceutically acceptable salt thereof, wherein
ring A is aryl, heteroaryl, or cycloalkyl;
R$^1$ is —CO$_2$H, —CO$_2$(C$_1$-C$_8$ alkyl), or a bioisostere of carboxylate;
each R$^3$ is the same or different and each is C$_1$-C$_8$ alkyl, C$_2$-C$_8$ alkenyl, C$_3$-C$_6$ cycloalkyl, hydroxy, hydroxyalkyl, C$_1$-C$_8$ alkoxy, C$_3$-C$_6$ cycloalkyloxy, aryloxy, halo, C$_1$-C$_8$ haloalkyl, C$_1$-C$_8$ haloalkoxy, —CN, —NO$_2$, —NR$^5$R$^6$, —C(O)R$^4$, —CO$_2$R$^4$, —C(O)NR$^5$R$^6$, —NR$^5$C(O)R$^4$, —(CH$_2$)$_m$aryl, —(CH$_2$)$_m$heteroaryl, or —(CH$_2$)$_m$heterocycloalkyl;

R$^4$, R$^5$, and R$^6$ are the same or different and each is H or C$_1$-C$_8$ alkyl;
X$^1$ is selected from the group consisting of —(CH$_2$)$_o$—, —C(O)—, —C(O)NH—, —OC(O)NH—, —OC(O)—, —C(O)O—, —C(S)NH—, and —SO$_2$—;
X$^2$ is selected from the group consisting of

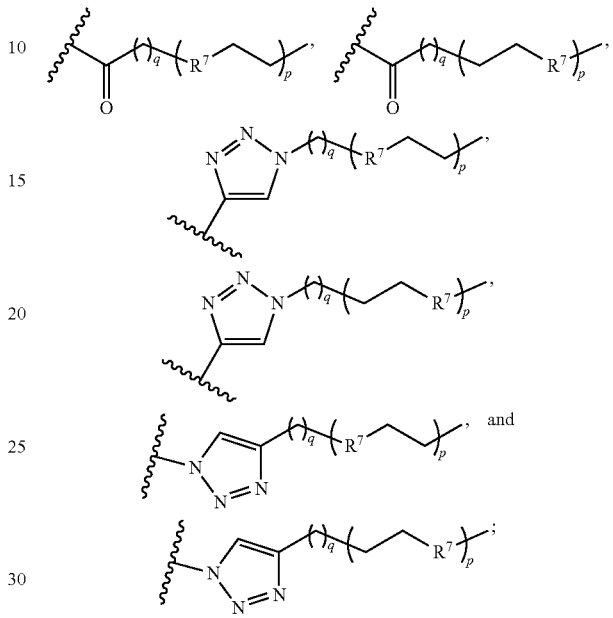

R$^7$ is CH$_2$, NH, or O;
X$^3$ is a dendron;
X$^4$ is selected from the group consisting of —(CH$_2$)$_o$—, —C(O)—, —C(O)NH—, —OC(O)NH—, —OC(O)—, —C(O)O—, —C(S)NH—, —SO$_2$—, —NHC(O)—, and

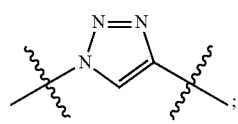 [SMILES: *c1cn(*)nn1]

X$^5$ is a reactive sulfur-containing moiety;
m, n, and q are the same or different and each is 0 or an integer from 1-5;
o is an integer from 1-5; and
p is 0 or an integer from 1-36;
wherein X$^5$ is optionally linked to a particle.

12. The compound of claim 11, wherein in formula (III), the dendron is carboxyethylpolyamido (CEPAM) dendron that is optionally functionalized in at least one position to include the moiety

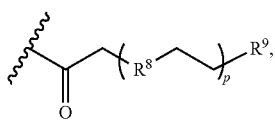

wherein R$^8$ is CH$_2$, NH, or O, and R$^9$ is —NH$_2$ or —CO$_2$H.

13. The compound of claim 12, wherein in formula (III), the dendron is of generation G1, G2, or G3.

14. The compound of claim 11, wherein the compound of formula (III) is linked to a particle through a sulfur atom of $X^5$.

15. The compound of claim 14, wherein the particle is a quantum dot, a non-metallic particle, or a metallic particle.

16. The compound of claim 1, wherein the compound is a dendron conjugate of formula (IV)

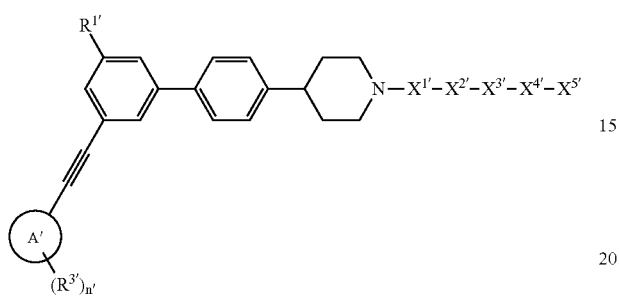

(IV)

or a pharmaceutically acceptable salt thereof, wherein
ring A' is aryl, heteroaryl, or cycloalkyl;
$R^{1'}$ is —$CO_2H$, —$CO_2(C_1$-$C_8$ alkyl), or a bioisostere of carboxylate;
$R^{2'}$ is H, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyalkyl, $C_1$-$C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl;
each $R^{3'}$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —$NO_2$, —$C(O)R^{4'}$, —$CO_2R^{4'}$, —$C(O)NR^{5'}R^{6'}$, —$NR^{5'}C(O)R^{4'}$, —$(CH_2)_m$aryl, —$(CH_2)_m$heteroaryl, or —$(CH_2)_m$heterocycloalkyl;
$R^{4'}$, $R^{5'}$, and $R^{6'}$ are the same or different and each is H or $C_1$-$C_8$ alkyl;
$X^{1'}$ is selected from the group consisting of —$(CH_2)_{o'}$—, —C(O)—, —C(O)NH—, —OC(O)NH—, —OC(O)—, —C(O)O—, —C(S)NH—, and —$SO_2$—;
$X^{2'}$ is selected from the group consisting of

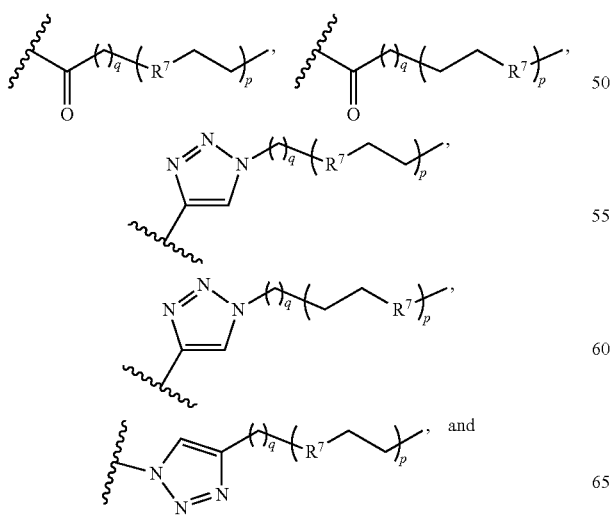

-continued

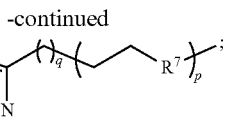

$R^{7'}$ is $CH_2$, NH, or O;
$X^{3'}$ is a dendron;
$X^{4'}$ is selected from the group consisting of —$(CH_2)_{o'}$—, —C(O)—, —C(O)NH—, —OC(O)NH—, —OC(O)—, —C(O)O—, —C(S)NH—, —$SO_2$—, —NHC(O)—, and

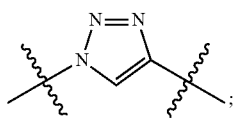 [SMILES: *c1cn(*)nn1]

$X^{5'}$ is a reactive sulfur-containing moiety;
m', n', and q' are the same or different and each is 0 or an integer from 1-5;
o' is an integer from 1-5; and
p' is 0 or an integer from 1-36;
wherein $X^{5'}$ is optionally linked to a particle.

17. A pharmaceutical composition comprising (i) at least one compound of claim 1 or a pharmaceutically acceptable salt thereof and (ii) a pharmaceutically acceptable carrier.

18. A method of antagonizing $P2Y_{14}$ receptor ($P2Y_{14}R$) activity in a cell comprising contacting the cell with the compound of claim 1 or a pharmaceutically acceptable salt thereof.

19. A method of treating a disease in a subject in need thereof comprising administering to the subject an effective amount of the compound of claim 1 or a pharmaceutically acceptable salt thereof, wherein the disease is inflammation, diabetes, or insulin resistance.

20. A dendron conjugate of formula (V) or (VI), or a pharmaceutically acceptable salt thereof;
wherein in formula (V):

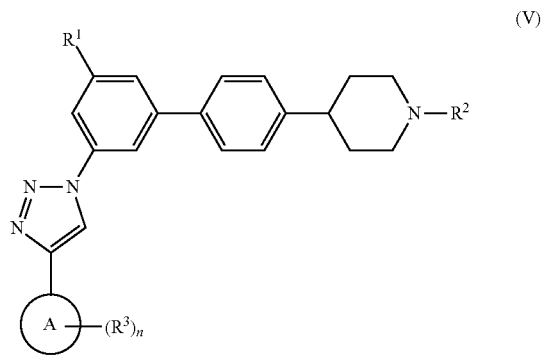

(V)

ring A is aryl, heteroaryl, or cycloalkyl;
$R^1$ is —$CO_2H$, —$CO_2(C_1$-$C_8$ alkyl), or a bioisostere of carboxylate;
$R^2$ is dendron;
each $R^3$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —$NO_2$, —$NR^5R^6$, —$C(O)R^4$, —$CO_2R^4$, —C(O)

$NR^5R^6$, $-NR^5C(O)R^4$, $-(CH_2)_m$aryl, $-(CH_2)_m$heteroaryl, or $-(CH_2)_m$heterocycloalkyl;

$R^4$, $R^5$, and $R^6$ are the same or different and each is H or $C_1$-$C_8$ alkyl; and m and n are the same or different and each is 0 or an integer from 1-5;

and in formula (VI):

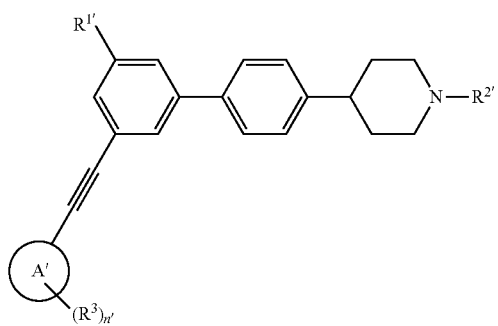
(VI)

ring A' is aryl, heteroaryl, or cycloalkyl;
$R^{1'}$ is $-CO_2H$, $-CO_2(C_1$-$C_8$ alkyl), or a bioisostere of carboxylate;
$R^{2'}$ is a dendron;
each $R^{3'}$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, $-CN$, $-NO_2$, $-NR^{5'}R^{6'}$, $-C(O)R^{4'}$, $-CO_2R^{4'}$, $-C(O)NR^{5'}R^{6'}$, $-NR^{5'}C(O)R^{4'}$, $-(CH_2)_m$aryl, $-(CH_2)_m$heteroaryl, or $-(CH_2)_m$heterocycloalkyl;

$R^{4'}$, $R^{5'}$, and $R^{6'}$ are the same or different and each is H or $C_1$-$C_8$ alkyl; and m' and n' are the same or different and each is 0 or an integer from 1-5.

21. A pharmaceutical composition comprising (i) a dendron conjugate of claim 20, or a pharmaceutically acceptable salt thereof, and (ii) a pharmaceutically acceptable carrier.

22. A method of antagonizing $P2Y_{14}$ receptor ($P2Y_{14}R$) activity in a cell comprising contacting the cell with a dendron conjugate of claim 20 or a pharmaceutically acceptable salt thereof.

23. A method of treating a disease in a subject in need thereof comprising administering to the subject an effective amount of a dendron conjugate of claim 20 or a pharmaceutically acceptable salt thereof, wherein the disease is inflammation, diabetes, or insulin resistance.

* * * * *